US008604031B2

(12) United States Patent
Flynn et al.

(10) Patent No.: US 8,604,031 B2
(45) Date of Patent: Dec. 10, 2013

(54) INTRACELLULAR KINASE INHIBITORS

(75) Inventors: Gary A. Flynn, Tucson, AZ (US);
Sandra Aeyoung Lee, Sherman Oaks, CA (US); Mary Faris, Los Angeles, CA (US); David William Brandt, Moorpark, CA (US); Subrata Chakravarty, Valencia, CA (US)

(73) Assignee: MannKind Corporation, Valencia, CA (US)

( * ) Notice: Subject to any disclaimer, the term of this patent is extended or adjusted under 35 U.S.C. 154(b) by 1556 days.

(21) Appl. No.: 11/750,866

(22) Filed: May 18, 2007

(65) Prior Publication Data

US 2007/0293499 A1 Dec. 20, 2007

Related U.S. Application Data

(60) Provisional application No. 60/801,074, filed on May 18, 2006, provisional application No. 60/869,664, filed on Dec. 12, 2006.

(51) Int. Cl.
*A61K 31/535* (2006.01)
(52) U.S. Cl.
USPC ...................................................... 514/238.8
(58) Field of Classification Search
USPC ........................................................ 514/238.8
See application file for complete search history.

(56) References Cited

U.S. PATENT DOCUMENTS

| | | |
|---|---|---|
| 2,282,907 A | 5/1942 | ter Horst |
| 2,649,444 A | 8/1953 | Barrett |
| 2,771,391 A | 11/1956 | Backstahler |
| 2,778,853 A | 1/1957 | Schultz |
| 2,997,479 A | 8/1961 | Schlesinger |
| 3,080,372 A | 3/1963 | Janssen |
| 3,151,124 A | 9/1964 | Huebner |
| 3,203,962 A | 8/1965 | Huebner |
| 3,249,606 A | 5/1966 | Pellegrini |
| 3,252,996 A | 5/1966 | Huebner |
| 3,284,453 A | 11/1966 | Stephen |
| 3,305,562 A | 2/1967 | Heffe |
| 3,310,566 A | 3/1967 | Freed |
| 3,314,970 A | 4/1967 | Seeger |
| 3,317,538 A | 5/1967 | Freed |
| 3,364,210 A | 1/1968 | Safir |
| 3,417,087 A | 12/1968 | Campaigne |
| 3,448,192 A | 6/1969 | Mauvernay |
| 3,450,704 A | 6/1969 | Osbond |
| 3,465,080 A | 9/1969 | Wright |
| 3,637,704 A | 1/1972 | Unomoto |
| 3,651,067 A | 3/1972 | Elpern |
| 3,651,085 A | 3/1972 | Lunsford |
| 3,658,821 A | 4/1972 | Fauran |
| 3,681,359 A | 8/1972 | Leigh |
| 3,703,527 A | 11/1972 | Saucy |
| 3,753,983 A | 8/1973 | Raabe |
| 3,767,802 A | 10/1973 | Denss |
| 3,770,734 A | 11/1973 | Pesson et al. |
| 3,772,275 A | 11/1973 | Hernestam |
| 3,794,677 A | 2/1974 | Bruce |
| 3,799,932 A | 3/1974 | Yamamoto |
| 3,806,526 A | 4/1974 | Carr |
| 3,812,118 A | 5/1974 | Yamamoto |
| 3,816,433 A | 6/1974 | Hernestam |
| 3,850,935 A | 11/1974 | Nakao |
| 3,873,539 A | 3/1975 | Houlihan |
| 3,895,030 A | 7/1975 | Lafon |
| 3,900,478 A | 8/1975 | Krapcho |
| 3,907,812 A | 9/1975 | Yamamoto |
| 3,912,755 A | 10/1975 | Booher |
| 3,922,266 A | 11/1975 | Katsube |
| 3,931,197 A | 1/1976 | Carr |
| 3,936,468 A | 2/1976 | Yamamoto |
| 3,951,978 A | 4/1976 | Manghisi |
| 3,966,735 A | 6/1976 | Milkowski |
| 3,969,356 A | 7/1976 | Milkowski |
| 3,992,546 A | 11/1976 | Huebner |
| 3,995,047 A | 11/1976 | Morita |
| 4,028,366 A | 6/1977 | Zenitz |
| 4,029,801 A | 6/1977 | Cavalla |
| 4,045,566 A | 8/1977 | Archibald |
| 4,054,570 A | 10/1977 | Huebner |
| 4,062,956 A | 12/1977 | Mauvernay |
| 4,069,331 A | 1/1978 | Langbein |
| 4,075,346 A | 2/1978 | Sasajima |
| 4,122,199 A | 10/1978 | Cousse |
| 4,145,427 A | 3/1979 | Langbein |
| 4,148,796 A | 4/1979 | Yamamoto |
| 4,148,895 A | 4/1979 | Lattrell |

(Continued)

FOREIGN PATENT DOCUMENTS

BE 561 320 5/1960
EP 0 004 000 9/1979

(Continued)

OTHER PUBLICATIONS

Baiocchi & Bonanomi, "Aromatization of Aliphatic Compounds. IX. Benzofuanones from (4-Substituted 2-Oxo-3-Cyclohexen-1-yl) Acetic Acids," *Gazzetta Chimica Italiana* 119, 441-43, 1989.
Bazarbachi et al., "New therapeutic approaches for adult T-cell leukaemia," *The Lancet Oncology* 5, 664-72, Nov. 2004.
Brown et al., "Naphthyl Ketones: A New Class of Janus Kinase 3 Inhibitors," *Bioorganic & Medicinal Chemistry Letters* 10, 575-79, 2000.
Brown et al., "Crystal Structures of Interleukin-2 Tyrosine Kinase and Their Implications for the Design of Selective Inhibitors," *J. Biol. Chem. 279*, 18727-32, 2004.
Chawla et al., "Agents Acting on the Central Nervous System. XII. 3-t-Aminopropiophenones as Central Muscle Relaxants and Diuretics," *J. Medicinal chem. 13*, 480-88, 1970.
Gasparyan et al., "Synthesis and investigation of hydrochlorides of 1-(p-halophenyl)-1-alkyl(aryl)-3-morpholinopropan-1-ols," *Khimicheskii Zhurnal Armenii 56*, 78-84, 2003, including English abstract.

(Continued)

*Primary Examiner* — Ralph Gitomer
(74) *Attorney, Agent, or Firm* — Banner & Witcoff, Ltd.

(57) ABSTRACT

Intracellular kinase inhibitors and their therapeutic uses for patients with T cell malignancies, B cell malignancies, autoimmune disorders, and transplanted organs.

62 Claims, 3 Drawing Sheets

(56) References Cited

U.S. PATENT DOCUMENTS

| | | | |
|---|---|---|---|
| 4,169,892 A * | 10/1979 | Robba et al. | 514/64 |
| 4,181,803 A | 1/1980 | Morita | |
| 4,239,759 A | 12/1980 | Gante | |
| 4,241,207 A | 12/1980 | Boltze | |
| 4,272,533 A | 6/1981 | Gadient | |
| 4,277,474 A | 7/1981 | Kohda | |
| 4,283,404 A | 8/1981 | Carr | |
| 4,294,841 A | 10/1981 | Champseix | |
| 4,316,815 A | 2/1982 | Mercer | |
| 4,333,941 A | 6/1982 | Baratz | |
| 4,337,252 A | 6/1982 | Astoin | |
| 4,348,401 A | 9/1982 | Friebe | |
| 4,397,850 A | 8/1983 | Nadelson | |
| 4,400,380 A | 8/1983 | Ritter | |
| 4,465,678 A | 8/1984 | Knops | |
| 4,495,184 A | 1/1985 | Knops | |
| 4,515,793 A * | 5/1985 | Werbel et al. | 514/254.11 |
| 4,528,299 A | 7/1985 | Uno | |
| 4,544,663 A | 10/1985 | Manning | |
| 4,638,009 A | 1/1987 | Itho | |
| 4,665,076 A | 5/1987 | Mestre | |
| 4,695,652 A | 9/1987 | Seng | |
| 4,705,795 A | 11/1987 | Lafon | |
| 4,721,786 A | 1/1988 | Weissmüller | |
| 4,739,052 A | 4/1988 | Hüsler | |
| 4,755,522 A | 7/1988 | Lafon | |
| 4,758,560 A | 7/1988 | Lafon | |
| 4,791,045 A | 12/1988 | Mitra | |
| 4,840,950 A | 6/1989 | D'Ambra | |
| 4,870,083 A | 9/1989 | Carr | |
| 4,871,387 A | 10/1989 | Sasse | |
| 4,874,761 A | 10/1989 | D'Ambra | |
| 4,910,200 A | 3/1990 | Curtze | |
| 4,912,116 A | 3/1990 | Itoh | |
| 4,965,266 A | 10/1990 | Uno | |
| 4,992,547 A | 2/1991 | Berner | |
| 5,013,837 A | 5/1991 | Ward | |
| 5,057,535 A | 10/1991 | Shiozawa | |
| 5,077,402 A | 12/1991 | Desobry | |
| 5,116,979 A | 5/1992 | Fukazawa | |
| 5,182,284 A | 1/1993 | Suzuki | |
| 5,196,439 A | 3/1993 | Sugimoto | |
| 5,276,035 A | 1/1994 | Hohlweg | |
| 5,276,051 A | 1/1994 | Lesieur | |
| 5,280,020 A | 1/1994 | Bertini Curri | |
| 5,350,748 A | 9/1994 | Boschelli | |
| 5,472,962 A | 12/1995 | Koizumi | |
| 5,552,402 A | 9/1996 | Matassa | |
| 5,604,240 A | 2/1997 | Chambers | |
| 5,614,518 A | 3/1997 | Leeson | |
| 5,618,819 A | 4/1997 | Guillaumet | |
| 5,643,919 A | 7/1997 | Arndts | |
| 5,656,642 A | 8/1997 | Fujioka | |
| 5,705,501 A | 1/1998 | DeBernardis | |
| 5,705,509 A | 1/1998 | Gaster | |
| 5,760,058 A | 6/1998 | Fujioka | |
| 5,767,128 A | 6/1998 | Guillaumet | |
| 5,789,404 A | 8/1998 | Andersen | |
| 5,837,712 A | 11/1998 | Lösel | |
| 5,925,636 A | 7/1999 | Dyke | |
| 5,965,575 A | 10/1999 | Peglion | |
| 5,972,986 A | 10/1999 | Seibert | |
| 5,994,398 A | 11/1999 | John | |
| 6,022,906 A | 2/2000 | Ohwa | |
| 6,028,086 A | 2/2000 | Duplantier | |
| 6,051,243 A | 4/2000 | Bernardon | |
| 6,054,457 A | 4/2000 | Setoi | |
| 6,090,981 A | 7/2000 | Englert | |
| 6,127,379 A | 10/2000 | King | |
| 6,136,826 A | 10/2000 | Fujioka | |
| 6,207,665 B1 | 3/2001 | Bauman | |
| 6,211,242 B1 | 4/2001 | Setoi | |
| 6,214,994 B1 | 4/2001 | DeBernardis | |
| 6,235,747 B1 | 5/2001 | Lowe | |
| 6,335,467 B1 | 1/2002 | Englert | |
| 6,362,195 B1 | 3/2002 | Lowe | |
| 6,436,967 B1 | 8/2002 | Talley | |
| 6,462,036 B1 * | 10/2002 | Doyle et al. | 514/218 |
| 6,476,054 B1 | 11/2002 | Caldwell | |
| 6,498,255 B2 | 12/2002 | Villalobos | |
| 6,521,643 B1 | 2/2003 | Tomishima | |
| 6,528,529 B1 | 3/2003 | Brann | |
| 6,537,994 B2 | 3/2003 | Ashwell | |
| 6,555,537 B2 | 4/2003 | Bauman | |
| 6,555,690 B2 | 4/2003 | Johnson | |
| 6,583,282 B1 | 6/2003 | Zhang | |
| 6,610,688 B2 | 8/2003 | Liang | |
| 6,638,951 B1 | 10/2003 | Kato | |
| 6,774,233 B2 | 8/2004 | Zhang | |
| 6,844,354 B1 | 1/2005 | Iizuka | |
| 7,001,905 B2 | 2/2006 | Biwersi | |
| 7,012,078 B2 | 3/2006 | Lowe | |
| 7,169,952 B2 | 1/2007 | Smeltz | |
| 2001/0025105 A1 | 9/2001 | DeBernardis | |
| 2002/0013310 A1 | 1/2002 | Choi-Sledeski | |
| 2002/0099054 A1 | 7/2002 | Connor | |
| 2002/0177598 A1 | 11/2002 | Bauman | |
| 2003/0032657 A1 | 2/2003 | Brown | |
| 2003/0055012 A1 | 3/2003 | Carter | |
| 2003/0069287 A1 | 4/2003 | Talley | |
| 2003/0069418 A1 | 4/2003 | Aquila | |
| 2003/0096817 A1 | 5/2003 | Green | |
| 2003/0105161 A1 | 6/2003 | Birkinshaw | |
| 2003/0158194 A1 | 8/2003 | Druzgala | |
| 2003/0158205 A1 | 8/2003 | Bauman | |
| 2003/0166930 A1 | 9/2003 | Zhang | |
| 2003/0225036 A1 | 12/2003 | Kolesnikov | |
| 2003/0236293 A1 | 12/2003 | Seibert | |
| 2003/0236437 A1 | 12/2003 | Smeltz | |
| 2004/0002522 A1 | 1/2004 | Carter | |
| 2004/0009983 A1 | 1/2004 | Cox | |
| 2004/0030145 A1 | 2/2004 | Jendralla | |
| 2004/0053931 A1 | 3/2004 | Cox | |
| 2004/0058921 A1 | 3/2004 | Branch | |
| 2004/0058932 A1 | 3/2004 | Blumberg | |
| 2004/0072839 A1 | 4/2004 | Leonardi | |
| 2004/0106641 A1 | 6/2004 | Hofgen | |
| 2004/0167198 A1 | 8/2004 | Wrasidlo | |
| 2004/0186136 A1 | 9/2004 | Alken | |
| 2004/0209846 A1 | 10/2004 | Cuny | |
| 2004/0209879 A1 | 10/2004 | Gustafsson | |
| 2005/0004140 A1 | 1/2005 | Burns | |
| 2005/0026926 A1 | 2/2005 | Uragg | |
| 2005/0032852 A1 | 2/2005 | Carter | |
| 2005/0107493 A1 | 5/2005 | Shutske | |
| 2005/0209255 A1 * | 9/2005 | Jimenez et al. | 514/267 |
| 2005/0215526 A1 | 9/2005 | Hulme | |
| 2005/0215582 A1 | 9/2005 | Nielsen | |
| 2005/0261331 A1 | 11/2005 | Nielsen | |
| 2005/0267304 A1 | 12/2005 | Cox | |
| 2006/0030583 A1 | 2/2006 | Arnold | |
| 2006/0058315 A1 | 3/2006 | Barton | |
| 2006/0058340 A1 | 3/2006 | Ibrahim | |
| 2006/0128661 A1 | 6/2006 | Ebenbeck | |
| 2006/0128744 A1 | 6/2006 | Schechter | |
| 2006/0148811 A1 | 7/2006 | Li | |
| 2006/0160803 A1 | 7/2006 | Adams | |
| 2006/0211577 A1 | 9/2006 | Hamprecht | |
| 2006/0211678 A1 | 9/2006 | Ahmed | |
| 2006/0246099 A1 | 11/2006 | Cavezza | |
| 2006/0258700 A1 | 11/2006 | Hofgen | |
| 2006/0287309 A1 | 12/2006 | Clark | |
| 2006/0287310 A1 | 12/2006 | Clark | |
| 2007/0032519 A1 | 2/2007 | Zhang | |
| 2007/0043063 A1 | 2/2007 | Salituro | |
| 2007/0043068 A1 | 2/2007 | Arnold | |
| 2007/0060585 A1 | 3/2007 | Gallagher | |
| 2007/0072896 A1 | 3/2007 | Khan | |
| 2007/0072897 A1 | 3/2007 | Mahaney | |
| 2008/0076921 A1 | 3/2008 | Honigberg et al. | |

(56) References Cited

U.S. PATENT DOCUMENTS

FOREIGN PATENT DOCUMENTS

| EP | 0 015 750 | 9/1980 |
|---|---|---|
| EP | 0 288 563 | 11/1988 |
| FR | 2 172 752 | 10/1973 |
| GB | 1294763 | 11/1972 |
| JP | 1995041459 | 7/1993 |
| WO | WO 94/08711 | 4/1994 |
| WO | WO 03/104216 | 12/2003 |
| WO | WO 2004/046124 | 6/2004 |
| WO | WO 2005/037843 A1 * | 4/2005 |
| WO | WO 2005/037843 | 5/2005 |
| WO | WO 2006/034474 | 3/2006 |
| WO | WO 2006/127587 | 11/2006 |
| WO | WO 2006/131519 | 12/2006 |
| WO | WO 2007/076228 | 7/2007 |
| WO | WO 2007/084667 | 7/2007 |
| WO | WO 2007/088190 | 8/2007 |

OTHER PUBLICATIONS

Graux et al., "Cytogenetics and molecular genetics of T-cell acute lymphoblastic leukemia: from thymocyte to lymphoblast," *Leukemia* 20, 1496-1510, 2006.
Klemke et al., "New insights into the molecular biology and targeted therapy of cutaneous T-cell lymphomas," *JDDG* 4, 395-406, 2006.
Pathak & Singh, "Studies in Fluorinated Mannich Bases. Part 2: Synthesis and Biological Activity of Some New 3-Alkylaminopropiophenones," *Die Pharmazie* 35, 434, 1980.
Taylor & Nobles, "Some Ketonic Mannich Bases," *J. Am. Pharmaceutical Asssoc.* 49, 317-19, May 1960.
Weigel et al., "Stereoselective Photocyclization to 2-Aminocyclopropanols by Photolysis of β-Aminoketones and Oxidative Ring Opening to Enaminones," *Tetrahedron* 53, 7855-66, 1997.
Weiel et al., "The Influence of substituents on the Photochemical Generation and Stability of 2-Morpholinocyclopropanols," *Tetrahedron Letters* 34, 6737-6740, 1993.
Wissner et al., "Synthesis and Structure-Activity Relationships of 6,7-Disubstituted 4-Anilinoquinoline-3-carbonitriles. The Design of an Orally Active, Irreversible Inhibitor of the Tyrosine Kinase Activity of the Epidermal Growth Factor Receptor (EGFR) and the Human Epidermal Growth factor Receptor-2 (HER-2)," *J. Med. Chem.* 46, 49-63, 2003.
(No author) BLAST results for Bruton's tyrosine kinase (BTK), May 18, 2007, pp. 1-74.
(No author) BLAST results for interleukin-2 inducible tyrosine kinase (ITK), May 18, 2007, pp. 1-72.
Pelletier, "Certain ketonic Mannich bases derived from 1- and 2-acetonaphthone," *J. Organic Chem.* 17, 313-15, 1952.
Dauksas et al., "Synthesis and anti-inflammatory activity of acyl-substituted benzoxa- and benzodioxaheterocycles and their acyclic analogs," Chem. Abstracts accession No. 1987: 590332, 1987.
Fry, "The Mannich reaction," Chem. Abstracts accession No. 1945: 25445, 1945.
Ohtaka et al., "Benzylpiperazine derivatives. I. Syntheses and biological activities of 1-(2,3,4-trimethoxybenzyl)piperazine derivatives," Chem. Abstracts accession No. 1988:150421, 1988.
Taylor et al., "Synthesis of 2-aminonicotinamidees by Raney nickel cleavage of pyrazolo[3,4-b]pyridines," Chem. Abstracts accession No. 1960: 11425, 1960.
Weber et al., "A chemometric study of the 5-HT1A receptor affinities presented by arylpiperazine compounds," Chem. Abstracts. accession No. 2008:232006, 2008.
Zsolnai, "New fungistatic compounds. VI. Hydrazine derivatives and organic ases or their salts," Chem. Abstracts accession No. 1963: 5090, 1963.
Search report and written opinion for PCT/US2007/011974, Aug. 21, 2008, MannKind Corp.

* cited by examiner

FIG. 2

```
huITK    5  ILLEEQLIKKSQQKRRTSPSNFKVRFFVLTKASLAYFED--RHGKKRTLKGSIELSRIKC    62
            ++LE   +K+SQQK++TSP NFK R F+LT  L+Y+E     G++ + KGSI++ +I C
huBTK    4  VILESIFLKRSQQKKKTSPLNFKKRLFLLTVHKLSYYEYDFERGRRGSKKGSIDVEKITC    63

Query   63  VEIVKSD--------------------ISIPCHYKYPFQVVHDNYLLYVFAPDRESRQR   101
            VE V +                     ISI   + YPFQVV+D  LYVF+P  E R+R
Sbjct   64  VETVVPEKNPPPERQIPRRGEESSEMEQISIIERFPYPFQVVYDEGPLYVFSPTEELRKR   123

Query  102  WVLALKEETRNNNSLVPKYHPNFWMDGKWRCCSQLEKLATGCAQYDPTKNAS--------   153
            W+  LK   R N+ LV KYHP FW+DG++ CCSQ  K A GC Q     +N S
Sbjct  124  WIHQLKNVIRYNSDLVQKYHPCFWIDGQYLCCSQTAKNAMGC-QILENRNGSLKPGSSHR   182

Query  154  --KKPLPPTPEDNR-----------RPLWEPEETVVIALYDYQTNDPQELALRRNEEYC   199
              KKPLPPTPE+++              P+   E   V+ALYDY   + +L LR+ +EY
Sbjct  183  KTKKPLPPTPEEDQILKKPLPPEPAAAPVSTSELKKVVALYDYMPMNANDLQLRKGDEYF   242

Query  200  LLDSSEIHWWRVQDRNGHEGYVPSSYLVEKSPNNLETYEWYNKSISRDKAEKLLLDTGKE   259
            +L+ S + WWR +D+NG EGY+PS+Y+  E +   +++E YEWY+K ++R +AE+LL   GKE
Sbjct  243  ILEESNLPWWRARDKNGQEGYIPSNYVTE-AEDSIEMYEWYSKHMTRSQAEQLLKQEGKE   301

Query  260  GAFMVRDSRTAGTYTVSVFTKAVVSENNPCIKHYHIKETNDNPKRYYVAEKYVFDSIPLL   319
            G F+VRDS  AG YTVSVF K+   +     I+HY + T +  +YY+AEK++F +IP L
Sbjct  302  GGFIVRDSSKAGKYTVSVFAKST-GDPQGVIRHYVVCSTPQS--QYYLAEKHLFSTIPEL   358

Query  320  INYHQHNGGGLVTRLRYPVCFGRQKAPVTAGLRYGKWVIDPSELTFVQEIGSGQFGLVHL   379
            INYHQHN   GL++RL+YPV   + AP TAGL YG W IDP +LTF++E+G+GQFG+V
Sbjct  359  INYHQHNSAGLISRLKYPVSQQNKNAPSTAGLGYGSWEIDPKDLTFLKELGTGQFGVVKY   418

Query  380  GYWLNKDKVAIKTIREGAMSEEDFIEEAEVMMKLSHPKLVQLYGVCLEQAPICLVFEFME   439
            G W  +  VAIK I+EG+MSE++FIEEA+VMM LSH KLVQLYGVC +Q PI ++ E+M
Sbjct  419  GKWRGQYDVAIKMIKEGSMSEDEFIEEAKVMMNLSHEKLVQLYGVCTKQRPIFIITEYMA   478 huITK  440  HGCLSDYLRTQRGLFAAETLLGMCLDVCEGMAYLEEACVIHRDLAARNCLVGENQVIKVS   499
            +GCL +YLR  R F  + LL MC DVCE M YLE      +HRDLAARNCLV +  V+KVS
huBTK  479  NGCLLNYLREMRHRFQTQQLLEMCKDVCEAMEYLESKQFLHRDLAARNCLVNDQGVVKVS   538

Query  500  DFGMTRFVLDDQYTSSTGTKFPVKWASPEVFSFSRYSSKSDVWSFGVLMWEVFSEGKIPY   559
            DFG++R+VLDD+YTSS G+KFPV+W+ PEV   +S++SSKSD+W FGVLMWE++S GK+PY
Sbjct  539  DFGLSRYVLDDEYTSSVGSKFPVRWSPPEVLMYSKFSSKSDIWAFGVLMWEIYSLGKMPY   598

Query  560  ENRSNSEVVEDISTGFRLYKPRLASTHVYQIMNHCWKERPEDRPAFSRLLRQLAEIAE    617
            E  +NSE   E I+ G RLY+P LAS  VY IM  CW E+ ++RP F  LL  + ++ +
Sbjct  599  ERFTNSETAEHIAQGLRLYRPHLASEKVYTIMYSCWHEKADERPTFKILLSNILDVMD    656
```

FIG. 3

```
TK_Tec__BTK         LTFLKELGTGQFGVVKYGKWRG-----QYDVAIKMIKEGS    (SEQ ID NO:3)
TK_Tec__BMX         ITLLKELGSGQFGVVQLGKWKG-----QYDVAVKMIKEGS    (SEQ ID NO:4)
TK_Tec__TEC         LTFMRELGSGLFGVVRLGKWRA-----QYKVAIKAIREGA    (SEQ ID NO:5)
TK_Tec__TXK         LAFIKEIGSGQFGVVHLGEWRS-----HIQVAIKAINEGS    (SEQ ID NO:6)
TK_Tec__ITK         LTFVQEIGSGQFGLVHLGYWLN-----KDKVAIKTIREGA    (SEQ ID NO:7)
TK_Src__BLK         LRLVRKLGSGQFGEVWMGYYKN-----NMKVAIKTLKEGT    (SEQ ID NO:8)
TK_EGFR__EGFR       FKKIKVLGSGAFGTVYKGLWIPEGEKVKIPVAIKELREAT    (SEQ ID NO:9)
TK_EGFR__HER2_ErbB2 LRKVKVLGSGAFGTVYKGIWIPDGENVKIPVAIKVLRENT    (SEQ ID NO:10)
TK_EGFR__HER4_ErbB4 LKRVKVLGSGAFGTVYKGIWVPEGETVKIPVAIKILNETT    (SEQ ID NO:11)
TK_JakA__JAK3       LKYISQLGKGNFGSVELCRYDPLAHNTGALVAVKQLQHSG    (SEQ ID NO:12)
TK_Tec__BTK         --MSEDEFIEEAKVMMNLSHEKLVQLYGVCTKQR-PIFI    (SEQ ID NO:13)
TK_Tec__BMX         --MSEDEFFQEAQTMMKLSHPKLVKFYGVCSKEY-PIYI    (SEQ ID NO:14)
TK_Tec__TEC         --MCEEDFIEEAKVMMKLTHPKLVQLYGVCTQQK-PIYI    (SEQ ID NO:15)
TK_Tec__TXK         --MSEEDFIEEAKVMMKLSHSKLVQLYGVCIQRK-PLYI    (SEQ ID NO:16)
TK_Tec__ITK         --MSEEDFIEEAEVMMKLSHPKLVQLYGVCLEQA-PICL    (SEQ ID NO:17)
TK_Src__BLK         --MSPEAFLGEANVMKALQHERLVRLYAVVTKE---PIYI   (SEQ ID NO:18)
TK_EGFR__EGFR       SPKANKEILDEAYVMASVDNPHVCRLLGICLTS---TVQL    (SEQ ID NO:19)
TK_EGFR__HER2_ErbB2 SPKANKEILDEAYVMAGVGSPYVSRLLGICLTS---TVQL    (SEQ ID NO:20)
TK_EGFR__HER4_ErbB4 GPKANVEFMDEALIMASMDHPHLVRLLGVCLSP---TIQL    (SEQ ID NO:21)
TK_JakA__JAK3       -PDQQRDFQREIQILKALHSDFIVKYRGVSYGPGRPELRL    (SEQ ID NO:22)
TK_Tec__BTK         ITEYMANGCLLNYLREMRH-RFQTQQLLEMCKDV------   (SEQ ID NO:23)
TK_Tec__BMX         VTEYISNGCLLNYLRSHGK-GLEPSQLLEMCYDV------   (SEQ ID NO:24)
TK_Tec__TEC         VTEFMERGCLLNFLRQRQG-HFSRDVLLSMCQDV------   (SEQ ID NO:25)
TK_Tec__TXK         VTEFMENGCLLNYLRENKG-KLRKEMLLSVCQDI------   (SEQ ID NO:26)
TK_Tec__ITK         VFEFMEHGCLSDYLRTQRG-LFAAETLLGMCLDV------   (SEQ ID NO:27)
TK_Src__BLK         VTEYMARGCLLDFLKTDEGSRLSLPRLIDMSAQIAEGMAY   (SEQ ID NO:28)
TK_EGFR__EGFR       ITQLMPFGCLLDYVREHKD-NIGSQYLLNWCVQIAKGMNY   (SEQ ID NO:29)
TK_EGFR__HER2_ErbB2 VTQLMPYGCLLDHVRENRG-RLGSQDLLNWCMQIAKGMSY   (SEQ ID NO:30)
TK_EGFR__HER4_ErbB4 VTQLMPHGCLLEYVHEHKD-NIGSQLLLNWCVQIAKGMMY   (SEQ ID NO:31)
TK_JakA__JAK3       VMEYLPSGCLRDFLQRHRA-RLDASRLLLYSSQICKGMEY   (SEQ ID NO:32)
TK_Tec__BTK         -----FLHRDLAARNCLVNDQGVVKVSDFGLSRYVLDDEY   (SEQ ID NO:33)
TK_Tec__BMX         -----FIHRDLAARNCLVDRDLCVKVSDFGMTRYVLDDQY   (SEQ ID NO:34)
TK_Tec__TEC         -----FIHRDLAARNCLVSEAGVVKVSDFGMARYFLDDQY   (SEQ ID NO:35)
TK_Tec__TXK         -----YIHRDLAARNCLVSSTCIVKISDFGMTRYVLDDEY   (SEQ ID NO:36)
TK_Tec__ITK         -----VIHRDLAARNCLVGENQVIKVSDFGMTRFVLDDQY   (SEQ ID NO:37)
TK_Src__BLK         IERMNSIHRDLRAANILVSEALCCKIADFGLAR-IIDSEY   (SEQ ID NO:38)
TK_EGFR__EGFR       LEDRRLVHRDLAARNVLVKTPQHVKITDFGLAKLLGAEEK   (SEQ ID NO:39)
TK_EGFR__HER2_ErbB2 LEDVRLVHRDLAARNVLVKSPNHVKITDFGLARLLDIDET   (SEQ ID NO:40)
TK_EGFR__HER4_ErbB4 LEERRLVHRDLAARNVLVKSPNHVKITDFGLARLLEGDEK   (SEQ ID NO:41)
TK_JakA__JAK3       LGSRRCVHRDLAARNILVESEAHVKIADFGLAKLLPLDKD   (SEQ ID NO:42)
```

SEQUENCE LISTING

<160> NUMBER OF SEQ ID NOS: 42

<210> SEQ ID NO 1
<211> LENGTH: 620
<212> TYPE: PRT
<213> ORGANISM: Homo sapiens

<400> SEQUENCE: 1

```
Met Asn Asn Phe Ile Leu Leu Glu Glu Gln Leu Ile Lys Lys Ser Gln
 1               5                  10                  15

Gln Lys Arg Arg Thr Ser Pro Ser Asn Phe Lys Val Arg Phe Phe Val
            20                  25                  30

Leu Thr Lys Ala Ser Leu Ala Tyr Phe Glu Asp Arg His Gly Lys Lys
        35                  40                  45

Arg Thr Leu Lys Gly Ser Ile Glu Leu Ser Arg Ile Lys Cys Val Glu
    50                  55                  60

Ile Val Lys Ser Asp Ile Ser Ile Pro Cys His Tyr Lys Tyr Pro Phe
65                  70                  75                  80

Gln Val Val His Asp Asn Tyr Leu Leu Tyr Val Phe Ala Pro Asp Arg
                85                  90                  95

Glu Ser Arg Gln Arg Trp Val Leu Ala Leu Lys Glu Glu Thr Arg Asn
            100                 105                 110
```

Asn Asn Ser Leu Val Pro Lys Tyr His Pro Asn Phe Trp Met Asp Gly
            115                 120                 125

Lys Trp Arg Cys Cys Ser Gln Leu Glu Lys Leu Ala Thr Gly Cys Ala
    130                 135                 140

Gln Tyr Asp Pro Thr Lys Asn Ala Ser Lys Lys Pro Leu Pro Pro Thr
145                 150                 155                 160

Pro Glu Asp Asn Arg Arg Pro Leu Trp Glu Pro Glu Thr Val Val
                165                 170                 175

Ile Ala Leu Tyr Asp Tyr Gln Thr Asn Asp Pro Gln Glu Leu Ala Leu
            180                 185                 190

Arg Arg Asn Glu Glu Tyr Cys Leu Leu Asp Ser Ser Glu Ile His Trp
    195                 200                 205

Trp Arg Val Gln Asp Arg Asn Gly His Glu Gly Tyr Val Pro Ser Ser
    210                 215                 220

Tyr Leu Val Glu Lys Ser Pro Asn Asn Leu Glu Thr Tyr Glu Trp Tyr
225                 230                 235                 240

Asn Lys Ser Ile Ser Arg Asp Lys Ala Glu Lys Leu Leu Leu Asp Thr
            245                 250                 255

Gly Lys Glu Gly Ala Phe Met Val Arg Asp Ser Arg Thr Ala Gly Thr
    260                 265                 270

Tyr Thr Val Ser Val Phe Thr Lys Ala Val Val Ser Glu Asn Asn Pro
    275                 280                 285

Cys Ile Lys His Tyr His Ile Lys Glu Thr Asn Asp Asn Pro Lys Arg
    290                 295                 300

Tyr Tyr Val Ala Glu Lys Tyr Val Phe Asp Ser Ile Pro Leu Leu Ile
305                 310                 315                 320

Asn Tyr His Gln His Asn Gly Gly Leu Val Thr Arg Leu Arg Tyr
            325                 330                 335

Pro Val Cys Phe Gly Arg Gln Lys Ala Pro Val Thr Ala Gly Leu Arg
            340                 345                 350

Tyr Gly Lys Trp Val Ile Asp Pro Ser Glu Leu Thr Phe Val Gln Glu
    355                 360                 365

Ile Gly Ser Gly Gln Phe Gly Leu Val His Leu Gly Tyr Trp Leu Asn
    370                 375                 380

Lys Asp Lys Val Ala Ile Lys Thr Ile Arg Glu Gly Ala Met Ser Glu
385                 390                 395                 400

Glu Asp Phe Ile Glu Glu Ala Glu Val Met Met Lys Leu Ser His Pro
            405                 410                 415

Lys Leu Val Gln Leu Tyr Gly Val Cys Leu Glu Gln Ala Pro Ile Cys
    420                 425                 430

Leu Val Phe Glu Phe Met Glu His Gly Cys Leu Ser Asp Tyr Leu Arg
    435                 440                 445

Thr Gln Arg Gly Leu Phe Ala Ala Glu Thr Leu Leu Gly Met Cys Leu
    450                 455                 460

Asp Val Cys Glu Gly Met Ala Tyr Leu Glu Glu Ala Cys Val Ile His
465                 470                 475                 480

Arg Asp Leu Ala Ala Arg Asn Cys Leu Val Gly Glu Asn Gln Val Ile
            485                 490                 495

Lys Val Ser Asp Phe Gly Met Thr Arg Phe Val Leu Asp Asp Gln Tyr
            500                 505                 510

Thr Ser Ser Thr Gly Thr Lys Phe Pro Val Lys Trp Ala Ser Pro Glu
    515                 520                 525

Val Phe Ser Phe Ser Arg Tyr Ser Ser Lys Ser Asp Val Trp Ser Phe

```
                    530                 535                 540
Gly Val Leu Met Trp Glu Val Phe Ser Glu Gly Lys Ile Pro Tyr Glu
545                 550                 555                 560

Asn Arg Ser Asn Ser Glu Val Val Glu Asp Ile Ser Thr Gly Phe Arg
                565                 570                 575

Leu Tyr Lys Pro Arg Leu Ala Ser Thr His Val Tyr Gln Ile Met Asn
            580                 585                 590

His Cys Trp Lys Glu Arg Pro Glu Asp Arg Pro Ala Phe Ser Arg Leu
        595                 600                 605

Leu Arg Gln Leu Ala Glu Ile Ala Glu Ser Gly Leu
    610                 615                 620

<210> SEQ ID NO 2
<211> LENGTH: 659
<212> TYPE: PRT
<213> ORGANISM: Homo sapiens

<400> SEQUENCE: 2

Met Ala Ala Val Ile Leu Glu Ser Ile Phe Leu Lys Arg Ser Gln Gln
1               5                   10                  15

Lys Lys Lys Thr Ser Pro Leu Asn Phe Lys Lys Arg Leu Phe Leu Leu
            20                  25                  30

Thr Val His Lys Leu Ser Tyr Tyr Glu Tyr Asp Phe Glu Arg Gly Arg
        35                  40                  45

Arg Gly Ser Lys Lys Gly Ser Ile Asp Val Glu Lys Ile Thr Cys Val
    50                  55                  60

Glu Thr Val Val Pro Glu Lys Asn Pro Pro Glu Arg Gln Ile Pro
65                  70                  75                  80

Arg Arg Gly Glu Glu Ser Ser Glu Met Glu Gln Ile Ser Ile Ile Glu
                85                  90                  95

Arg Phe Pro Tyr Pro Phe Gln Val Val Tyr Asp Glu Gly Pro Leu Tyr
            100                 105                 110

Val Phe Ser Pro Thr Glu Glu Leu Arg Lys Arg Trp Ile His Gln Leu
        115                 120                 125

Lys Asn Val Ile Arg Tyr Asn Ser Asp Leu Val Gln Lys Tyr His Pro
    130                 135                 140

Cys Phe Trp Ile Asp Gly Gln Tyr Leu Cys Cys Ser Gln Thr Ala Lys
145                 150                 155                 160

Asn Ala Met Gly Cys Gln Ile Leu Glu Asn Arg Asn Gly Ser Leu Lys
                165                 170                 175

Pro Gly Ser Ser His Arg Lys Thr Lys Lys Pro Leu Pro Pro Thr Pro
            180                 185                 190

Glu Glu Asp Gln Ile Leu Lys Lys Pro Leu Pro Pro Glu Pro Ala Ala
        195                 200                 205

Ala Pro Val Ser Thr Ser Glu Leu Lys Lys Val Val Ala Leu Tyr Asp
    210                 215                 220

Tyr Met Pro Met Asn Ala Asn Asp Leu Gln Leu Arg Lys Gly Asp Glu
225                 230                 235                 240

Tyr Phe Ile Leu Glu Glu Ser Asn Leu Pro Trp Trp Arg Ala Arg Asp
                245                 250                 255

Lys Asn Gly Gln Glu Gly Tyr Ile Pro Ser Asn Tyr Val Thr Glu Ala
            260                 265                 270

Glu Asp Ser Ile Glu Met Tyr Glu Trp Tyr Ser Lys His Met Thr Arg
        275                 280                 285

Ser Gln Ala Glu Gln Leu Leu Lys Gln Glu Gly Lys Glu Gly Gly Phe
```

```
                290                 295                 300
Ile Val Arg Asp Ser Ser Lys Ala Gly Lys Tyr Thr Val Ser Val Phe
305                 310                 315                 320

Ala Lys Ser Thr Gly Asp Pro Gln Gly Val Ile Arg His Tyr Val Val
                325                 330                 335

Cys Ser Thr Pro Gln Ser Gln Tyr Tyr Leu Ala Glu Lys His Leu Phe
                340                 345                 350

Ser Thr Ile Pro Glu Leu Ile Asn Tyr His Gln His Asn Ser Ala Gly
                355                 360                 365

Leu Ile Ser Arg Leu Lys Tyr Pro Val Ser Gln Gln Asn Lys Asn Ala
370                 375                 380

Pro Ser Thr Ala Gly Leu Gly Tyr Gly Ser Trp Glu Ile Asp Pro Lys
385                 390                 395                 400

Asp Leu Thr Phe Leu Lys Glu Leu Gly Thr Gly Gln Phe Gly Val Val
                405                 410                 415

Lys Tyr Gly Lys Trp Arg Gly Gln Tyr Asp Val Ala Ile Lys Met Ile
                420                 425                 430

Lys Glu Gly Ser Met Ser Glu Asp Glu Phe Ile Glu Glu Ala Lys Val
                435                 440                 445

Met Met Asn Leu Ser His Glu Lys Leu Val Gln Leu Tyr Gly Val Cys
450                 455                 460

Thr Lys Gln Arg Pro Ile Phe Ile Ile Thr Glu Tyr Met Ala Asn Gly
465                 470                 475                 480

Cys Leu Leu Asn Tyr Leu Arg Glu Met Arg His Arg Phe Gln Thr Gln
                485                 490                 495

Gln Leu Leu Glu Met Cys Lys Asp Val Cys Glu Ala Met Glu Tyr Leu
                500                 505                 510

Glu Ser Lys Gln Phe Leu His Arg Asp Leu Ala Ala Arg Asn Cys Leu
                515                 520                 525

Val Asn Asp Gln Gly Val Val Lys Val Ser Asp Phe Gly Leu Ser Arg
530                 535                 540

Tyr Val Leu Asp Asp Glu Tyr Thr Ser Ser Val Gly Ser Lys Phe Pro
545                 550                 555                 560

Val Arg Trp Ser Pro Pro Glu Val Leu Met Tyr Ser Lys Phe Ser Ser
                565                 570                 575

Lys Ser Asp Ile Trp Ala Phe Gly Val Leu Met Trp Glu Ile Tyr Ser
                580                 585                 590

Leu Gly Lys Met Pro Tyr Glu Arg Phe Thr Asn Ser Glu Thr Ala Glu
                595                 600                 605

His Ile Ala Gln Gly Leu Arg Leu Tyr Arg Pro His Leu Ala Ser Glu
                610                 615                 620

Lys Val Tyr Thr Ile Met Tyr Ser Cys Trp His Glu Lys Ala Asp Glu
625                 630                 635                 640

Arg Pro Thr Phe Lys Ile Leu Leu Ser Asn Ile Leu Asp Val Met Asp
                645                 650                 655

Glu Glu Ser

<210> SEQ ID NO 3
 <211> LENGTH: 35
<212> TYPE: PRT
<213> ORGANISM: Homo sapiens

<400> SEQUENCE: 3

Leu Thr Phe Leu Lys Glu Leu Gly Thr Gly Gln Phe Gly Val Val Lys
1               5                   10                  15
```

```
Tyr Gly Lys Trp Arg Gly Gln Tyr Asp Val Ala Ile Lys Met Ile Lys
            20                  25                  30

Glu Gly Ser
        35

<210> SEQ ID NO 4
<211> LENGTH: 35
<212> TYPE: PRT
<213> ORGANISM: Homo sapiens

<400> SEQUENCE: 4

Ile Thr Leu Leu Lys Glu Leu Gly Ser Gly Gln Phe Gly Val Val Gln
  1               5                  10                  15

Leu Gly Lys Trp Lys Gly Gln Tyr Asp Val Ala Val Lys Met Ile Lys
            20                  25                  30

Glu Gly Ser
        35

<210> SEQ ID NO 5
<211> LENGTH: 35
<212> TYPE: PRT
<213> ORGANISM: Homo sapiens

<400> SEQUENCE: 5

Leu Thr Phe Met Arg Glu Leu Gly Ser Gly Leu Phe Gly Val Val Arg
  1               5                  10                  15

Leu Gly Lys Trp Arg Ala Gln Tyr Lys Val Ala Ile Lys Ala Ile Arg
            20                  25                  30

Glu Gly Ala
        35

<210> SEQ ID NO 6
<211> LENGTH: 35
<212> TYPE: PRT
<213> ORGANISM: Homo sapiens

<400> SEQUENCE: 6

Leu Ala Phe Ile Lys Glu Ile Gly Ser Gly Gln Phe Gly Val Val His
  1               5                  10                  15

Leu Gly Glu Trp Arg Ser His Ile Gln Val Ala Ile Lys Ala Ile Asn
            20                  25                  30

Glu Gly Ser
        35

<210> SEQ ID NO 7
<211> LENGTH: 35
<212> TYPE: PRT
<213> ORGANISM: Homo sapiens

<400> SEQUENCE: 7

Leu Thr Phe Val Gln Glu Ile Gly Ser Gly Gln Phe Gly Leu Val His
  1               5                  10                  15

Leu Gly Tyr Trp Leu Asn Lys Asp Lys Val Ala Ile Lys Thr Ile Arg
            20                  25                  30

Glu Gly Ala
        35

<210> SEQ ID NO 8
<211> LENGTH: 35
<212> TYPE: PRT
<213> ORGANISM: Homo sapiens
```

<400> SEQUENCE: 8

Leu Arg Leu Val Arg Lys Leu Gly Ser Gly Gln Phe Gly Glu Val Trp
1               5                   10                  15

Met Gly Tyr Tyr Lys Asn Asn Met Lys Val Ala Ile Lys Thr Leu Lys
            20                  25                  30

Glu Gly Thr
        35

<210> SEQ ID NO 9
<211> LENGTH: 40
<212> TYPE: PRT
<213> ORGANISM: Homo sapiens

<400> SEQUENCE: 9

Phe Lys Lys Ile Lys Val Leu Gly Ser Gly Ala Phe Gly Thr Val Tyr
1               5                   10                  15

Lys Gly Leu Trp Ile Pro Glu Gly Glu Lys Val Lys Ile Pro Val Ala
            20                  25                  30

Ile Lys Glu Leu Arg Glu Ala Thr
        35                  40

<210> SEQ ID NO 10
<211> LENGTH: 40
<212> TYPE: PRT
<213> ORGANISM: Homo sapiens

<400> SEQUENCE: 10

Leu Arg Lys Val Lys Val Leu Gly Ser Gly Ala Phe Gly Thr Val Tyr
1               5                   10                  15

Lys Gly Ile Trp Ile Pro Asp Gly Glu Asn Val Lys Ile Pro Val Ala
            20                  25                  30

Ile Lys Val Leu Arg Glu Asn Thr
        35                  40

<210> SEQ ID NO 11
<211> LENGTH: 40
<212> TYPE: PRT
<213> ORGANISM: Homo sapiens

<400> SEQUENCE: 11

Leu Lys Arg Val Lys Val Leu Gly Ser Gly Ala Phe Gly Thr Val Tyr
1               5                   10                  15

Lys Gly Ile Trp Val Pro Glu Gly Glu Thr Val Lys Ile Pro Val Ala
            20                  25                  30

Ile Lys Ile Leu Asn Glu Thr Thr
        35                  40

<210> SEQ ID NO 12
<211> LENGTH: 40
<212> TYPE: PRT
<213> ORGANISM: Homo sapiens

<400> SEQUENCE: 12

Leu Lys Tyr Ile Ser Gln Leu Gly Lys Gly Asn Phe Gly Ser Val Glu
1               5                   10                  15

Leu Cys Arg Tyr Asp Pro Leu Ala His Asn Thr Gly Ala Leu Val Ala
            20                  25                  30

Val Lys Gln Leu Gln His Ser Gly
        35                  40

<210> SEQ ID NO 13
<211> LENGTH: 36
<212> TYPE: PRT
<213> ORGANISM: Homo sapiens

<400> SEQUENCE: 13

Met Ser Glu Asp Glu Phe Ile Glu Glu Ala Lys Val Met Met Asn Leu
1               5                   10                  15

Ser His Glu Lys Leu Val Gln Leu Tyr Gly Val Cys Thr Lys Gln Arg
            20                  25                  30

Pro Ile Phe Ile
        35

<210> SEQ ID NO 14
<211> LENGTH: 36
<212> TYPE: PRT
<213> ORGANISM: Homo sapiens

<400> SEQUENCE: 14

Met Ser Glu Asp Glu Phe Phe Gln Glu Ala Gln Thr Met Met Lys Leu
1               5                   10                  15

Ser His Pro Lys Leu Val Lys Phe Tyr Gly Val Cys Ser Lys Glu Tyr
            20                  25                  30

Pro Ile Tyr Ile
        35

<210> SEQ ID NO 15
<211> LENGTH: 36
<212> TYPE: PRT
<213> ORGANISM: Homo sapiens

<400> SEQUENCE: 15

Met Cys Glu Glu Asp Phe Ile Glu Glu Ala Lys Val Met Met Lys Leu
1               5                   10                  15

Thr His Pro Lys Leu Val Gln Leu Tyr Gly Val Cys Thr Gln Gln Lys
            20                  25                  30

Pro Ile Tyr Ile
        35

<210> SEQ ID NO 16
<211> LENGTH: 36
<212> TYPE: PRT
<213> ORGANISM: Homo sapiens

<400> SEQUENCE: 16

Met Ser Glu Glu Asp Phe Ile Glu Glu Ala Lys Val Met Met Lys Leu
1               5                   10                  15

Ser His Ser Lys Leu Val Gln Leu Tyr Gly Val Cys Ile Gln Arg Lys
            20                  25                  30

Pro Leu Tyr Ile
        35

<210> SEQ ID NO 17
<211> LENGTH: 36
<212> TYPE: PRT
<213> ORGANISM: Homo sapiens

<400> SEQUENCE: 17

Met Ser Glu Glu Asp Phe Ile Glu Glu Ala Glu Val Met Met Lys Leu
1               5                   10                  15

Ser His Pro Lys Leu Val Gln Leu Tyr Gly Val Cys Leu Glu Gln Ala

```
                    20                  25                  30

Pro Ile Cys Leu
            35

<210> SEQ ID NO 18
<211> LENGTH: 35
<212> TYPE: PRT
<213> ORGANISM: Homo sapiens

<400> SEQUENCE: 18

Met Ser Pro Glu Ala Phe Leu Gly Glu Ala Asn Val Met Lys Ala Leu
 1               5                  10                  15

Gln His Glu Arg Leu Val Arg Leu Tyr Ala Val Val Thr Lys Glu Pro
                20                  25                  30

Ile Tyr Ile
            35

<210> SEQ ID NO 19
<211> LENGTH: 37
<212> TYPE: PRT
<213> ORGANISM: Homo sapiens

<400> SEQUENCE: 19

Ser Pro Lys Ala Asn Lys Glu Ile Leu Asp Glu Ala Tyr Val Met Ala
 1               5                  10                  15

Ser Val Asp Asn Pro His Val Cys Arg Leu Leu Gly Ile Cys Leu Thr
                20                  25                  30

Ser Thr Val Gln Leu
            35

<210> SEQ ID NO 20
<211> LENGTH: 37
<212> TYPE: PRT
<213> ORGANISM: Homo sapiens

<400> SEQUENCE: 20

Ser Pro Lys Ala Asn Lys Glu Ile Leu Asp Glu Ala Tyr Val Met Ala
 1               5                  10                  15

Gly Val Gly Ser Pro Tyr Val Ser Arg Leu Leu Gly Ile Cys Leu Thr
                20                  25                  30

Ser Thr Val Gln Leu
            35

<210> SEQ ID NO 21
<211> LENGTH: 37
<212> TYPE: PRT
<213> ORGANISM: Homo sapiens

<400> SEQUENCE: 21

Gly Pro Lys Ala Asn Val Glu Phe Met Asp Glu Ala Leu Ile Met Ala
 1               5                  10                  15

Ser Met Asp His Pro His Leu Val Arg Leu Leu Gly Val Cys Leu Ser
                20                  25                  30

Pro Thr Ile Gln Leu
            35

<210> SEQ ID NO 22
<211> LENGTH: 39
<212> TYPE: PRT
<213> ORGANISM: Homo sapiens

<400> SEQUENCE: 22
```

Pro Asp Gln Gln Arg Asp Phe Gln Arg Glu Ile Gln Ile Leu Lys Ala
1               5                   10                  15

Leu His Ser Asp Phe Ile Val Lys Tyr Arg Gly Val Ser Tyr Gly Pro
            20                  25                  30

Gly Arg Pro Glu Leu Arg Leu
            35

<210> SEQ ID NO 23
<211> LENGTH: 33
<212> TYPE: PRT
<213> ORGANISM: Homo sapiens

<400> SEQUENCE: 23

Ile Thr Glu Tyr Met Ala Asn Gly Cys Leu Leu Asn Tyr Leu Arg Glu
1               5                   10                  15

Met Arg His Arg Phe Gln Thr Gln Gln Leu Leu Glu Met Cys Lys Asp
            20                  25                  30

Val

<210> SEQ ID NO 24
<211> LENGTH: 33
<212> TYPE: PRT
<213> ORGANISM: Homo sapiens

<400> SEQUENCE: 24

Val Thr Glu Tyr Ile Ser Asn Gly Cys Leu Leu Asn Tyr Leu Arg Ser
1               5                   10                  15

His Gly Lys Gly Leu Glu Pro Ser Gln Leu Leu Glu Met Cys Tyr Asp
            20                  25                  30

Val

<210> SEQ ID NO 25
<211> LENGTH: 33
<212> TYPE: PRT
<213> ORGANISM: Homo sapiens

<400> SEQUENCE: 25

Val Thr Glu Phe Met Glu Arg Gly Cys Leu Leu Asn Phe Leu Arg Gln
1               5                   10                  15

Arg Gln Gly His Phe Ser Arg Asp Val Leu Leu Ser Met Cys Gln Asp
            20                  25                  30

Val

<210> SEQ ID NO 26
<211> LENGTH: 33
<212> TYPE: PRT
<213> ORGANISM: Homo sapiens

<400> SEQUENCE: 26

Val Thr Glu Phe Met Glu Asn Gly Cys Leu Leu Asn Tyr Leu Arg Glu
1               5                   10                  15

Asn Lys Gly Lys Leu Arg Lys Glu Met Leu Leu Ser Val Cys Gln Asp
            20                  25                  30

Ile

<210> SEQ ID NO 27
<211> LENGTH: 33
<212> TYPE: PRT
<213> ORGANISM: Homo sapiens

```
<400> SEQUENCE: 27

Val Phe Glu Phe Met Glu His Gly Cys Leu Ser Asp Tyr Leu Arg Thr
 1               5                  10                  15

Gln Arg Gly Leu Phe Ala Ala Glu Thr Leu Leu Gly Met Cys Leu Asp
                20                  25                  30

Val

<210> SEQ ID NO 28
<211> LENGTH: 40
<212> TYPE: PRT
<213> ORGANISM: Homo sapiens

<400> SEQUENCE: 28

Val Thr Glu Tyr Met Ala Arg Gly Cys Leu Leu Asp Phe Leu Lys Thr
 1               5                  10                  15

Asp Glu Gly Ser Arg Leu Ser Leu Pro Arg Leu Ile Asp Met Ser Ala
                20                  25                  30

Gln Ile Ala Glu Gly Met Ala Tyr
                35                  40

<210> SEQ ID NO 29
<211> LENGTH: 39
<212> TYPE: PRT
<213> ORGANISM: Homo sapiens

<400> SEQUENCE: 29

Ile Thr Gln Leu Met Pro Phe Gly Cys Leu Leu Asp Tyr Val Arg Glu
 1               5                  10                  15

His Lys Asp Asn Ile Gly Ser Gln Tyr Leu Leu Asn Trp Cys Val Gln
                20                  25                  30

Ile Ala Lys Gly Met Asn Tyr
                35

<210> SEQ ID NO 30
<211> LENGTH: 39
<212> TYPE: PRT
<213> ORGANISM: Homo sapiens

<400> SEQUENCE: 30

Val Thr Gln Leu Met Pro Tyr Gly Cys Leu Leu Asp His Val Arg Glu
 1               5                  10                  15

Asn Arg Gly Arg Leu Gly Ser Gln Asp Leu Leu Asn Trp Cys Met Gln
                20                  25                  30

Ile Ala Lys Gly Met Ser Tyr
                35

<210> SEQ ID NO 31
<211> LENGTH: 39
<212> TYPE: PRT
<213> ORGANISM: Homo sapiens

<400> SEQUENCE: 31

Val Thr Gln Leu Met Pro His Gly Cys Leu Leu Glu Tyr Val His Glu
 1               5                  10                  15

His Lys Asp Asn Ile Gly Ser Gln Leu Leu Leu Asn Trp Cys Val Gln
                20                  25                  30

Ile Ala Lys Gly Met Met Tyr
                35

<210> SEQ ID NO 32
```

```
<211> LENGTH: 39
<212> TYPE: PRT
<213> ORGANISM: Homo sapiens

<400> SEQUENCE: 32

Val Met Glu Tyr Leu Pro Ser Gly Cys Leu Arg Asp Phe Leu Gln Arg
 1               5                  10                  15

His Arg Ala Arg Leu Asp Ala Ser Arg Leu Leu Leu Tyr Ser Ser Gln
            20                  25                  30

Ile Cys Lys Gly Met Glu Tyr
            35

<210> SEQ ID NO 33
<211> LENGTH: 35
<212> TYPE: PRT
<213> ORGANISM: Homo sapiens

<400> SEQUENCE: 33

Phe Leu His Arg Asp Leu Ala Ala Arg Asn Cys Leu Val Asn Asp Gln
 1               5                  10                  15

Gly Val Val Lys Val Ser Asp Phe Gly Leu Ser Arg Tyr Val Leu Asp
            20                  25                  30

Asp Glu Tyr
        35

<210> SEQ ID NO 34
<211> LENGTH: 35
<212> TYPE: PRT
<213> ORGANISM: Homo sapiens

<400> SEQUENCE: 34

Phe Ile His Arg Asp Leu Ala Ala Arg Asn Cys Leu Val Asp Arg Asp
 1               5                  10                  15

Leu Cys Val Lys Val Ser Asp Phe Gly Met Thr Arg Tyr Val Leu Asp
            20                  25                  30

Asp Gln Tyr
        35

<210> SEQ ID NO 35
<211> LENGTH: 35
<212> TYPE: PRT
<213> ORGANISM: Homo sapiens

<400> SEQUENCE: 35

Phe Ile His Arg Asp Leu Ala Ala Arg Asn Cys Leu Val Ser Glu Ala
 1               5                  10                  15

Gly Val Val Lys Val Ser Asp Phe Gly Met Ala Arg Tyr Phe Leu Asp
            20                  25                  30

Asp Gln Tyr
        35

<210> SEQ ID NO 36
<211> LENGTH: 35
<212> TYPE: PRT
<213> ORGANISM: Homo sapiens

<400> SEQUENCE: 36

Tyr Ile His Arg Asp Leu Ala Ala Arg Asn Cys Leu Val Ser Ser Thr
 1               5                  10                  15

Cys Ile Val Lys Ile Ser Asp Phe Gly Met Thr Arg Tyr Val Leu Asp
            20                  25                  30
```

```
Asp Glu Tyr
        35

<210> SEQ ID NO 37
<211> LENGTH: 35
<212> TYPE: PRT
<213> ORGANISM: Homo sapiens

<400> SEQUENCE: 37

Val Ile His Arg Asp Leu Ala Ala Arg Asn Cys Leu Val Gly Glu Asn
 1               5                  10                  15

Gln Val Ile Lys Val Ser Asp Phe Gly Met Thr Arg Phe Val Leu Asp
            20                  25                  30

Asp Gln Tyr
        35

<210> SEQ ID NO 38
<211> LENGTH: 39
<212> TYPE: PRT
<213> ORGANISM: Homo sapiens

<400> SEQUENCE: 38

Ile Glu Arg Met Asn Ser Ile His Arg Asp Leu Arg Ala Ala Asn Ile
 1               5                  10                  15

Leu Val Ser Glu Ala Leu Cys Cys Lys Ile Ala Asp Phe Gly Leu Ala
            20                  25                  30

Arg Ile Ile Asp Ser Glu Tyr
        35

<210> SEQ ID NO 39
<211> LENGTH: 40
<212> TYPE: PRT
<213> ORGANISM: Homo sapiens

<400> SEQUENCE: 39

Leu Glu Asp Arg Arg Leu Val His Arg Asp Leu Ala Ala Arg Asn Val
 1               5                  10                  15

Leu Val Lys Thr Pro Gln His Val Lys Ile Thr Asp Phe Gly Leu Ala
            20                  25                  30

Lys Leu Leu Gly Ala Glu Glu Lys
        35                  40

<210> SEQ ID NO 40
<211> LENGTH: 40
<212> TYPE: PRT
<213> ORGANISM: Homo sapiens

<400> SEQUENCE: 40

Leu Glu Asp Val Arg Leu Val His Arg Asp Leu Ala Ala Arg Asn Val
 1               5                  10                  15

Leu Val Lys Ser Pro Asn His Val Lys Ile Thr Asp Phe Gly Leu Ala
            20                  25                  30

Arg Leu Leu Asp Ile Asp Glu Thr
        35                  40

<210> SEQ ID NO 41
<211> LENGTH: 40
<212> TYPE: PRT
<213> ORGANISM: Homo sapiens

<400> SEQUENCE: 41

Leu Glu Glu Arg Arg Leu Val His Arg Asp Leu Ala Ala Arg Asn Val
```

```
                1               5                  10                 15
Leu Val Lys Ser Pro Asn His Val Lys Ile Thr Asp Phe Gly Leu Ala
                    20                 25                 30
Arg Leu Leu Glu Gly Asp Glu Lys
        35                 40

<210> SEQ ID NO 42
<211> LENGTH: 40
<212> TYPE: PRT
<213> ORGANISM: Homo sapiens

<400> SEQUENCE: 42

Leu Gly Ser Arg Arg Cys Val His Arg Asp Leu Ala Ala Arg Asn Ile
 1               5                  10                 15
Leu Val Glu Ser Glu Ala His Val Lys Ile Ala Asp Phe Gly Leu Ala
                    20                 25                 30
Lys Leu Leu Pro Leu Asp Lys Asp
        35                 40
```

US 8,604,031 B2

1
INTRACELLULAR KINASE INHIBITORS

This application claims the benefit of and incorporates by reference provisional application Ser. No. 60/801,074 filed May 18, 2006 and Ser. No. 60/869,664 filed Dec. 12, 2006.

FIELD OF THE INVENTION

The invention relates to intracellular kinase inhibitors and their therapeutic uses.

BACKGROUND OF THE INVENTION

Intracellular kinases play important functions in cells of the immune system. For example, interleukin-2 inducible tyrosine kinase (ITK) plays a key role in T cell development and differentiation; it regulates IL-2 production via phospholipase Cγ1 (PLCγ1) and nuclear factor of activated T cells (NFAT); it mediates Th2 cell differentiation; and it regulates T cell migration and recruitment to lymphatic organs. Bruton's tyrosine kinase (BTK) is involved in signal transduction pathways which regulate growth and differentiation of B lymphoid cells. BTK also is involved in platelet physiology by regulating the glycoprotein VI/Fc receptor γ chain (GPVI-FcRγ)-coupled collagen receptor signaling pathway. For these reasons, inhibitors of intracellular kinases are useful for treating blood cell malignancies, solid tumors and for suppressing the immune system, for example in patients with autoimmune disorders or organ transplants. Intracellular kinase inhibitors also are useful for preventing or reducing the risk of thromboembolism.

BRIEF DESCRIPTION OF THE DRAWING

FIG. 2. Alignment of human ITK (SEQ ID NO:1) and BTK (SEQ ID NO:2).

FIG. 3. Alignment of kinase domains. Bolded amino acids, hinge; bolded and underlined amino acids, gatekeeper; italicized and bolded amino acids, Cys442 equivalents.

DETAILED DESCRIPTION OF THE INVENTION

Figure 1:
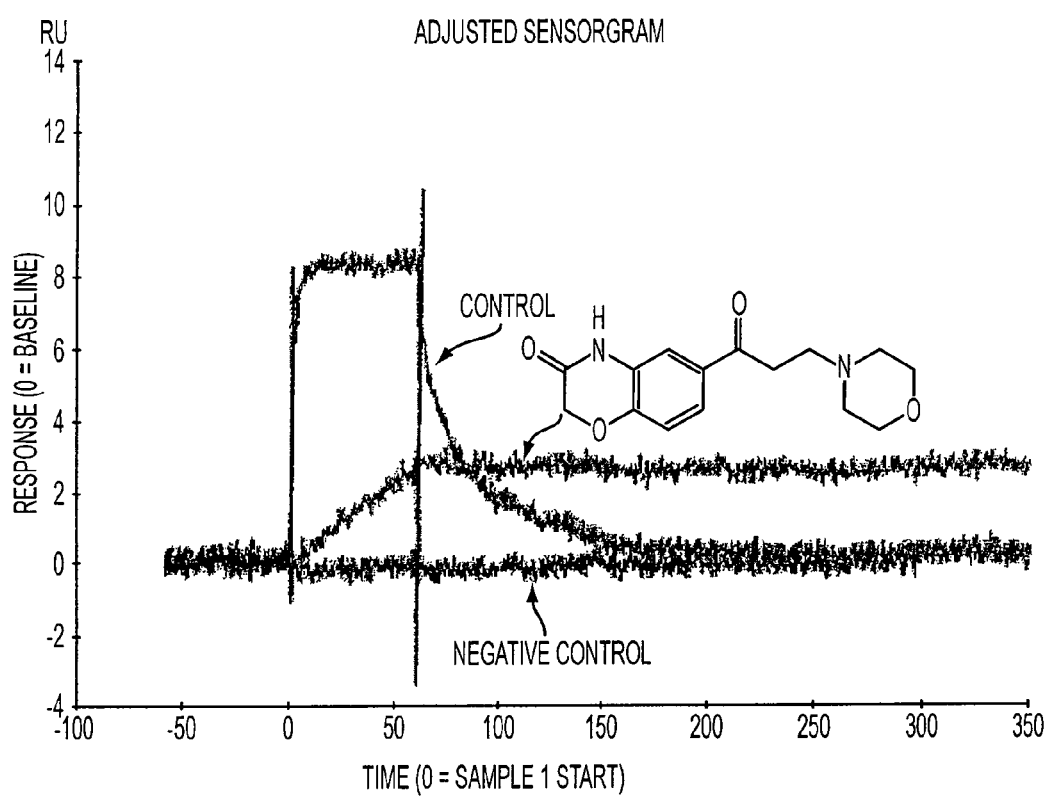
FIG. 1. Results of a BIACORE® experiment in which the ITK kinase domain was immobilized on a biosensor and evaluated for its ability to bind and dissociate from a small molecule.

The invention provides compounds which inhibit intracellular kinases, particularly ITK and BTK, with an $IC_{50}$ of 1 μM or below in an in vitro kinase assay as disclosed herein. The invention also provides pharmaceutical compositions and methods of using the compounds therapeutically. Patients who can be treated include those with blood cell malignancies, solid tumors, autoimmune disorders, and transplanted organs.

A review of the literature and patent database revealed the existence of compounds that inhibit ITK or BTK kinases. However, these compounds differ significantly from the compounds disclosed herein. In several instances, the compounds are pyrrolopyridines (e.g., US 2005/0215582). In other instances, the compounds are methyl dimethylbenzoates that belong thiazolyl family of compounds (e.g., US 2004/0077695). In all cases, these published compounds differ from the compounds disclosed herein based on the following parameters: the compounds do not correspond to the general structure shown in this application, do not require the amino acid triad DKC found in the kinase binding site and necessary for optimal compound inhibitory capability described herein, do not undergo elimination, and do not bind covalently to the kinase binding pocket.

Compounds of the invention which inhibit ITK can be used, e.g., to treat T cell malignancies. Preferred compounds of the invention inhibit both ITK and BTK with an $IC_{50}$ of 1 μM or below for each enzyme. Such compounds can be used, e.g., to treat both T and B cell malignancies, as well as EGFR or HER positive tumors.

The Tec family of kinases share a common subunit structure composed of a Src homology domain 2 ($SH_2$), an $SH_3$ and a catalytic kinase domain. Further, they are uniquely identified by the presence of a Tec homology region (TH) and a pleckstrin homology (PH) domain. There are four known crystallographic structures described for the Tec family of kinases. These include (a) two structures representing the phosphorylated and unphosphorylated staurosporine-bound ITK (PDB codes 1SM2, 1SNU); (b) one structure of the unphosphorylated apo-form of ITK (PDB code 1SNX), and (c) one structure for the unphosphorylated apo-form of BTK (Mao et al. *J. Biol. Chem.* 2001, 276, 41435-41443). For the purpose of clarity of explanation, this disclosure will represent these kinase structures with those of the nearly identical ITK structures in (a) and (b) incorporated herein by reference (Brown et al. *J. Biol. Chem.* 2004, 279, 18727-18732) focusing attention on the ATP binding site. For the sake of uniformity, the residue numbering in these kinase structures as represented in the Protein Data Bank have been incorporated throughout this document to describe the kinase domain. The amino acid sequence of human ITK is shown in SEQ ID NO:1. The amino acid sequence of human BTK is shown in SEQ ID NO:2. Homologous residues in the other kinases and sequences from other sources may be numbered differently.

Referring to FIG. 2, The ITK kinase domain (residues 357-620) can be broken down into two components: the N-terminal lobe (residues 357-437) and the C-terminal lobe (residues 438-620). Like most kinases, the connecting region between the two lobes is a flexible hinge region described below, that forms part of the catalytic active site. The ordered nature of the C-helix places the catalytically important residues of Glu406, Lys391 and Asp500 in an orientation typical of the active form of a protein kinase. The Gly-rich loop (residues 362-378), commonly observed in kinases, assumes an extended and open conformation typical of an active kinase.

The boundaries of the ATP binding site are demarcated by the following residues: (a) the glycine-rich loop (Gly370, Ser371, Gly372, Gln373, Phe374 and Gly375); (b) the hinge region (Phe435, Glu436, Phe437, Met438, Glu439, His440, Gly441 and Cys442); and (c) the catalytic residues Lys391 and Asp500. Additionally, the active site also comprises several other hydrophobic residues including Ala389, Ile369, Val377, Val419, and Leu 489 as well as the hydrophilic residue Ser499.

Similar to other kinases, the hinge region of ITK contains two backbone carbonyls and one backbone amino group as potential hydrogen bond acceptor and donor sites respectively. Similar backbone interactions have been observed in the interaction of kinases with the adenine base of ATP and several competitive inhibitors have been designed pursuing this concept. At the N-terminal end of the hinge region lies the "gatekeeper" residue, Phe435. This residue blocks access to an internal hydrophobic pocket, and, at the same time, provides a potential site of interaction for aromatic or hydrophobic groups. This "gatekeeper" residue is a significant difference between ITK and BTK. Despite the strong overall sequence identity between BTK and ITK, the presence of the smaller threonine residue as a gatekeeper in the active site of BTK justifies a key similarity of the latter to the active site of several kinases such as Src/Abl/EGFR. The absence of the bulkier Phe gatekeeper allows access to an internal hydrophobic pocket for these kinases, a fact that has been exploited for the design of allosteric inhibitors, and to improve the affinity of ATP-competitive inhibitors through the addition of a hydrophobic pharmacophore.

Definitions

"Alkyl" is a monovalent linear or branched saturated hydrocarbon radical and can be substituted or unsubstituted. Linear or branched alkyls typically have between 1 and 12 carbon atoms (e.g., 1, 2, 3, 4, 5, 6, 7, 8, 9, 10, 11, 12). Lower alkyls, or "$C_1$-$C_6$ alkyls," have between 1 and 6 carbon atoms (e.g., 1, 2, 3, 4, 5, or 6). Optional substitutents include halogen, hydroxyl, alkoxy, aryloxy, amino, N-alkylamino, N,N-dialkylamino, alkylcarbamoyl, arylcarbamoyl, aminocarbamoyl, N-alkylaminocarbamoyl, N,N-dialkylaminocarbamoyl, alkylsulfonylamino, arylsulfonylamino, carboxy, carboxyalkyl, N-alkylcarboxamido, N,N-dialkylcarboxamido, alkylthio, alkylsulfinyl, alkylsulfonyl, trihaloalkylsulfonylamino (e.g., trifluoromethylsulfonylamino), arylthio, arylsulfinyl, arylsulfonyl, and heterocyclyl. Examples of linear or branched $C_1$-$C_6$ alkyl are methyl, ethyl, propyl, isopropyl, sec-butyl, tert-butyl, n-butyl, n-pentyl, sec-pentyl, tert-pentyl, n-hexyl, isopentyl, fluoromethyl, trifluoromethyl, hydroxybutyl, dimethylcarboxyalkyl, aminoalkyl, and benzylpropyl.

"Acyl" (or "alkylcarbonyl") is the radical —C(O)$R^8$, wherein $R^8$ is an optionally substituted lower alkyl. Examples of acyl include, but are not limited to, acetyl, propionyl, n-butyryl, sec-butyryl, t-butyryl, iodoacetyl, and benzylacetyl.

"Acyloxy" is the radical —OC(O)$R^8$, wherein $R^8$ is an optionally substituted lower alkyl. Examples of acyloxy include, but are not limited to, acetoxy, propionyloxy, butyryloxy, trifluoroacetoxy, and diiodobutyryloxy.

"Alkoxy" is the radical —O$R^8$, wherein $R^8$ is an optionally substituted lower alkyl. Examples of alkoxy include methoxy, ethoxy, propoxy, 2-propoxy, butoxy, sec-butoxy, tert-butoxy, pentyloxy, hexyloxy, fluoromethoxy, and iodoethoxy.

"Alkylamino" is the radical —N$R^7R^8$, wherein $R^7$ is hydrogen or an optionally substituted lower alkyl and $R^8$ is an optionally substituted lower alkyl. Examples of alkylamino groups are methylamino, ethylamino, isopropylamino, dimethylamino, diethylamino, and trifluoromethylamino.

"Alkylaminocarbonyl" (or "alkylcarbamoyl") is the radical —C(O)N$R^7R^8$, wherein $R^7$ is hydrogen or an optionally substituted lower alkyl and $R^8$ is an optionally substituted lower alkyl. Examples of alkylaminocarbonyl include, but are not limited to, methylaminocarbonyl, dimethylaminocarbonyl, t-butylaminocarbonyl, n-butylaminocarbonyl, iso-propylaminocarbonyl, and trifluoromethylaminocarbonyl.

"Alkylaminosulfonyl" is the radical —S(O)$_2$N$R^7R^8$, wherein $R^7$ is hydrogen or an optionally substituted lower alkyl and $R^8$ is an optionally substituted lower alkyl. Examples of alkylaminosulfonyl include, but are not limited to, methylaminosulfonyl, dimethylaminosulfonyl, and tri-iodomethylaminosulfonyl.

"Alkoxycarbonyl" or "alkyl ester" is the radical —C(O)O$R^8$, wherein $R^8$ is an optionally substituted lower alkyl. Examples of alkoxycarbonyl radicals include, but are not limited to, methoxycarbonyl, ethoxycarbonyl, sec-butoxycarbonyl, isopropyloxycarbonyl, and difluoromethoxycarbonyl.

"Alkylcarbonylamino" is the radical —N$R^7$C(O)$R^8$, wherein $R^7$ is hydrogen or an optionally substituted lower alkyl and $R^8$ is an optionally substituted lower alkyl. Examples of alkylcarbonylamino include, but are not limited to, methylcarbonylamino, iso-propylcarbonylamino, and t-butylcarbonylamino.

"Alkylcarboxamido" is the radical —C(O)N$R^7R^8$, wherein $R^7$ is hydrogen or an optionally substituted lower alkyl and $R^8$ is an optionally substituted lower alkyl. Examples of alkylcarboxamidos are methylcarboxamido, ethylcarboxamido, isopropylcarboxamido, and n-propylcarboxamido.

"Alkylsulfonyl" is the radical —S(O)$_2R^8$, wherein $R^8$ is an optionally substituted lower alkyl. Examples of alkylsulfonyl include, but are not limited to, methylsulfonyl, trifluoromethylsulfonyl, and propylsulfonyl.

"Alkylsulfonylamino" is the radical —N$R^7$S(O)$_2R^8$, wherein $R^7$ is hydrogen or an optionally substituted lower alkyl and $R^8$ is an optionally substituted lower alkyl. Examples of alkylsulfonylamino include, but are not limited to, methylsulfonylamino, propylsulfonylamino, and trifluoromethylsulfonylamino.

"Aryl" is the monovalent aromatic carbocyclic radical of one individual aromatic ring or two or three fused rings in which at least one of the fused rings is aromatic. Aryls can be optionally substituted on one or more rings with one or more of halogen, hydroxyl, alkoxy, aryloxy, amino, N-alkylamino, N,N-dialkylamino, alkylcarbamoyl, arylcarbamoyl, aminocarbamoyl, N-alkylaminocarbamoyl, N,N-dialkylaminocarbamoyl, alkylsulfonylamino, arylsulfonylamino, carboxy, carboxyalkyl, N-alkylcarboxamido, N,N-dialkylcarboxamido, alkylthio, alkylsulfinyl, alkylsulfonyl, trifluoromethylsulfonylamino, arylthio, arylsulfinyl, arylsulfonyl, hydroxyalkyl, alkoxyalkyl, aryloxalkyl, aminoalkyl, N-alkylaminoalkyl, N,N-dialkylaminoalkyl, alkylcarbamoylalkyl, arylcarbamoylalkyl, aminocarbamoylalkyl, N-alkylaminocarbamoylalkyl N,N-dialkylaminocarbamoylalkyl, alkylsulfonylaminoalkyl, arylsulfonylaminoalkyl, alkylcarboxy, alkylcarboxyalkyl, N-alkylcarboxamindoalkyl, N,N-dialkylcarboxamindoalkyl, alkylthioalkyl, alkylsulfinylalkyl, alkylsulfonylalkyl, trifluoromethylsulfonylaminoalkyl, arylthioalkyl, arylsulfinylalkyl, and arylsulfonylalkyl. Examples of aryls are phenyl, naphthyl, tetrahydronaphthyl, indanyl, indanonyl, tetralinyl, tetralonyl, fluorenonyl, phenanthryl, anthryl, and acenaphthyl.

"Arylalkoxycarbonyl" or "arylalkyl ester" is the radical —C(O)O$R^8$X, wherein $R^8$ is an optionally substituted lower alkyl and X is an optionally substituted aryl. Examples of aryloxycarbonyl radicals include, but are not limited to, benzyl ester, phenyl ethyl ester, and dimethylphenyl ester.

"Arylalkylcarbamoyl" is the radical —C(O)NH$R^8$X, wherein $R^8$ is an optionally substituted lower alkyl and X is an optionally substituted aryl. Examples of arylalkylcarbamoyl include, but are not limited to, benzylcarbamoyl, phenylethylcarbamoyl, and cyanophenylcarbamoyl.

"Arylalkylcarbonyl" (or "aralkylcarbonyl") is the radical —C(O)$R^8$X, wherein $R^8$ is an optionally substituted lower alkyl and X is an optionally substituted aryl. Examples of arylalkylcarbonyl radicals include, but are not limited to, phenylacetyl and fluorophenylacetyl.

"Arylaminocarbonyl" (or "arylcarbamoyl") is the radical —C(O)NXX', wherein X is an optionally substituted aryl and X' is hydrogen or an optionally substituted aryl. Examples of arylaminocarbonyl include, but are not limited to, phenylaminocarbonyl, methoxyphenylaminocarbonyl, diphenylaminocarbonyl, and dimethoxyphenylaminocarbonyl.

"Arylaminosulfonyl" is the radical —S(O)$_2$NXX', wherein X is an optionally substituted aryl and X' is hydrogen or an optionally substituted aryl. Examples of arylaminosulfonyl include, but are not limited to, phenylaminosulfonyl, methoxyphenylaminosulfonyl, and triiodomethylaminosulfonyl.

"Arylcarbonyl" is the radical —C(O)X, wherein X is an optionally substituted aryl. Examples of arylcarbonyl radicals include, but are not limited to, benzoyl, naphthoyl, and difluorophenylcarbonyl.

"Arylcarbonylamino" is the radical —NHC(O)X, wherein X is an optionally substituted aryl. Examples of arylcarbonylamino include, but are not limited to, phenylcarbonylamino, tosylcarbonylamino, and cyanophenylcarbonylamino.

"Aryloxy" is —OX, wherein X is an optionally substituted aryl. Examples of aryloxys include phenyloxy, naphthyloxy, tetrahydronaphthyloxy, indanyloxy, indanonyloxy, biphenyloxy, tetralinyloxy, tetralonyloxy, fluorenonyloxy, phenanthryloxy, anthryloxy, and acenaphthyloxy.

"Aryloxycarbonyl" or "aryl ester" is the radical —C(O)OX, wherein X is an optionally substituted aryl. Examples of aryloxycarbonyl radicals include, but are not limited to, phenyl ester, naphthyl ester, dimethylphenyl ester, and trifluorophenyl ester.

"Arylsulfonyl" is the radical —S(O)$_2$X, wherein X is an optionally substituted aryl. Examples of arylsulfonyl include, but are not limited to, phenylsulfonyl, nitrophenylsulfonyl, methoxyphenylsulfonyl, and 3,4,5-trimethoxyphenylsulfonyl.

"Arylsulfonylamino" is the radical —NS(O)$_2$X, wherein X is an optionally substituted aryl. Examples of arylsulfonylamino include, but are not limited to, phenylsulfonylamino, naphthylsulfonylamino, 2-butoxyphenylsulfonylamino, 4-chlorophenylsulfonylamino, 2,5-diethoxysulfonylamino, 4-hexyloxyphenylsulfonylamino, 4-methylphenylsulfonylamino, naphtylsulfonylamino, 4-methoxyphenylsulfonylamino, N-methylphenylsulfonylamino, and 4-cyanophenylsulfonylamino, phenylsulfonylamino, 4-methylphenylsulfonylamino, naphtylsulfonylamino. phenylsulfonylamino, and 4-metylphenylsulfonylamino.

"Arylsulfonyloxy" is the radical —OS(O)$_2$X, wherein X is an optionally substituted aryl. Examples of arylsulfonyloxy include, but are not limited to, benzenesulfonyloxy and 4-chloro-benzenesulfonyloxy.

"Cycloalkyl" is a monovalent saturated carbocyclic radical consisting of one or more rings, preferably one, of three to seven carbons per ring and can be optionally substituted with one or more of hydroxyl, alkoxy, aryloxy, amino, N-alkylamino, N,N-dialkylamino, alkylcarbamoyl, arylcarbamoyl, aminocarbamoyl, N-alkylaminocarbamoyl, N,N-dialkylaminocarbamoyl, alkylsulfonylamino, arylsulfonylamino, carboxy, carboxyalkyl, N-alkylcarboxamido, N,N-dialkylcarboxamido, alkylthio, alkylsulfinyl, alkylsulfonyl, trifluoromethylsulfonylamino, arylthio, arylsulfinyl, arylsulfonyl, hydroxyalkyl, alkoxyalkyl, aryloxalkyl, aminoalkyl, N-alkylaminoalkyl, N,N-dialkylaminoalkyl, alkylcarbamoylalkyl, arylcarbamoylalkyl, aminocarbamoylalkyl, N-alkylaminocarbamoylalkyl N,N-dialkylaminocarbamoylalkyl, alkylsulfonylaminoalkyl, arylsulfonylaminoalkyl, alkylcarboxy, alkylcarboxyalkyl, N-alkylcarboxamindoalkyl, N,N-dialkylcarboxamindoalkyl, alkylthioalkyl, alkylsulfinylalkyl, alkylsulfonylalkyl, trifluoromethylsulfonylaminoalkyl, arylthioalkyl, arylsulfinylalkyl, and arylsulfonylalkyl. Examples of cycloalkyls are cyclopropyl, cyclobutyl, cyclopentyl, cyclohexyl, adamantyl, cyclooctyl, cycloheptyl, tetrahydro-naphthalene, methylenecylohexyl, indanyl, indenyl, and fluorenyl.

"Cycloalkylcarbonyl" is the radical —C(O)R, wherein R is an optionally substituted cycloalkyl radical. Examples of cycloalkylcarbonyl radicals include, but are not limited to, cyclobutanoyl, cyclopentanoyl, cyclohexanoyl, and trifluorocyclopentanoyl.

"Halogen" includes fluorine, chlorine, bromine, and iodine.

"Heteroaryl" is a monovalent aromatic cyclic radical having one or more rings, preferably one to three rings, of four to eight atoms per ring, incorporating one or more heteroatoms selected independently from nitrogen, oxygen, silicon, and sulfur. Heteroaryls can be optionally substituted on one or more rings with one or more of halogen, hydroxyl, alkoxy, aryloxy, amino, N-alkylamino, N,N-dialkylamino, alkylcarbamoyl, arylcarbamoyl, aminocarbamoyl, N-alkylaminocarbamoyl, N,N-dialkylaminocarbamoyl, alkylsulfonylamino, arylsulfonylamino, carboxy, carboxyalkyl, N-alkylcarboxamido, N,N-dialkylcarboxamido, alkylthio, alkylsulfinyl, alkylsulfonyl, trifluoromethylsulfonylamino, arylthio, arylsulfinyl, arylsulfonyl, hydroxyalkyl, alkoxyalkyl, aryloxalkyl, aminoalkyl, N-alkylaminoalkyl, N,N-dialkylaminoalkyl, alkylcarbamoylalkyl, arylcarbamoylalkyl, aminocarbamoylalkyl, N-alkylaminocarbamoylalkyl N,N-dialkylaminocarbamoylalkyl, alkylsulfonylaminoalkyl, arylsulfonylaminoalkyl, alkylcarboxy, alkylcarboxyalkyl, N-alkylcarboxamindoalkyl, N,N-dialkylcarboxamindoalkyl, alkylthioalkyl, alkylsulfinylalkyl, alkylsulfonylalkyl, trifluoromethylsulfonylaminoalkyl, arylthioalkyl, arylsulfinylalkyl, and arylsulfonylalkyl.

Representative examples of monocyclic ring system heteroaryls include, but are not limited to, azetidinyl, azepinyl, aziridinyl, diazepinyl, 1,3-dioxolanyl, dioxanyl, dithianyl, furyl, imidazolyl, imidazolinyl, imidazolidinyl, isothiazolyl, isothiazolinyl, isothiazolidinyl, isoxazolyl, isoxazolinyl, isoxazolidinyl, morpholinyl, oxadiazolyl, oxadiazolinyl, oxadiazolidinyl, oxazolyl, oxazolinyl, oxazolidinyl, piperazinyl, piperidinyl, pyranyl, pyrazinyl, pyrazolyl, pyrazolinyl, pyrazolidinyl, pyridyl, pyrimidinyl, pyridazinyl, pyrrolyl, pyrrolinyl, pyrrolidinyl, tetrahydrofuranyl, tetrahydrothiophenyl, tetrazinyl, tetrazolyl, thiadiazolyl, thiadiazolinyl, thiadiazolidinyl, thiazolyl, thiazolinyl, thiazolidinyl, thiophenyl, thiomorpholinyl, 1,1-dioxidothiomorpholinyl, thiopyranyl, triazinyl, triazolyl, and trithianyl.

Bicyclic ring systems include any of the above monocyclic ring systems fused to an aryl group, a cycloalkyl group, or another heteroaryl monocyclic ring system. Representative examples of bicyclic ring systems include but are not limited to, benzimidazolyl, benzothiazolyl, benzothiophenyl, benzoxazolyl, benzofuranyl, benzopyranyl, benzothiopyranyl, benzodioxinyl, 1,3-benzodioxolyl, cinnolinyl, indazolyl, indolyl, indolinyl, indolizinyl, naphthyridinyl, isobenzofuranyl, isobenzothiophenyl, isoindolyl, isoindolinyl, isoquinolyl, phthalazinyl, pyranopyridyl, quinolyl, quinolizinyl, quinoxalinyl, quinazolinyl, tetrahydroisoquinolyl, tetrahydroquinolyl, and thiopyranopyridyl.

Tricyclic rings systems include any of the above bicyclic ring systems fused to an aryl group, a cycloalkyl group, or a heteroaryl monocyclic ring system. Representative examples of tricyclic ring systems include, but are not limited to, acridinyl, carbazolyl, carbolinyl, dibenzofuranyl, dibenzothiophenyl, naphthofuranyl, naphthothiophenyl, oxanthrenyl, phenazinyl, phenoxathiinyl, phenoxazinyl, phenothiazinyl, thianthrenyl, thioxanthenyl, and xanthenyl.

"Heteroarylaminocarbonyl" is the radical —C(O)NZZ', wherein Z is an optionally substituted heteroaryl and Z' is hydrogen or an optionally substituted heteroaryl. Examples of heteroarylaminocarbonyl include, but are not limited to, pyridinylaminocarbonyl, and thienylaminocarbonyl, furanylaminocarbonyl.

"Heteroarylaminosulfonyl" is the radical —S(O)$_2$N ZZ', wherein Z is an optionally substituted heteroaryl and Z' is hydrogen or an optionally substituted heteroaryl. Examples of heteroarylaminosulfonyl include, but are not limited to, thienylaminosulfonyl, piperidinylaminosulfonyl, furanylaminosulfonyl, and imidazolylaminosulfonyl.

"Heteroarylcarbonyl" is the radical —C(O)Z, wherein Z is an optionally substituted heteroaryl. Examples of heteroarylcarbonyl radicals include, but are not limited to, pyridinoyl, 3-methylisoxazoloyl, isoxazoloyl, thienoyl, and furoyl.

"Heteroarylsulfonyl" is the radical —S(O)$_2$Z, wherein Z is an optionally substituted heteroaryl. Examples of heteroarylsulfonyl include, but are not limited to, thienylsulfonyl, furanylsulfonyl, imidazolylsulfonyl, and N-methylimidazolylsulfonyl.

"Heteroarylsulfonyloxy" is the radical —OS(O)$_2$Z, wherein Z is an optionally substituted heteroaryl. An examples of hetroarylsulfonyloxy is thienylsulfonyloxy.

"Heterocycle" is a saturated or partially unsaturated carbocyclic radical having one, two, or three rings each containing one or more heteroatoms selected independently from nitrogen, oxygen, silicon, and sulfur. A heterocycle can be unsubstituted or substituted on any or all of the rings with one or more of halogen, aryl, heteroaryl, hydroxy, alkoxy, aryloxy, amino, N-alkylamino, N,N-dialkylamino, alkylsulfonylamino, arylsulfonylamino, alkylcarbamoyl, arylcarbamoyl, aminocarbamoyl, N-alkylaminocarbamoyl, N,N-dialkylaminocarbamoyl, carboxy, alkylcarboxy, N-alkylcarboxamido, N,N-dialkylcarboxamido, alkylthio, alkylsulfinyl, alkylsulfonyl, trifluoromethylsulfonylamino, arylthio, arylsulfinyl, arylsulfonyl, carboxyalkyl, hydroxyalkyl, alkoxyalkyl, aryloxalkyl, aminoalkyl, N-alkylaminoalkyl, N,N-dialkylaminoalkyl, alkylcarbamoylalkyl, arylcarbamoylalkyl, aminocarbamoylalkyl, N-alkylaminocarbamoylalkyl N,N-dialkylaminocarbamoylalkyl, alkylsulfonylaminoalkyl, arylsulfonylaminoalkyl, alkylcarboxyalkyl, N-alkylcarboxamindoalkyl, N,N-dialkylcarboxamindoalkyl, alkylthioalkyl, alkylsulfinylalkyl, alkylsulfonylalkyl, trihaloalkylsulfonylaminoalkyl, arylthioalkyl, arylsulfinylalkyl, and arylsulfonylalkyl. Examples of heterocycles include piperazinyl, piperidinyl, pyrrolidinyl, morpholinyl, thiamorpholinyl, pyrrolyl, phthalamide, succinamide, and maleimide.

"Heterocyclylcarbonyl" (or "heterocyclocarbonyl") is the radical —C(O)M', wherein M' is an optionally substituted heterocycle. Examples of heterocyclylcarbonyl include, but are not limited to, piperazinoyl, morpholinoyl, and pyrrolindinoyl.

"Heterocyclylsulfonyl" is the radical —S(O)$_2$Z', wherein M' is an optionally substituted heterocycle. Examples of heterocyclylsulfonyl include, but are not limited to, piperidinylsulfonyl and piperazinylsulfonyl.

"Heterocyclylsulfonyloxy" is the radical —OS(O)$_2$M', wherein M' is an optionally substituted heterocycle. Examples of heterocyclylsulfohyloxy include, but are not limited to, 3,5,dimethyl-isoxazolesulfonyloxy and pyrrolidinylsulfonyloxy.

Compounds

This invention provides compounds which inhibit tyrosine kinases, particularly Tec (e.g., ITK, BTK), Src (Src, Lck, etc.) and EGFR kinases (e.g., EGFR1, Her 2, Her 4), and Jak kinase (e.g., Jak3), having structures that exploit a discrete mechanistic rationale described herein. This mechanism provides for the utilization of the kinase catalytic machinery, described in the ITK crystallographic structures as the acid-base pair residues Lys391 and Asp500 (herein referred to as the "catalytic dyad"), to trigger a transformation that activates the proposed inhibitory compounds within the enzyme active site. This transformation involves the elimination of a leaving group, resulting in the in situ formation of an electrophilic intermediate capable of forming a covalent adduct with an active site cysteine residue thereby irreversibly inhibiting the function of the target enzyme. This cysteine residue is identifiable as Cys442 in the ITK crystallographic structure. The group of kinases with the above described triad, including ITK, BTK, BMX, Tec, TXK, BLK, EGFr, Her 2, Her 4 and JAK3, will be referred to as the DKC triad kinases. Various embodiments of the invention relate to this group, its possible sub-groupings, and to its individual members.

It is known that several compounds, typically containing electrophilic Michael acceptors, form covalent adducts with enzymatic nucleophiles present in the active site to irreversibly inhibit the target enzyme (Slichenmeyer, W. J.; Elliott, W. C.; Fry, D. W. *Semin. Oncol.* 2001, 28, 80-85; Shimamura, T.; Ji, H.; Minami, Y.; Thomas, R. K.; Lowell, A. M.; Sha, K.; Greulich, H.; Glatt, K. A.; Meyerson, M.; Shapiro, I.; Wong, K.-K. *Cancer Res.* 2006, 66, 6487-6491). However, the compounds described in this invention are unique in that the transformation that forms the electrophilic intermediate takes place preferentially in situ, i.e. within the enzyme active site. Outside of an appropriate active site, these compounds are much less likely to undergo beta-elimination and form adducts with other proteins. The compounds described within must first bind in the active site of the target kinase and achieve a specific conformational geometry with respect to the relevant catalytic residues in order to effectively trigger elimination of the leaving group, thereby unmasking the adduct-forming intermediate. This intermediate forms a covalent, irreversible adduct with the proximal active site cysteine residue. In some embodiments the reaction proceeds stepwise; in other embodiments it is concerted. In preferred embodiments additional portions of the inhibitor molecule interact with other portions of the kinase, particularly in the active site, to promote favorable binding affinity and positioning. Such interactions contribute to the specificity of various inhibitors so that some inhibitors are inhibit a single kinase whereas others inhibit multiple kinases with similar or different IC$_{50}$s. To our knowledge, this is the first example of an in situ formation of an active inhibitor in a kinase active site.

Compound Interaction with the Kinase Domain

Without specifying the kinetics of the reaction, the inhibition of the target kinase goes through the following sequence of steps to form the adduct with the inhibitory compounds:

(1) The catalytic lysine N—H is positioned within hydrogen bonding distance (approximately 1.8-4.0 Angstroms) of a hydrogen bond acceptor Y in the compound that exists in the form of a C=Y (Y=O, S, NOR) functionality. Polarization of the C=Y bond results in increasing the acidity of the proton (H$_A$) at a carbon atom alpha to the C=Y group.

(2) Acting as a base, the aspartate of the catalytic dyad extracts the acidic proton H$_A$, leaving behind a conjugated carbanion that forms for Y=O, an enol, H-bonded enolate through standard electronic rearrangement. For Y=S, it would form a thioenol or H-bonded thioenolate, and for Y=NOR, it would form an alkoxy (R=alkyl), aryloxy (R=aryl) or hydroxy (R=H) enamine.

(3) The formation of the enol/thioenol/enamine facilitates the elimination of the leaving group attached at a carbon beta to C=Y, through a process known as "β-elimination." The leaving group, attached to the compound through protonatable heteroatom Z, may optionally be additionally tethered to the rest of the compound.

(4) Being a strong nucleophilic species, the sulfhydryl group of the neighboring cysteine residue reacts with the newly formed electrophilic elimination product. This addition reaction (thioalkylation) forms the covalent adduct to the kinase resulting in its irreversible inhibition and abrogation of activity.

The inhibitory activity of this class of compounds toward select kinases is dependent on their ability to bind effectively in proximity to the appropriate calalytic environment, the existence of a polarizable C=Y group (C=O in formula (I), below) with appropriate reactivity and an adjacent alpha proton to allow elimination of the beta leaving group.

In turn, the elimination process that generates a reactive electrophilic species requires removal of the abstractable alpha proton that is facilitiated by adequate positioning of the C=Y group in the catalytic environment. The generated electrophilic Michael acceptor, in turn is required to be positioned within reactive distance of the key cysteine residue. The appropriate positioning of the abstractable proton in the kinase binding site is achieved through pharmacophoric elements that include:

(i) a C=Y moiety that serves the dual purpose of polarizing the proximal C—H bond of the abstractable proton, and hydrogen bonding to the lysine residue of the catalytic pair;

(ii) a hydrophobic aryl or heteroaryl group that interacts with specific hydrophobic residues in the binding site at an approximate distance of 3-5 Å from Y, (iii) several (one to 3) hydrophilic pharmacophores that interact with the backbone in the hinge region, (vi) a carbon atom in the beta position from the C=Y carbon atom, that is positioned within reactive distance of the sulfhydryl group of the relevant cysteine as explained below.

The effective "reactive distance" to the cysteine sulfhydryl group as stated above is observed in the range of about 3-10 Å using computational design methods that test the binding of inhibitors to the ITK ATP binding site, wherein the enzyme is maintained in a fixed conformation. While a distance of 10 Å in a rigid system would be too far to effect a chemical reaction, the enzymatic nucleophilic moiety and the inhibitor's electrophilic moiety can readily be brought together through a series of low energy barrier rotations around the flexible inhibitor bonds as well as the cysteinyl side chain. Overall global conformational changes, common to kinase systems, cannot be ruled out either but are not readily measurable. Such conformational changes, which can be envisioned by computational predictions, are adequate in bringing the two reactive pieces in close enough proximity to effect covalent bond formation.

Compounds according to the invention have the structural formula:

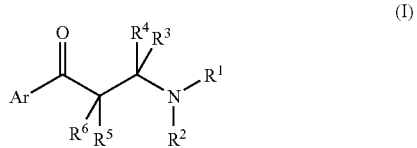

(I)

wherein:

Ar is optionally substituted aryl or optionally substituted heteroaryl;

$R^3$, $R^4$, $R^5$, and $R^6$ are independently hydrogen or optionally substituted $C_1$-$C_6$ alkyl; and $R^1$ and $R^2$ (a) are independently hydrogen, optionally substituted $C_1$-$C_6$ alkyl, piperidine, or furanyl; or (b) are taken together with the nitrogen atom to which they are attached to form (i) a 5- to 7-membered optionally substituted aryl, (ii) a 5- to 7-membered optionally substituted heteroaryl, or (iii) a 5- to 7-membered optionally substituted heterocycle which may be unfused or fused to an optionally substituted aryl.

In some embodiments Ar is selected from the group consisting of:

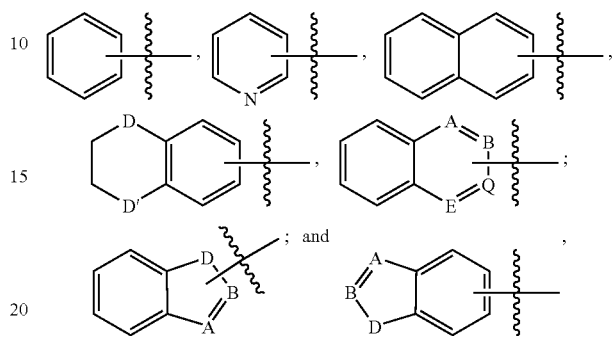

wherein A, B, E, and Q are independently CH, O, or N; and D and D' are independently $CH_2$, NH, O, or S.

In other embodiments Ar is selected from the group consisting of:

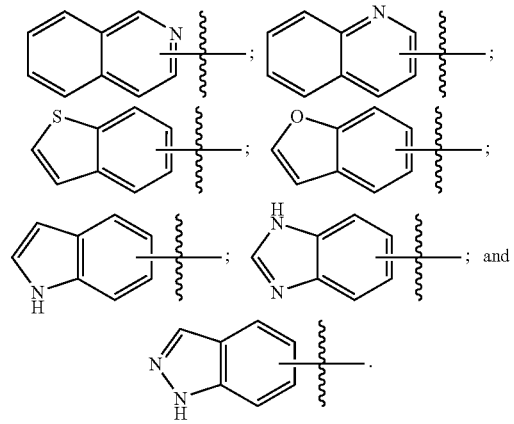

Examples of 5- to 7-membered heterocycles include:

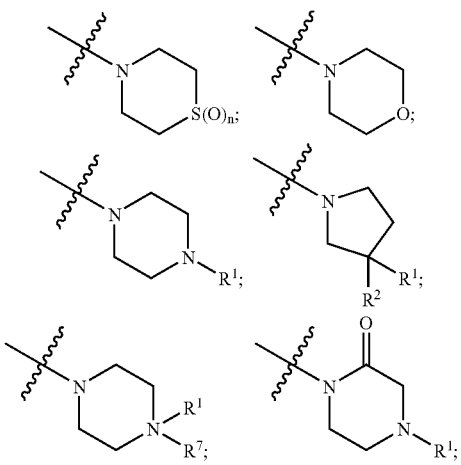

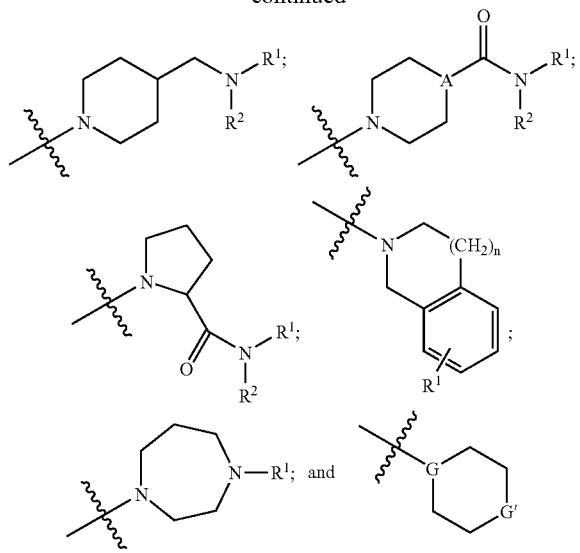

wherein:
G is N, CH, or S;
G' is NH, CH, or S;
n=0-2;
$R^1$ and $R^2$ are as defined above; and
$R^7$ is hydrogen, optionally substituted $C_1$-$C_6$ alkyl, optionally substituted aryl, or optionally substituted heteroaryl.

Preferred 5- to 7-membered heterocycles are piperazinyl, piperidinyl, pyrrolidinyl, and morpholinyl. Preferred substituents for piperazinyl are $C_1$-$C_6$ alkyl, dialkyl $C_1$-$C_6$ aminoalkyl, aryl, aralkyl, cycloalkyl, and cycloalkyl-alkyl. Preferred substituents for piperidinyl are $C_1$-$C_6$ alkyl and aralkyl. In some embodiments piperidinyl is benzofused to form isoquinolinyl. Preferred substituents for pyrrolidinyl are $C_1$-$C_6$ alkyl, aryl, and aralkyl. In some embodiments pyrrolidinyl is benzofused to form isoindolyl. Preferred substituents for morpholinyl are $C_1$-$C_6$ alkyl and arylalkyl.

Some compounds have the structural formula:

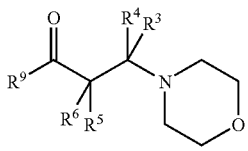

(II)

wherein:
$R^3$, $R^4$, $R^5$, and $R^6$ are as defined above;
$R^9$ is selected from,

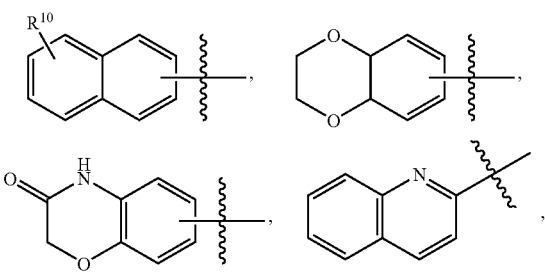

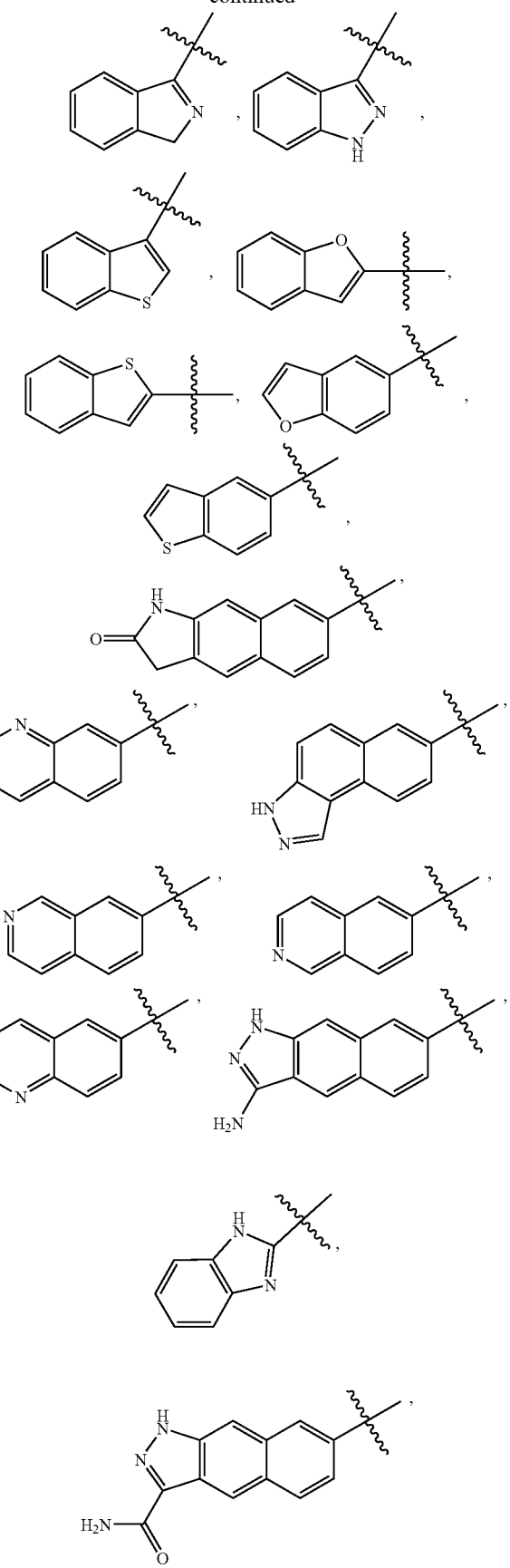

-continued
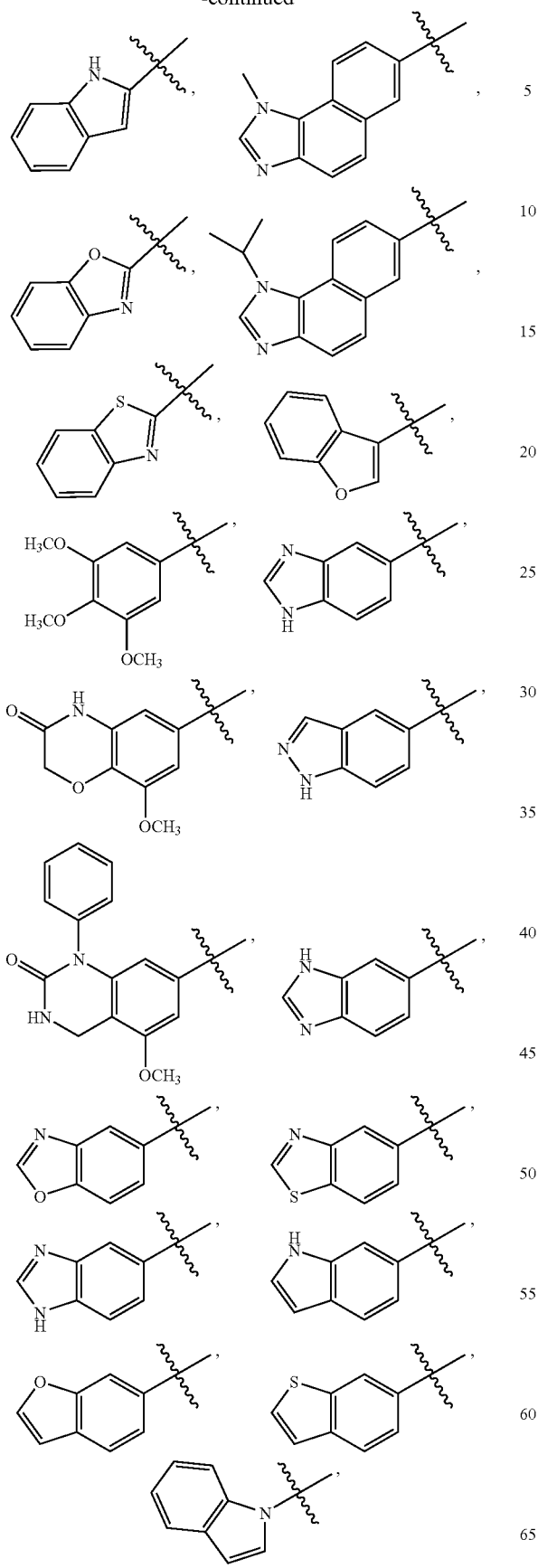
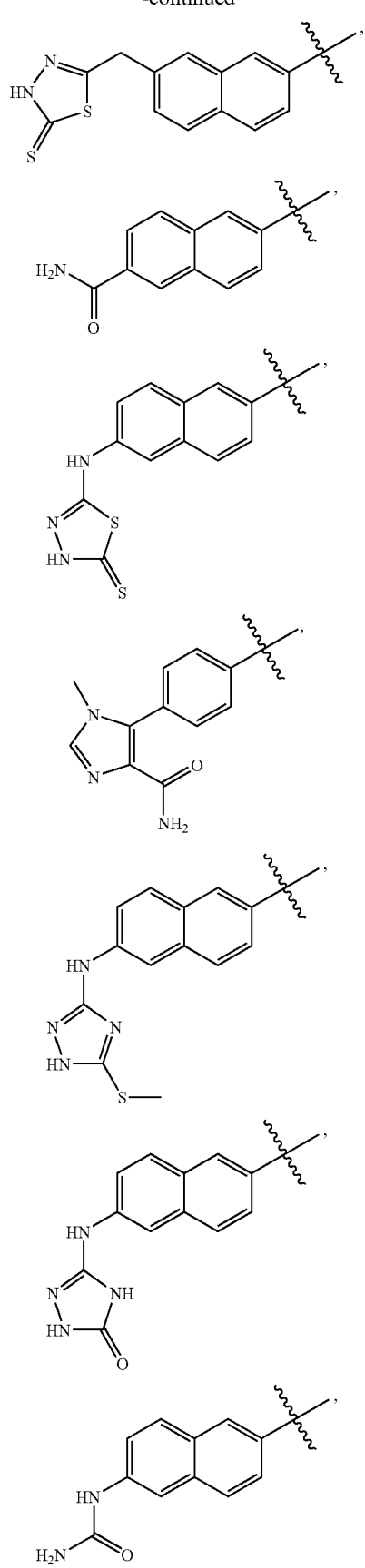

-continued
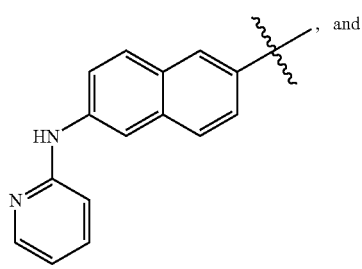, and
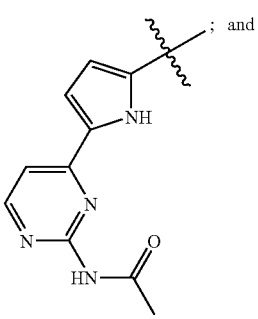;  and
$R^{10}$ is hydrogen, —OH, —COOH, —CONH$_2$, or —NCO, wherein if $R^9$ is naphthyl, then $R^5$ and $R^6$ are not both methyl.
Examples of these compounds include:
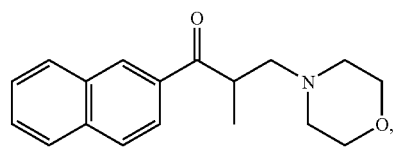
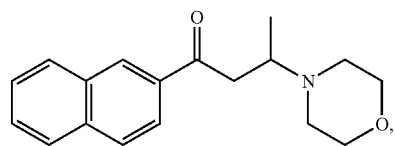
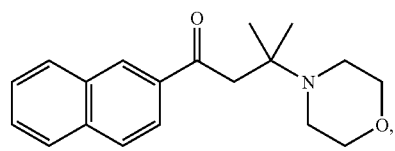
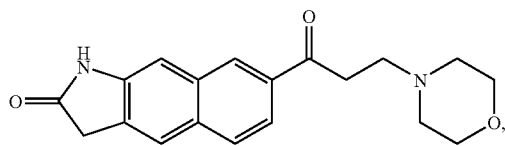
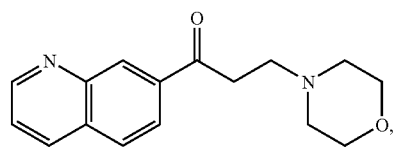
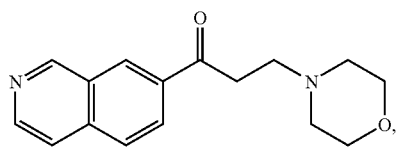
-continued
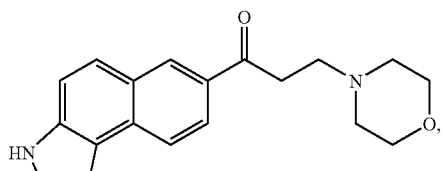
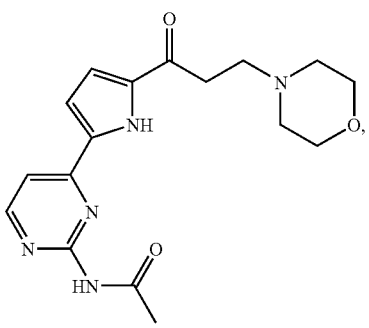
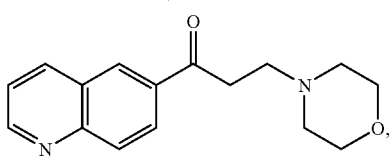
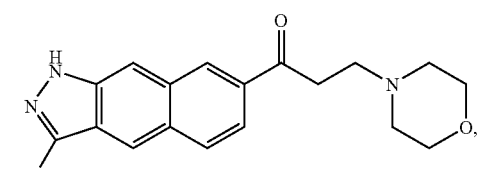
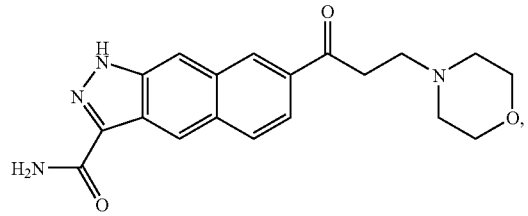
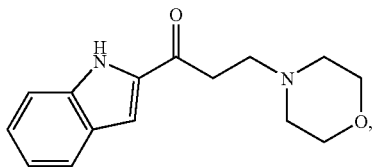
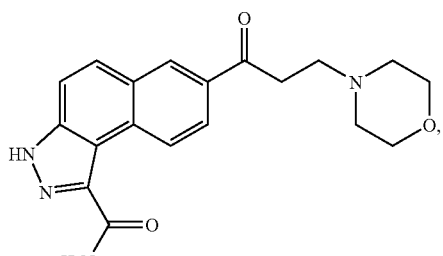
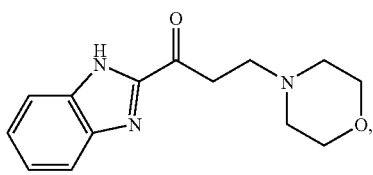

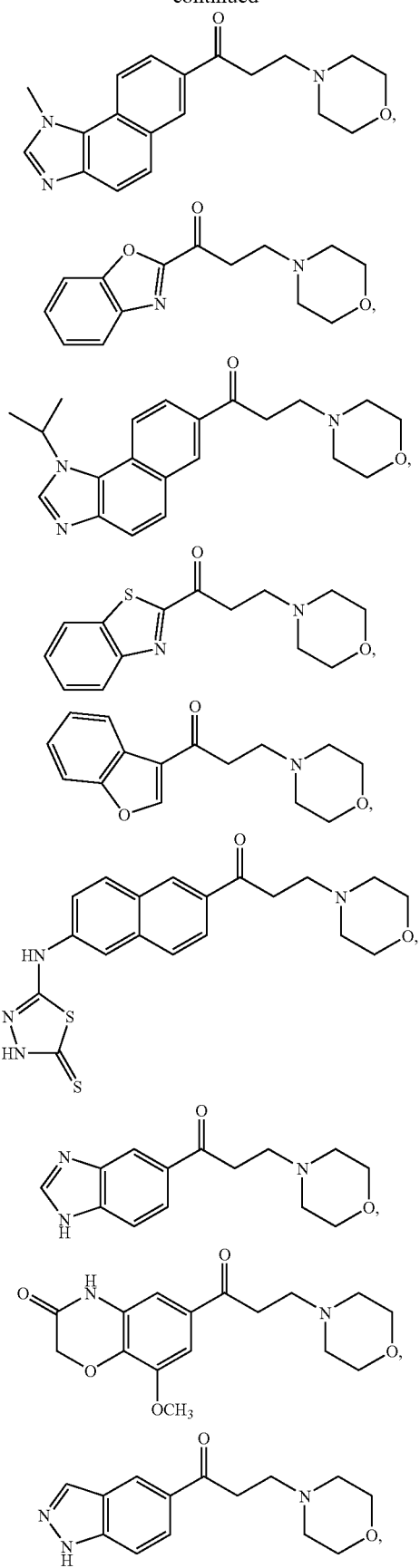
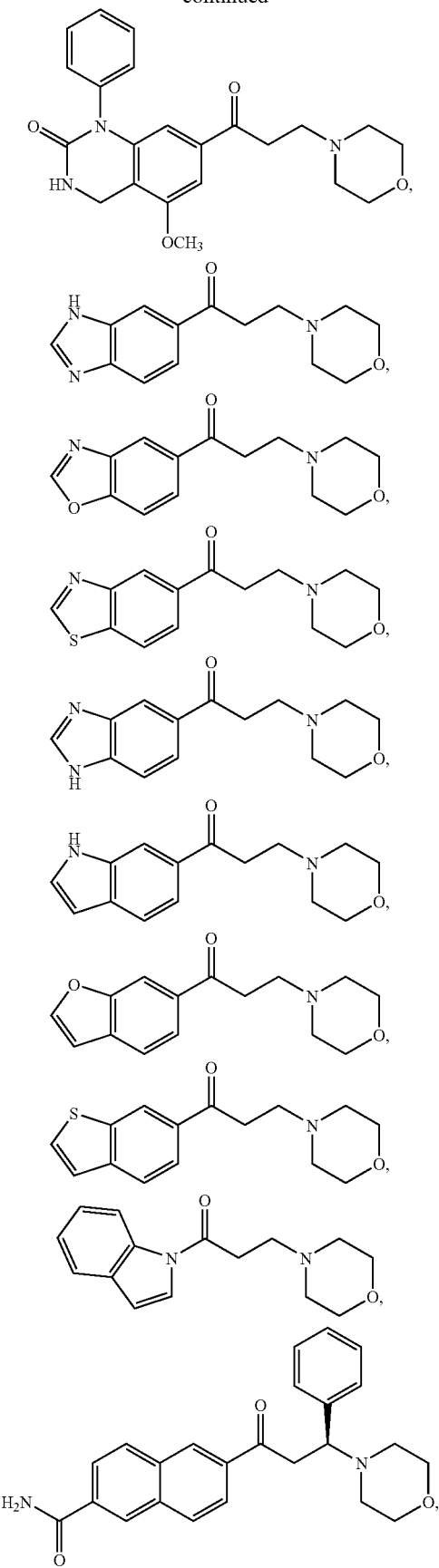

-continued

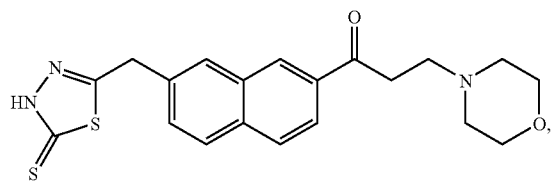

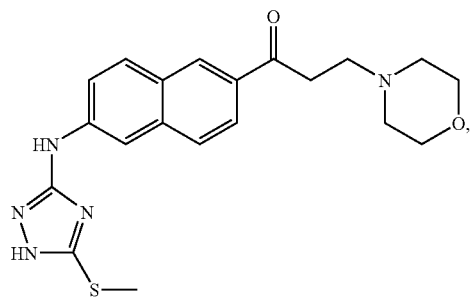

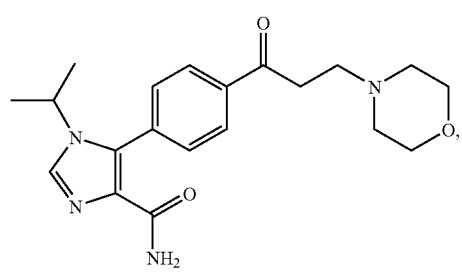

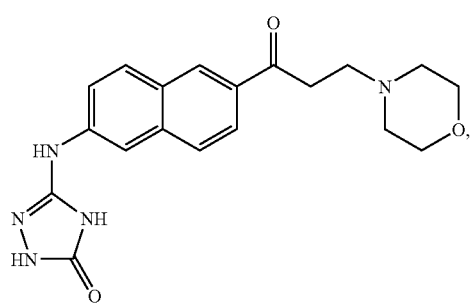

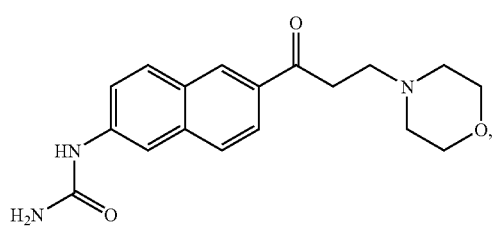

-continued

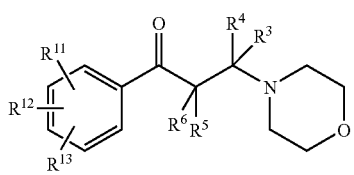

Other compounds have the structural formula:

$$\text{(III)}$$

wherein:

$R^3$, $R^4$, $R^5$, and $R^6$ are as defined above;

$R^{11}$ and $R^{12}$ are independently selected from hydrogen, —OCH$_3$, halogen, —NO$_2$, —CN, —CF$_3$, —NCOR' (wherein R' is hydrogen or $C_1$-$C_4$ alkyl), phenyloxy, —OCF$_3$, —NR'R" (wherein R' and R" are independently hydrogen or $C_1$-$C_4$ alkyl), $C_1$-$C_4$ alkyl, $C_1$-$C_4$ alkoxy, and —SO$_2$R' (wherein R' is hydrogen or $C_1$-$C_4$ alkyl); and $R^{13}$ is hydrogen, $C_1$-$C_4$ alkyl,

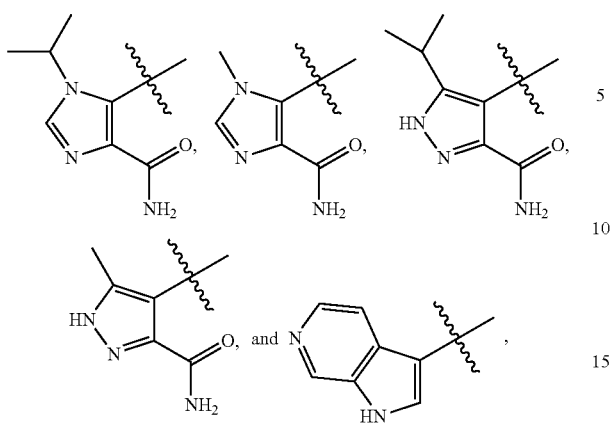
with the proviso that formula (III) does not include the following compounds:
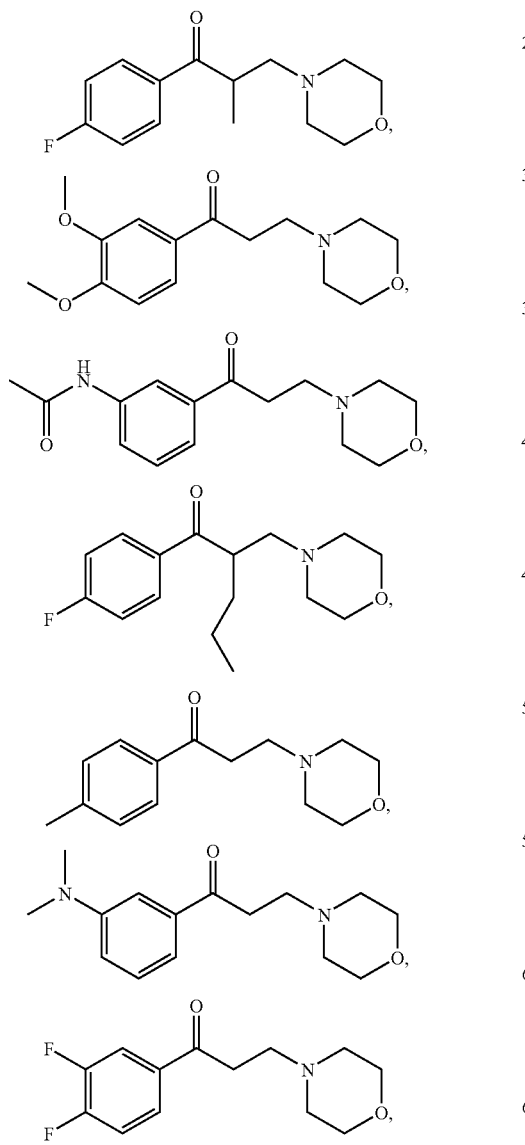
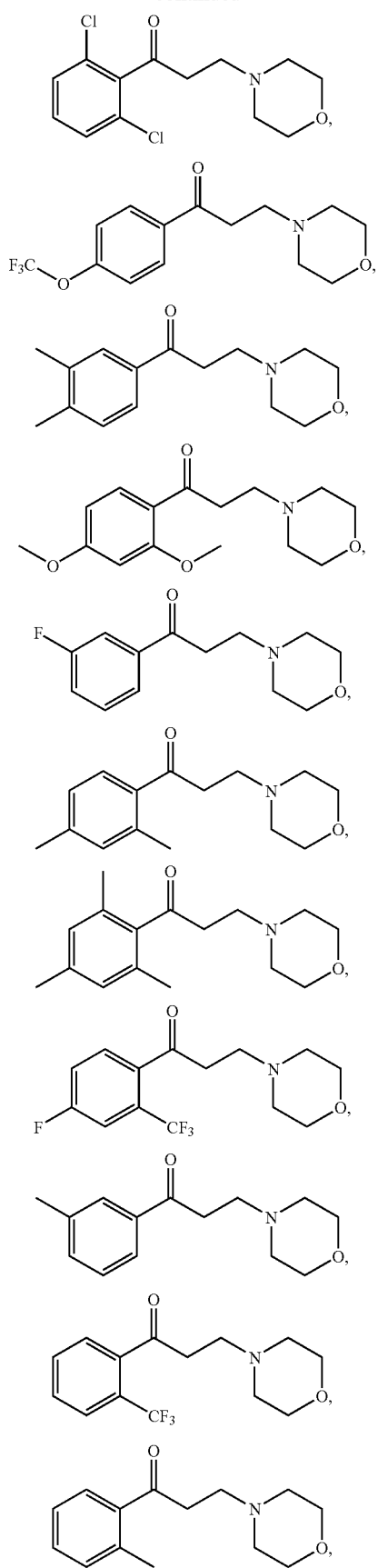

-continued
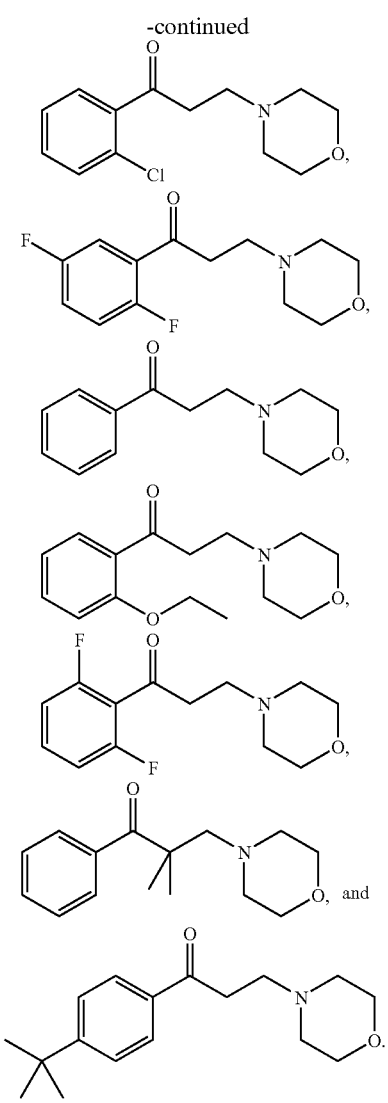
One example of a compound of formula (III) is
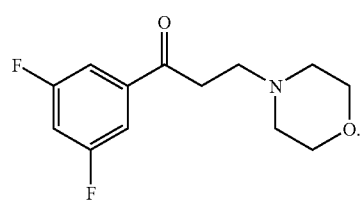 [SMILES: O=C(CCN1CCOCC1)c1cc(F)cc(F)c1]
Some compounds of the invention have the structural formula:
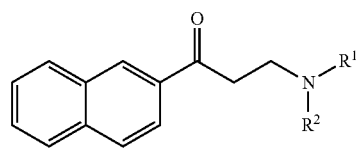
(IV)
wherein $R^1$ and $R^2$ are as defined above, with the exception of
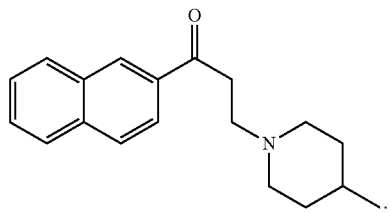 [SMILES: CC1CCN(CCC(=O)c2ccc3ccccc3c2)CC1]
Examples of such compounds include those of with the following structural formulae:
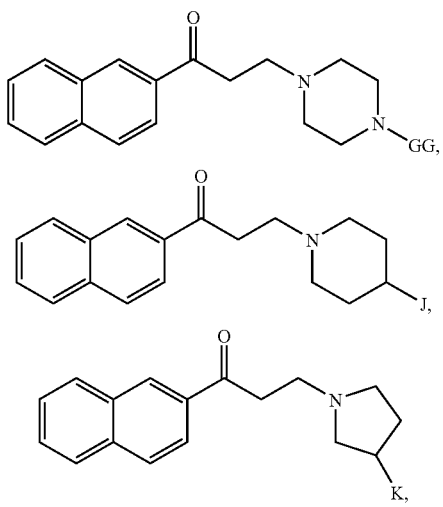
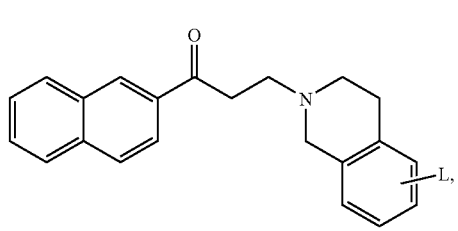
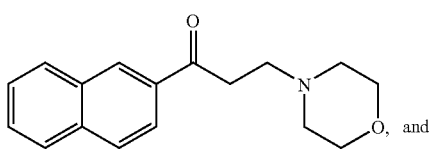
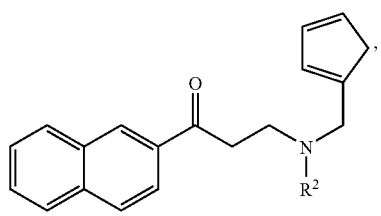

in which:
GG is hydrogen, dimethylaminoalkyl, aryl, $C_1$-$C_6$ alkyl, cyclohexylalkyl, pyridine, —COCF$_3$; —CONR'R", or
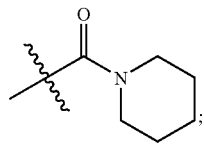 [SMILES: *C(=O)N1CCCCC1]
J is hydrogen, aralkyl, $C_1$-$C_6$ alkyl, —CNHCOOR', or NR'R";
K is hydrogen, pyridine, aryl, —COOH, —CONR'R", —COH, or —CNR'R";
L is hydrogen or alkyloxy; and
$R^2$ is as defined above.
Other compounds of formula (IV) include:
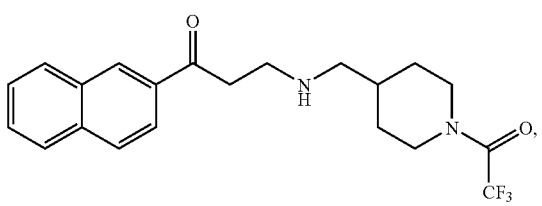
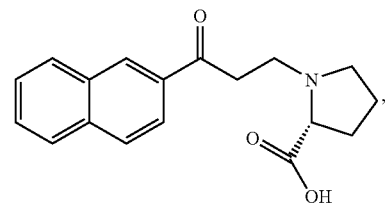
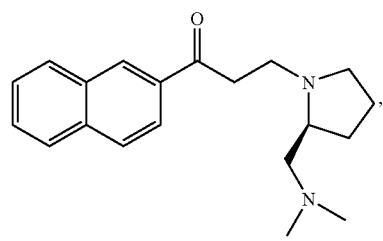
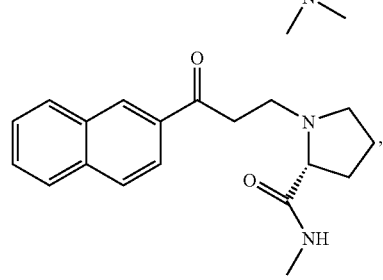
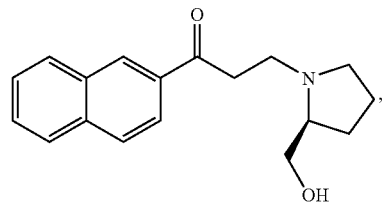
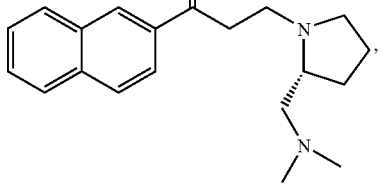
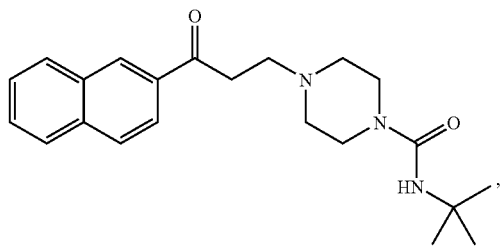
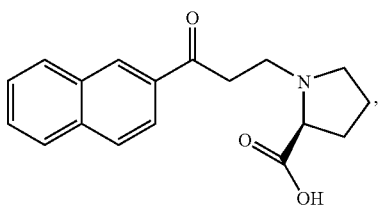
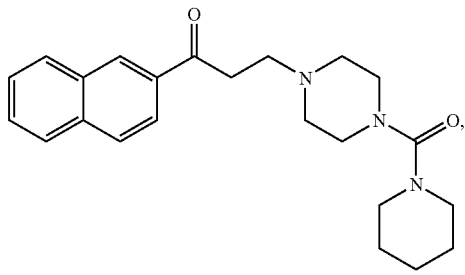
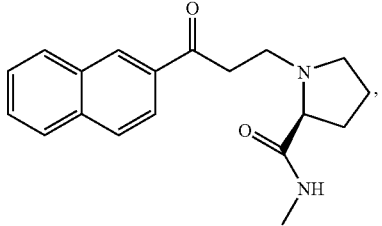
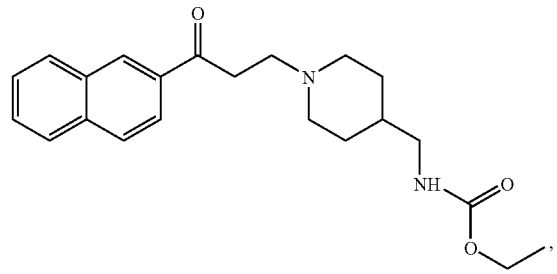
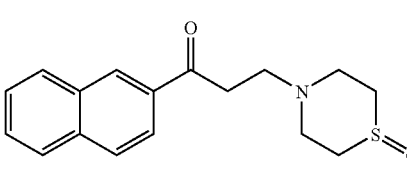
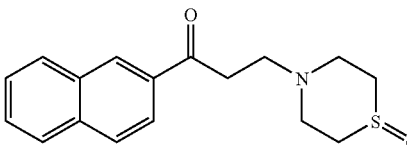

-continued

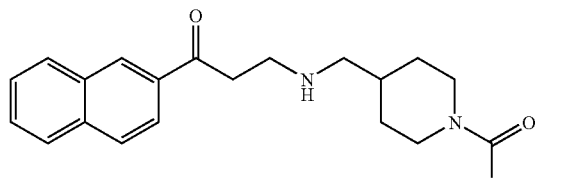

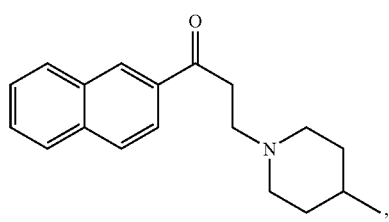

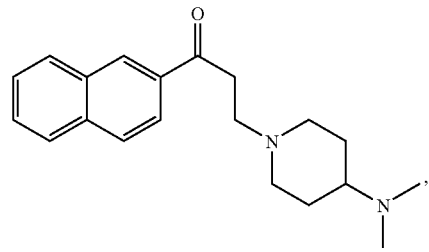

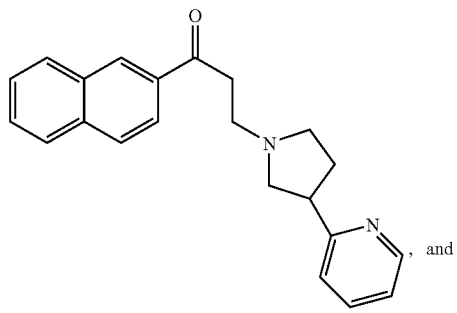

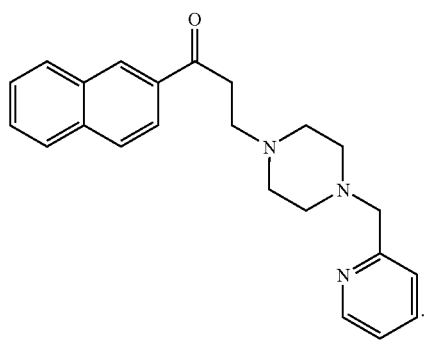, and

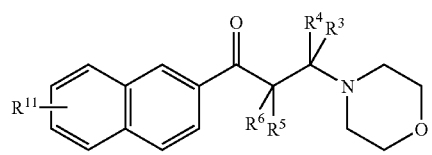

Other compounds have the structural formula:

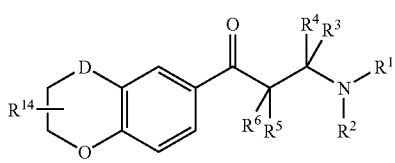

(V)

wherein $R^3$, $R^4$, $R^5$, $R^6$, and $R^{10}$ are as defined above.

Other compounds have the structural formula:

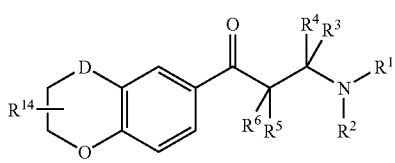

(VI)

wherein:
$R^1$, $R^2$, $R^3$, $R^4$, $R^5$, and $R^6$ are as defined above; and
$R^{14}$ is hydrogen or =O;
and D is CH or NH,
with the exception of:

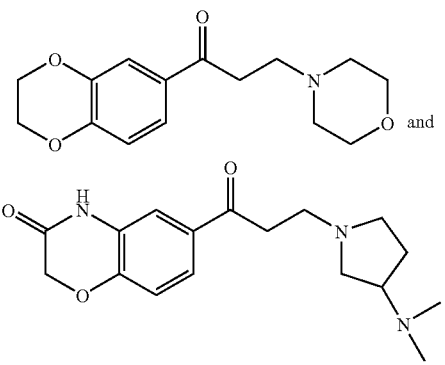

Other compounds have the structural formula:

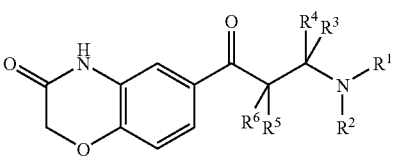

(VII)

wherein:
$R^3$, $R^4$, $R^5$, and $R^6$ are as defined above; and
$R^1$ and $R^2$ are independently hydrogen, $C_1$-$C_4$ alkyl,

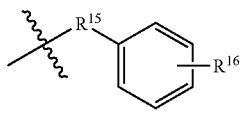

(wherein $R^{15}$ is halogen or $C_1$-$C_4$ alkyl and $R^{16}$ is $C_1$-$C_4$ alkyl), or $R^1$ and $R^2$ together with the nitrogen to which they are attached form an aryl group selected from

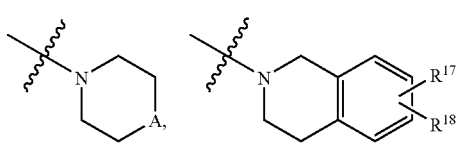

(wherein $R^{17}$ and $R^{18}$ are independently hydrogen or —OCH$_3$),

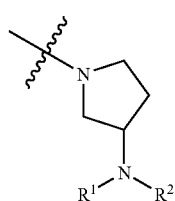

(wherein $R^1$ and $R^2$ are independently hydrogen or $C_1$-$C_4$ alkyl),

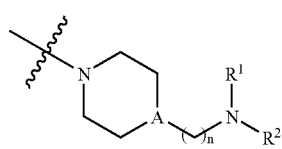

(n=1-4), phenyl-$C_1$-$C_4$ alkyl (optionally substituted with halogen), with the exception of

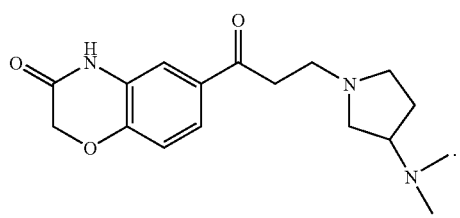 [SMILES: CN(C)C1CCN(CCC(=O)c2ccc3c(c2)NC(=O)CO3)C1]

Other compounds have the structural formula:

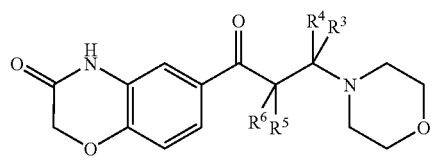

(VIII)

wherein $R^3$, $R^4$, $R^5$, and $R^6$ are as defined above.
Other compounds have the structural formula:

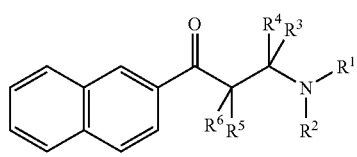

(IX)

wherein $R^3$, $R^4$, $R^5$, and $R^6$ are as defined above and wherein $R^1$ is hydrogen and $R^2$ is

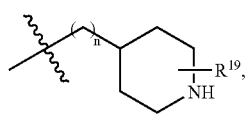

wherein $R^{19}$ is selected from hydrogen and

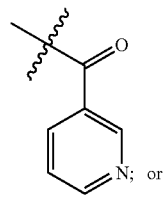 [SMILES: *C(=O)c1cccnc1]

$R^1$ and $R^2$ together with the nitrogen to which they are attached are

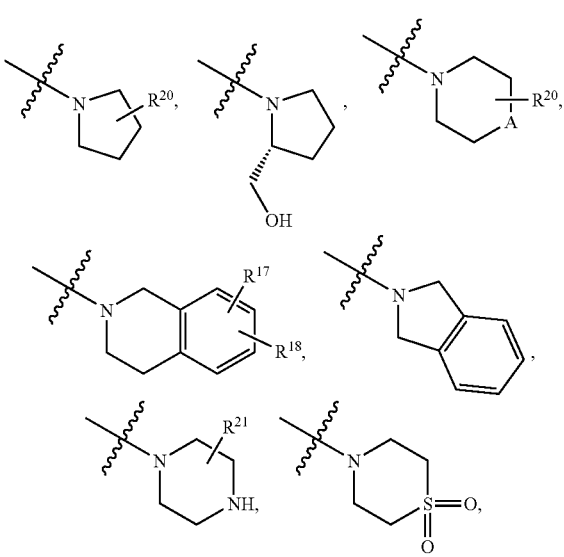

A is N or O;
$R^{20}$ is phenyl-$C_1$-$C_4$ alkyl optionally substituted with one or more halogens, hydrogen, $C_1$-$C_4$ alkyl, amino-$C_1$-$C_4$ alkyl,

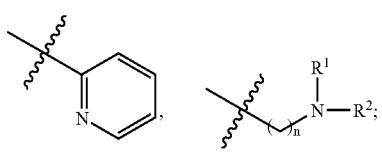

$R^{17}$ and $R^{18}$ are independently hydrogen or —OCH$_3$;
$R^{21}$ is —CONR'R'', —COR',

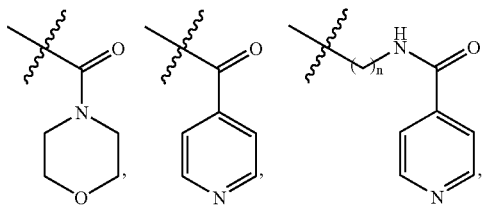

-continued

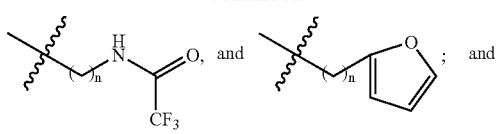

R' and R'' are independently selected from hydrogen and $C_1$-$C_4$ alkyl.

In other embodiments compounds have the structural formula:

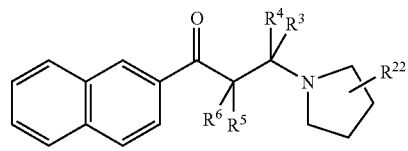
(X)

wherein $R^3$, $R^4$, $R^5$, and $R^6$ are as defined above and wherein $R^{22}$ is selected from hydrogen, $C_1$-$C_4$ alkyl, —NR'R'', —COH, —COOH, —CNR'R'', and —CONHR', wherein R' and R'' are as defined above.

In other embodiments compounds have the structural formula:

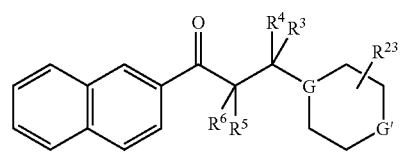
(XI)

wherein $R^3$, $R^4$, $R^5$, $R^6$, G, and G' are as defined above; and $R^{23}$ is hydrogen, —NR'R''$C_1$-$C_4$ linear alkyl, $C_1$-$C_4$ alkyl, phenyl-$C_1$-$C_4$ alkyl, —CONH$_2$, and —COR'R'', wherein R' and R'' are as defined above.

In other embodiments compounds have the structural formula:

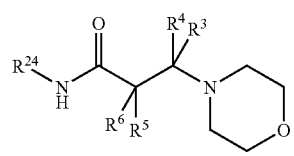
(XII)

$R^3$, $R^4$, $R^5$, and $R^6$ are as defined above and wherein $R^{24}$ is

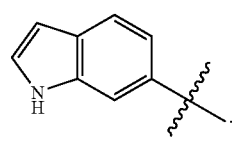 [SMILES: *c1ccc2cc[nH]c2c1]

In other embodiments compounds have the structural formula:

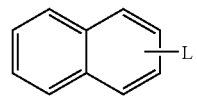
(XIII)

wherein L is

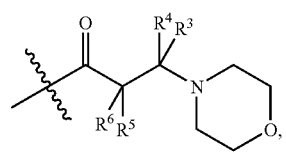

and wherein $R^3$, $R^4$, $R^5$, and $R^6$ are as defined above.

Some compounds have the structural formula:

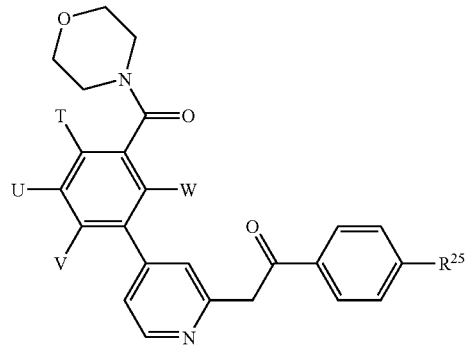
(XIV)

wherein T, U, V, and W independently are selected from hydrogen; halogen; —O; $C_1$-$C_3$ alkyl; and $C_1$-$C_3$ alkyloxy; and wherein $R^{25}$ is hydrogen or $C_1$-$C_3$ alkyl. Representative compounds include:

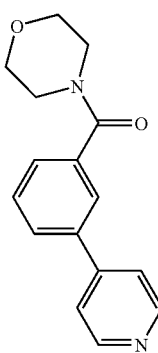

and

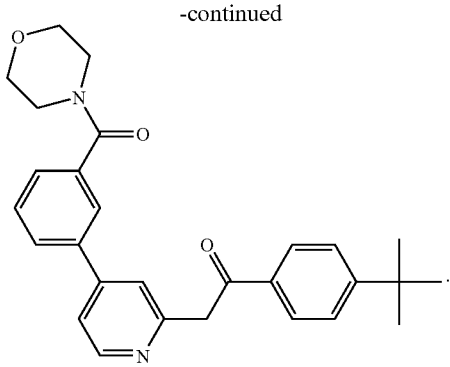

Other compounds have the structural formula:

(XV)

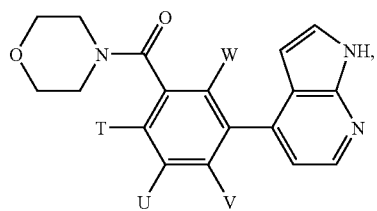

wherein T, U, V, and W independently are selected from hydrogen; halogen; —O; $C_1$-$C_3$ alkyl; and $C_1$-$C_3$ alkyloxy; and wherein $R^8$ is hydrogen or $C_1$-$C_3$ alkyl.

Still other compounds have the structural formula:

(XVI)

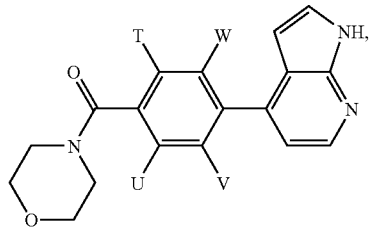

wherein T, U, V, and W independently are selected from hydrogen; halogen; —O; $C_1$-$C_3$ alkyl; and $C_1$-$C_3$ alkyloxy; and wherein $R^8$ is hydrogen or $C_1$-$C_3$ alkyl.

Other compounds have the structural formula:

(XVII)

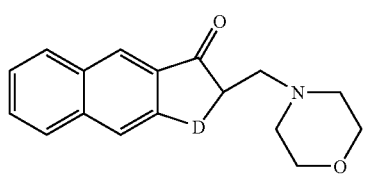

wherein D is S, O, or NH; i.e.,

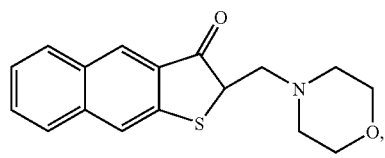

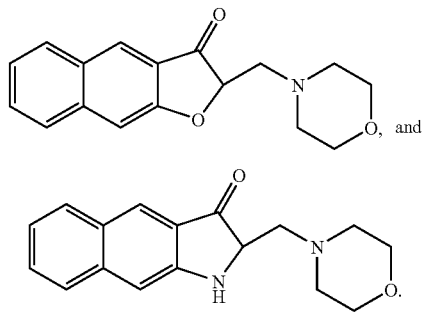

Other compounds of the invention include those with the structural formula:

(XVIII)

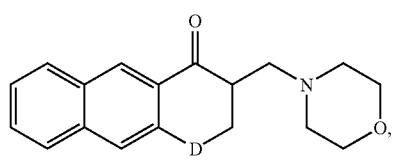

wherein D is defined above; i.e.,

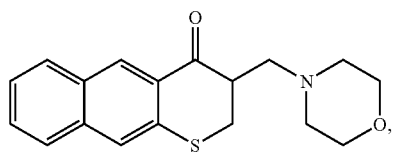

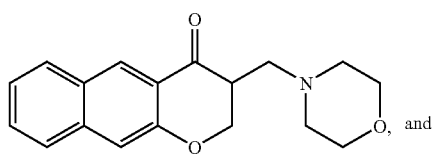

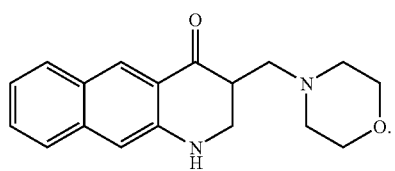

Other compounds of the invention include those with the structural formula:

(XIX)

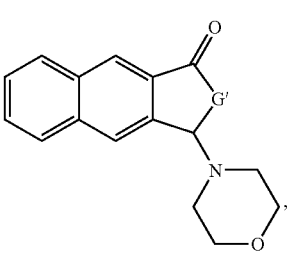

wherein G' is NH or CH; i.e.,

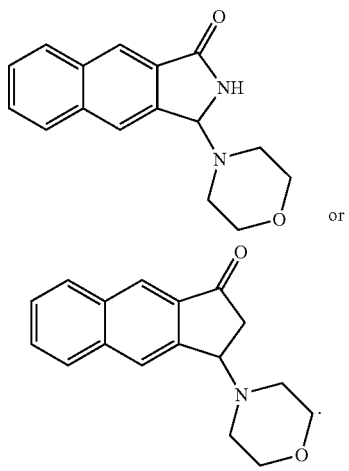

or

The invention also includes the compounds identified in Examples 15 and 16.

The compounds of the present invention may have asymmetric centers and may occur as racemates, stereoisomers, and tautomers. The invention includes all possible racemates, tautomers, stereoisomers, and mixtures thereof.

Suitable methods of preparing compounds of the invention are illustrated by the representative examples provided below. Starting materials are known compounds and can be obtained by standard procedures of organic chemistry.

Provisos for Compound Claims

Compounds of the invention preferably do not have one or more of the following activities: vasodilator, hypotensive, bradycardiac, anti-depressant, anti-arrhythmic, anti-arteriosclerotic, serum cholesterol lowering, triglyceride level lowering, neuroleptic, anti-inflammatory tranquilizing, anti-convulsant, anesthetic, muscle relaxing anti-fungal, anti-bacterial, insecticidal, fumigant, anti-parasitic, central nervous system depressant, antagonization of sedation, anti-pollakiurea, antihistaminie, anti-allergy, bronchodilating, analgesic, spasmolytic, muscarinic antiagonist, preventing or decreasing production of abnormally phosphorylated paired helical filament epitopes associated with Alzheimer's Disease, hypolipidemic, male anti-fertility, anti-sporicidal, inhibition of nitric oxide production, or central nervous system stimulant activities.

To the extent any of the following compounds are not novel, Applicants reserve the right to present compound and/or composition claims which include a proviso excluding the compounds and/or their pharmaceutically acceptable salts from the scope of the claims:

a. compounds having the structural formula:

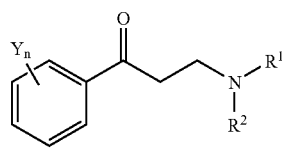

wherein n is 0, 1, 2, or 3 and $R^1$ and $R^2$ together with the nitrogen atom to which they are attached are

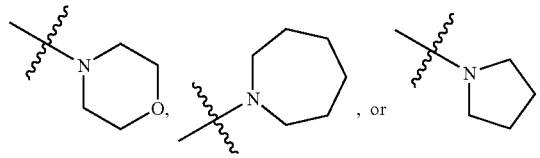

and Y is alkyl, halogen, halogenoalkyl, alkyoxy, akylthio, halogenoalkyloxy, halogenoalkylthio, cycloalkyl, or a cyane radical;

b. compounds of formula (C) in which Ar is phenyl, if $R^3$, $R^4$, $R^5$, and $R^6$ are each hydrogen, and $R^1$ and $R^2$ together form a ring with the nitrogen atom to which they are attached

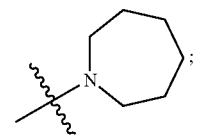 [SMILES: *N1CCCCCC1]

c. compounds having the structural formula:

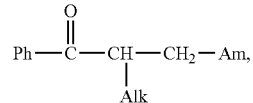

in which Ph is an optionally substituted monocyclic carbocyclic aryl radical, Alk is $C_1$-$C_3$ lower alkyl, and Am is a tertiary amino group, salts, N-oxides, or quaternary ammonium derivatives thereof;

d. compounds having the structural formula:

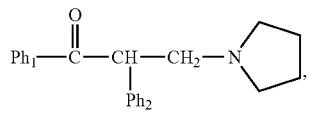

in which $Ph_1$ and $Ph_2$ are monocyclic carboxylic aryl radicals and the acid addition salts thereof;

e. compounds having the structural formula:

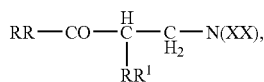

in which RR is selected from the group consisting of aliphatic, aromatic, and araliphatic radicals; $RR^1$ is selected from the group consisting of hydrogen, aliphatic, aromatic, and araliphatic radicals; —N(XX) is the residue of a secondary amine selected from the group consisting of dialkylamine and dialkylamines;

f. compounds having the structural formula:

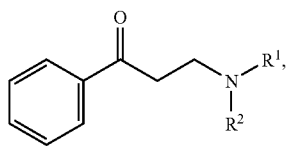

wherein $R^1$ and $R^2$ are as defined in formula (I), including the compound

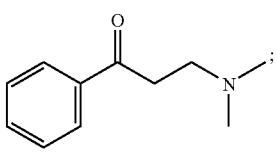

g. compounds having the structural formula:

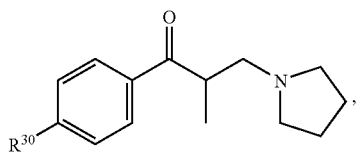

wherein $R^{30}$ is an ethyl-, propyl-, isopropy-, butyl- or isobutyl group or a cycloalkyl group having 5-7 carbon atoms;

h. compounds having the structural formula:

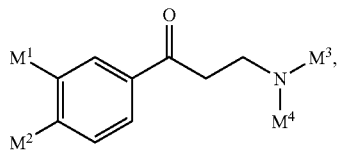

in which $M^2$ is hydrogen, halogen, or $C_1$-$C_{12}$ alkoxy, $M^1$ is hydrogen or halogen, and $M^3$ and $M^4$ are lower alkyl or, taken together with the nitrogen atom to which they are attached, (a) are a heterocyclic amino group or an N-lower alkyl quaternary heterocyclic ammonium group or (b) a tri-lower alkyl-ammonium;

i. compounds having the structural formula:

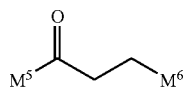

or a picrate salt thereof, wherein $M^5$ is a simple or substituted aryl group and $M^6$ is a simple or substituted amino group;

j. compounds having the structural formula:

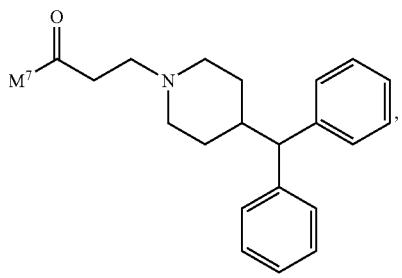

in which $M^7$ is thienyl, phenyl or substituted phenyl;

k. compounds having the structural formula:

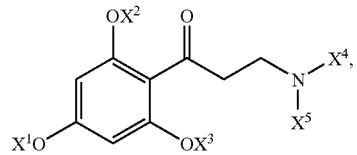

in which each of $X^1$, $X^2$, and $X^3$ are independently hydrogen or an alkyl group, and each of $X^5$ and $X^4$ are independently hydrogen or an alkyl group or, together with the nitrogen atom to which they are attached, form a heterocyclic group with 5, 6, or 7 ring atoms, optionally containing, in addition to N, a further heteroatom selected from N, S, and O;

l. compounds of formula (II) in which $R^9$ is phenyl and $R^3$, $R^4$, $R^5$, and $R^6$ are each hydrogen;

m. compounds having the structural formula:

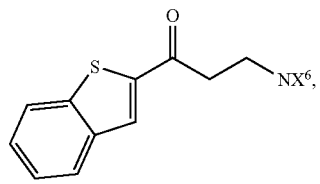

in which $X^6$ forms with the nitrogen atom pyrrolidine, piperidine, morpholine, hexamethyleneimine, or 3-azabicyclo-3,2,2 nonane, including the compound

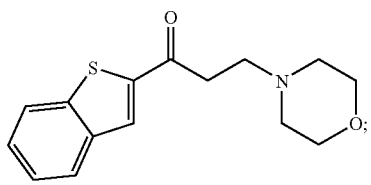 [SMILES: O=C(CCN1CCOCC1)c1cc2ccccc2s1]

n. compounds having the structural formula:

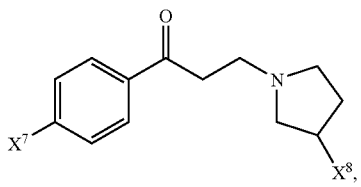

in which $X^7$ is hydrogen or fluorine; $X^8$ is $N(X^9)$phenyl (wherein the phenyl is optionally monosubstituted with $C_1$-$C_8$ alkoxy, $C_1$-$C_8$ alkyl, trifluoromethyl, or halogen), —C(OH)($X^9$)phenyl (wherein the phenyl is optionally monosubstituted with $C_1$-$C_8$ alkoxy, $C_1$-$C_8$ alkyl, trifluoromethyl, or halogen), or phenyl (wherein the phenyl is optionally monosubstituted with $C_1$-$C_8$ alkoxy, $C_1$-$C_8$ alkyl, trifluoromethyl, or halogen); and $X^9$ is hydrogen, $C_1$-$C_8$ alkyl, or lower alkanoyl;

o. compounds having the structural formula:

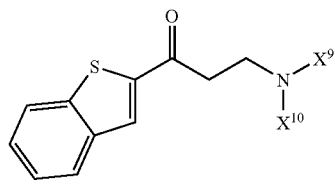

wherein $X^9$ and $X^{10}$ each designate a saturated or unsaturated aliphatic hydrocarbon having 1 to 4 carbon atoms or, together with the nitrogen to which they are attached, form a heterocyclic radical selected from pyrrolidino, piperidine, perhydroazepino, and morpholino;

p. compounds having the structural formula:

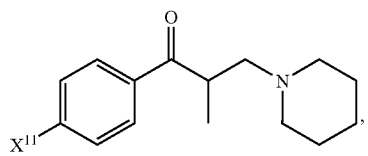

in which $X^{11}$ is $C_2$-$C_3$ alkyl;

q. compounds having the structural formula:

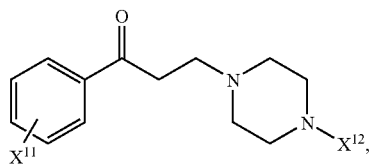

in which $X^{11}$ is hydrogen, halogen, $C_1$-$C_4$ alkoxy, nitro, or $C_1$-$C_4$ secondary amine; $X^{12}$ is $(CH_2)_nOX^{13}$; n is 2 or 3; and $X^{13}$ is $C_1$-$C_4$ alkoxyphenyl, nitrophenyl, trifluoromethylphenyl, or phenyl disubstituted with two halogens, two $C_1$-$C_4$ alkyls, halogen and nitro, halogen and $C_1$-$C_4$ alkyl, halogen and $C_1$-$C_4$ alkoxy, or $C_1$-$C_4$ alkoxy and $C_1$-$C_4$ alkoyl;

r. compounds having the structural formula:

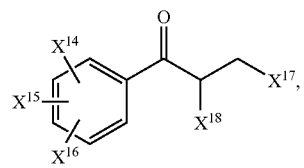

in which $X^{14}$, $X^{15}$, and $X^{16}$ are independently hydrogen, halogen, $C_1$-$C_4$ alkyl, halogeno-$C_1$-$C_4$ alkyl, $C_1$-$C_4$ alkoxy, or a cycloalkyl group having 3-8 carbon atoms and two of $X^{14}$, $X^{15}$, and $X^{16}$ may combine to form methylenedioxy or ethyleneoxy; $X^{18}$ is hydrogen or $C_1$-$C_4$ alkyl; and $X^{17}$ is pyrrolidinyl-, piperidinyl, morpholinyl-, or azepinyl;

s. compounds having the structural formula:

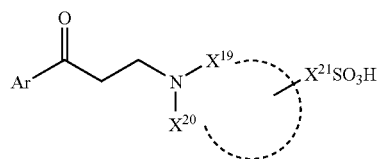

Ar denotes an aryl radical; and $X^{19}$ and $X^{20}$ (a) are both $C_1$-$C_6$ alkyl or (b) together with the N atom form the remaining members of a saturated heterocyclic radical and $X^{21}$ is —OH, $C_1$-$C_6$ alkyl, or aryl;

t. compounds having the structural formula:

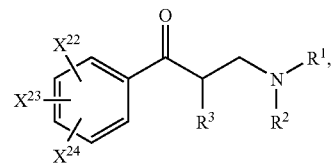

wherein $R^1$ and $R^2$ independently represent an alkyl radical; or $R^1$ and $R^2$, together with the nitrogen atom to which they are bonded complete an optionally substituted heterocyclic radical of the formula

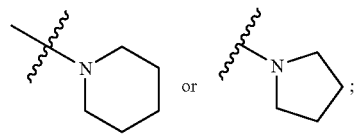

$R^3$ is hydrogen or $C_1$-$C_4$ alkyl; and $X^{22}$, $X^{23}$, and $X^{24}$ are independently $C_1$-$C_4$ alkyl, halogen, or a halogeno-$C_1$-$C_4$ alkyl, $C_1$-$C_4$ alkoxy, alkylthio, halogeno-$C_1$-$C_4$ alkoxy, halogeno-$C_1$-$C_4$ alkylthio, cycloalkyl 3 to 7 carbon atoms, or cyano;

u. compounds having the structural formula:

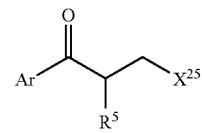

wherein Ar is non-substituted aryl or aryl substituted with a hydroxyl group, lower alkoxy group or halogen, or non-substituted benzo[b]thienyl group or benzo[b]thienyl group substituted by hydroxyl group, lower alkyl group, lower alkoxy group, aryl group or halogen; $R^5$ is hydrogen or $C_1$-$C_4$ alkyl; and $X^{25}$ is a group other than piperidine;

v. compounds having the structural formula:

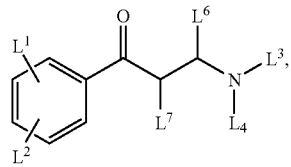

wherein $L^1$ and $L^2$ are independently halogen or alkyl; $L^6$ and $L^7$ are independently hydrogen or alkyl; and $L^3$ and $L^4$ are independently hydrogen or an aliphatic group or combine together with the nitrogen to which they are attached to form a ring;

w. compounds of formula (I), (IV), (VI), (VII), (IX), and (XI) in which if $R^3$ and $R^4$ are hydrogen, then

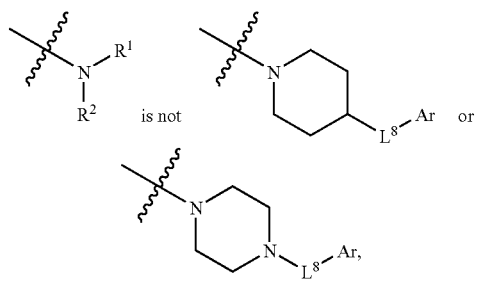

wherein $L^8$ is a carbonyl, sulfonyl, methylene, or methylene substituted with optionally substituted phenyl; and Ar is an aryl group;

x. compounds having the structural formula:

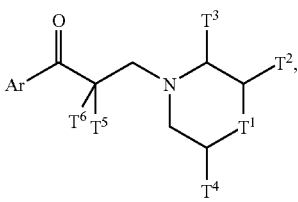

in which $T^1$ is O, S, or $NT^7$; $T^7$ is hydrogen, $C_1$-$C_4$ alkyl, and $CH_2CH_2COAr_1$; $T^6$ is hydrogen. $C_1$-$C_6$ alkyl, or $T^6$ and a substituent on the aryl group together represent $CH_2$, $CH_2CH_2$, $CH_2O$, or $CH_2S$ to form a five or six membered ring where the ring is optionally substituted with substituted phenyl; $T^2$, $T^3$, and $T^4$ are independently hydrogen or $C_1$-$C_6$ alkyl; and Ar and $Ar_1$ are aryl or optionally substituted phenyl; and y. the following compounds:

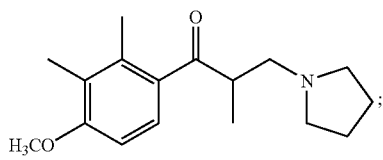

-continued

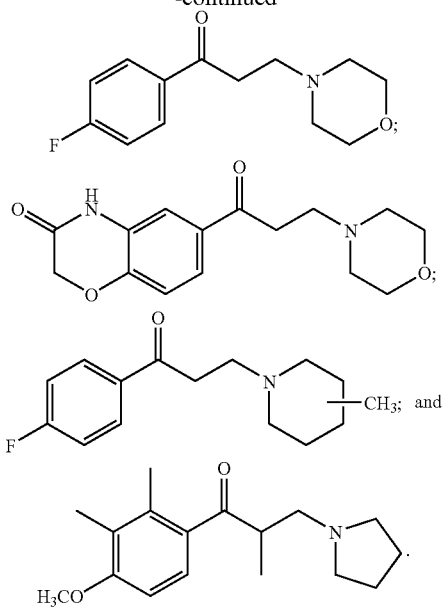

Pharmaceutical Preparations

Compounds of the invention can be formulated as pharmaceuticals using methods well known in the art. Pharmaceutical formulations of the invention typically comprise at least one compound of the invention mixed with a carrier, diluted with a diluent, and/or enclosed or encapsulated by an ingestible carrier in the form of a capsule, sachet, cachet, paper or other container or by a disposable container such as an ampoule.

A carrier or diluent can be a solid, semi-solid or liquid material. Some examples of diluents or carriers which may be employed in the pharmaceutical compositions of the present invention are lactose, dextrose, sucrose, sorbitol, mannitol, propylene glycol, liquid paraffin, white soft paraffin, kaolin, microcrystalline cellulose, calcium silicate, silica polyvinylpyrrolidone, cetostearyl alcohol, starch, gum acacia, calcium phosphate, cocoa butter, oil of theobroma, arachis oil, alginates, tragacanth, gelatin, methyl cellulose, polyoxyethylene sorbitan monolaurate, ethyl lactate, propylhydroxybenzoate, sorbitan trioleate, sorbitan sesquioleate and oleyl alcohol.

Pharmaceutical compositions of the invention can be manufactured by methods well known in the art, including conventional mixing, dissolving, granulating, dragee-making, levigating, emulsifying, encapsulating, entrapping, or lyophilizing processes.

For injection, the agents of the invention may be formulated in aqueous solutions, preferably in physiologically compatible buffers such as acetate, Hanks's solution, Ringer's solution, or physiological saline buffer. Preferably the solutions are sterile and non-pyrogenic. For transmucosal administration, penetrants appropriate to the barrier to be permeated are used in the formulation. Such penetrants are generally known in the art.

For oral administration, the active compound(s) can be combined with pharmaceutically acceptable carriers which enable the compound(s) to be formulated as tablets, pills, dragees, capsules, liquids, gels, syrups, slurries, suspensions and the like. Fillers can be used, such as gelatin, sugars (e.g., lactose, sucrose, mannitol, or sorbitol); cellulose preparations (e.g., maize starch, wheat starch, rice starch, potato starch, gum tragacanth, methyl cellulose, hydroxypropylmethyl-cellulose, sodium carboxymethylcellulose); and/or polyvinylpyrrolidone (PVP). If desired, disintegrating agents may be added, such as the cross-linked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compound(s) may be dissolved or suspended in suitable liquids, such as fatty oils, liquid paraffin, or liquid polyethylene glycols. In addition, stabilizers may be added. All formulations for oral administration preferably are in dosages suitable for such administration.

For buccal administration, the compositions may take the form of tablets or lozenges formulated in conventional manner.

For administration by inhalation, pharmaceutical preparations of the invention can be delivered in the form of an aerosol sprays from pressurized packs or a nebulizer, with the use of a suitable propellant, e.g., dichlorodifluoromethane, trichlorofluoromethane, dichlorotetrafluoroethane, carbon dioxide, or other suitable gas. If desired, a valve can be used to deliver a metered amount. Capsules and cartridges of e.g., gelatin for use in an inhaler or insufflator, may be formulated containing a powder mix of a compound and a suitable powder base such as lactose or starch.

Compounds of the invention can be formulated for parenteral administration by injection, e.g., by bolus injection or continuous infusion. Formulations for injection can be presented in unit dosage form, e.g., in ampoules or in multi-dose containers, with an added preservative. The compositions can take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compounds. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Alternatively, the active ingredient may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa butter or other glycerides.

Compounds of the invention typically are soluble and stable in 50 mM acetate at a concentration of 10 mg/ml or above, and can be delivered intraperitoneally and orally in this buffer. Some compounds are soluble in hydroxypropyl-b-cyclodextrin (HBPCD, 3-5%), and can be delivered intraperitoneally and orally in this solvent. For intravenous delivery, compounds can be suspended or dissolved in 5% mannitol.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

The pharmaceutical compositions also may comprise suitable solid or gel phase carriers or excipients. Examples of such carriers or excipients include but are not limited to, calcium carbonate, calcium phosphate, various sugars, starches, cellulose derivatives, gelatin, and polymers such as polyethylene glycols.

In addition to the common dosage forms set out above, the compounds of the present invention may also be administered by controlled release means and/or delivery devices including ALZET® osmotic pumps which are available from Alza Corporation. Suitable delivery devices are described in U.S. Pat. Nos. 3,845,770; 3,916,899; 3,536,809; 3,598,123; 3,944,064 and 4,008,719.

Therapeutic Methods

The identified compounds can be administered to a human patient, either alone or in pharmaceutical compositions where they are mixed with suitable carriers or excipient(s) at doses to treat or ameliorate blood-related cancers (e.g., lymphomas and leukemias) and autoimmune disorders. Reduction of intracellular kinase activity also is useful to suppress the immune system of transplant patients prior to, during, and/or after transplant.

Lymphomas are malignant growths of B or T cells in the lymphatic system, including Hodgkin's lymphoma and non-Hodgkin's lymphoma. Non-Hodgkin's lymphomas include cutaneous T cell lymphomas (e.g., Sezary syndrome and Mycosis fungoides), diffuse large cell lymphoma, HTLV-1 associated T cell lymphoma, nodal peripheral T cell lymphoma, extranodal peripheral T cell lymphoma, central nervous system lymphoma, and AIDS-related lymphoma.

Leukemias include acute and chronic types of both lymphocytic and myelogenous leukemia (e.g, acute lymphocytic or lymphoblastic leukemia, acute myelogenous leukemia, acute myeloid leukemia, chronic myelogenous leukemia, chronic lymphocytic leukemia, T cell prolymphocytic leukemia, adult T cell leukemia, and hairy cell leukemia).

Autoimmune disorders include systemic lupus erythematosus, anti-phospholipid antibody syndrome, multiple sclerosis, ulcerative colitis, Crohn's disease, rheumatoid arthritis, asthma, Hashimoto's thyroiditis, Reiter's syndrome, Sjögren's syndrome, Guillain-Barré syndrome, myasthenia gravis, large vessel vasculitis, medium vessel vasculitis, polyarteritis nodosa, pemphigus vulgaris, scleroderma, Goodpasture's syndrome, glomerulonephritis, primary biliary cirrhosis, Grave's disease, membranous nephropathy, autoimmune hepatitis, celiac sprue, Addison's disease, polymyositis, dermatomyositis, monoclonal gammopathy, Factor VIII deficiency, cryoglobulinemia, peripheral neuropathy, IgM polyneuropathy, chronic neuropathy, autoimmune hemolytic anemia, autoimmune thrombocytopenic purpura, pernicious anemia, ankylosing spondylitis, vasculitis, inflammatory bowel disease, and type I diabetes mellitus. The autoimmune disease may involve a secretory cell, such as a T lymphocyte, B lymphocyte, Mast cell, or dendritic cell. Compounds of the invention also can be used to treat patients who undergo protein replacement therapies and who develop antibodies to the replacement.

Routes of Administration

Pharmaceutical preparations of the invention can be administered locally or systemically. Suitable routes of administration include oral, pulmonary, rectal, transmucosal, intestinal, parenteral (including intramuscular, subcutaneous, intramedullary routes), intranodal, intrathecal, direct intraventricular, intravenous, intraperitoneal, intranasal, intraocular, transdermal, topical, and vaginal routes. As described in more detail above, dosage forms include, but are not limited to, tablets, troches, dispersions, suspensions, suppositories, solutions, capsules, creams, patches, minipumps and the like. Targeted delivery systems also can be used (for example, a liposome coated with target-specific antibody).

Dosage

A pharmaceutical composition of the invention comprises at least one active ingredient in a therapeutically effective amount. A "therapeutically effective dose" is the amount of an active agent which, when administered to a patient, results in a measurable improvement in a characteristic of the disease being treated (e.g., improved laboratory values, retarded development of a symptom, reduced severity of a symptom, improved levels of a biological marker such as CD25a or IL2). The improvement can be evident after a single administration of the therapeutically effective dose. More usually multiple administrations are utilized in order to achieve or maintain optimal effect. In preferred embodiments frequency of administration can range from twice a month to once a week to several times a day, for example 1-4 times a day. In alternative embodiments administration can be by time-release formulations, or extended or continuous infusions. The frequency of administration can be selected to achieve a systemic or local concentration at or above some predetermined level for a period of time. The period of time can be all or a substantial portion of the interval between administrations or comprise the period of time-release or infusion. In some embodiments, the treatment schedule can require that a concentration of the compound be maintained for a period of time (e.g., several days or a week) and then allowed to decay by ceasing administration for a period of time (e.g., 1, 2, 3, or 4 weeks).

Determination of therapeutically effective amounts is well within the capability of those skilled in the art. A therapeutically effective dose initially can be estimated from in vitro enzyme assays, cell culture assays and/or animal models. For example, a dose can be formulated in an animal model to achieve a circulating concentration range that includes the $IC_{50}$ as determined in an in vitro enzyme assay or in a cell culture (i.e., the concentration of the test compound which achieves a half-maximal inhibition of ITK or BTK activity). Such information can be used to more accurately determine useful doses in humans.

Appropriate animal models for the relevant diseases are known in the art. See, e.g., *Exp Hematol.* 34, 284-88, 2006 (aggressive systemic mastocytosis and mast cell leukemia); *Leuk. Lymphoma.* 47, 521-29, 2006 (acute myeloid leukemia); *Leuk. Lymphoma.* 7, 79-86, 1992 (disseminated human B-lineage acute lymphoblastic leukemia and non-Hodgkins lymphoma); *J. Virol.* 79, 9449-57, 2006 (adult T-cell leukemia); *Neoplasia* 7, 984-91, 2005 (lymphoma); *Oligonucleotides* 15, 85-93, 005 (lymphoma); *Transfus. Apher. Sci.* 32, 197-203, 2005 (cutaneous T cell lymphoma); *Nature* 17, 254-56, 1991 (follicular lymphoma and diffuse large cell lymphoma); *Cell. Mol. Immunol.* 2, 461-65, 2005 (myasthenia gravis); *Proc. Natl. Acad. Sci. USA* 102, 11823-28, 2005 (type I diabetes); *Arthritis Rheum.* 50, 3250-59, 2004 (lupus erythymatosus); *Clin. Exp. Immunol.* 99, 294-302, 1995 (Grave's disease); *J. Clin. Invest.* 116, 905-15, 2006 (multiple sclerosis); *Pharmacol Res*. e-published Feb. 1, 2006 (ulcerative colitis); *J. Pathol.* e-published Mar. 21, 2006 (Crohn's disease); *J. Clin. Invest.* 116, 961-973, 2006 (rheumatoid arthritis); *Endocrinol.* 147, 754-61, 2006 (asthma); *Exp Mol Pathol.* 77, 161-67, 2004 (Hashimoto's thyroiditis); *J. Rheumatol. Suppl.* 11, 114-17, 1983 (Reiter's syndrome); *Rheumatol.* 32, 1071-75, 2005 (Sjögren's syndrome); *Brain Pathol.* 12, 420-29, 2002 (Guillain-Barré syndrome); *J. Clin. Invest.* 110, 955-63, 2002 (vessel vasculitis); *Vet. Pathol.* 32, 337-45, 1995 (polyarteritis nodosa); *Immunol. Invest.* 3, 47-61, 2006 (pemphigus vulgaris); *Arch. Dermatol. Res.* 297, 333-44, 2006 (scleroderma); *J. Exp. Med.* 191, 899-906, 2000 (Goodpasture's syndrome); *J. Vet. Med. Sci.* 68, 65-68, 2006 (glomerulonephritis); *Liver Int.* 25, 595-603, 2005 (primary biliary cirrhosis); *Clin. Exp. Immunol* 99, 294-302, 1995 (Grave's disease); *J. Clin. Invest.* 91, 1507-15, 1993 (membranous nephropathy); *J. Immunol.* 169, 4889-96, 2002 (autoimmune hepatitis); *Isr. J. Med. Sci.* 15, 348-55, 1979 (celiac sprue); *Surgery* 128, 999-1006, 2000 (Addison's disease); *J. Neuroimmunol.* 98, 130-35, 1999 (polymyositis); *Am. J. Pathol.* 120, 323-25, 1985 (dermatomyositis); *Bone* 20, 515-20, 1997 (monoclonal gammopathy); *Haemophilia* 11, 227-32, 2005 (Factor VIII deficiency); *Proc. Natl. Acad. Sci. USA* 94, 233-36, 1997 (cryoglobulinemia); *Pain* 110, 56-63, 2004 (peripheral neuropathy); *Ann. Neurol.* 49, 712-20, 2001 (IgM polyneuropathy); *J. Neurosci. Res.* 44, 58-65, 1996 (chronic neuropathy); *Eur. J. Immunol.* 32, 1147-56, 2002 (autoimmune hemolytic anemia); *Haematologica* 88, 679-87, 2003 (autoimmune thrombocytopenic purpura); *Curr. Top. Microbiol. Immunol.* 293, 153-77, 2005 (pernicious anemia); *J. Immunol.* 175, 2475-83, 2005 (ankylosing spondylitis); *Inflamm. Res.* 53, 72-77, 2004 (vasculitis); *Vet. Pathol* 43, 2-14, 2006 (inflammatory bowel disease); and *J. Biol. Chem.* 276, -13821, 2001 (anti-phospholipid antibody syndrome).

$LD_{50}$ (the dose lethal to 50% of the population) and the $ED_{50}$ (the dose therapeutically effective in 50% of the population) can be determined by standard pharmaceutical procedures in cell cultures and/or experimental animals. Data obtained from cell culture assays or animal studies can be used to determine initial human doses. As is known in the art, the dosage may vary depending upon the dosage form and route of administration used.

As is well known, the FDA guidance document "Guidance for Industry and Reviewers Estimating the Safe Starting Dose in Clinical Trials for Therapeutics in Adult Healthy Volunteers" (HFA-305) provides an equation for use in calculating a human equivalent dose (HED) based on in vivo animal studies. Based on the studies described in Example 16, below, the human equivalent dose ranges between 1.5 mg/kg and 8 mg/kg, with some compounds showing considerable efficacy at lower or higher doses than those estimated by the HED. Thus, human dosages for systemic administration can range from, e.g., 1.5 mg/kg to 3 mg/kg; 2 mg/kg to 4 mg/kg; 5 mg/kg to 7 mg/kg; and 4 mg/kg to 8 mg/kg. The amount of composition administered will, of course, be dependent on the subject being treated, on the subject's weight, the severity of the disorder, the manner of administration and the judgment of the prescribing physician.

All patents, patent applications, and references cited in this disclosure are expressly incorporated herein by reference.

The above disclosure generally describes the present invention. A more complete understanding can be obtained by reference to the following specific examples, which are provided for purposes of illustration only and are not intended to limit the scope of the invention.

EXAMPLE 1

Preparation of 1-naphthalen-2-yl-prop-2-en-1-ol

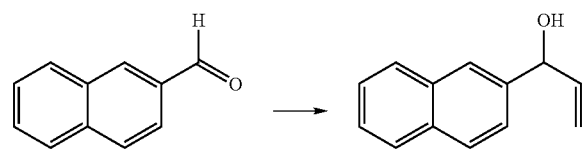

Naphthaldehyde (5.0 g, 32.0 mmole) was dissolved in anhydrous tetrohydrofuran and stirred at −78° C. under $N_2$ (g) atmosphere. To the mixture was added vinyl magnesium bromide (50 ml, 1 M solution in THF) and the reaction was warmed to room temperature and stirred overnight. The reaction was quenched with water and partitioned between EtOAc and water. The organic layer was washed with brine, dried over sodium sulfate, filtered, and concentrated under vacuum to give the desired product as yellow oil (5.0 g, 85%). ESI-MS m/z 185 (M+H)$^+$.

EXAMPLE 2

Preparation of 1-naphthalen-2-yl-propenone

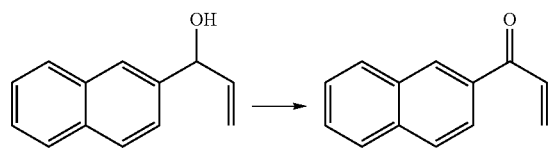

To a solution of 1-naphthalen-2-yl-prop-2-en-1-ol (1.3 g, 7.0 mmole) in 30 ml of dichloromethane was added pyridinium chlorochromate (1.5 g, 7.0 mmole). The mixture was stirred at room temperature until oxidation was complete. The solution was filtered through celite and the solvent was concentrated under vacuum. The residue was redissolved in EtOAc and washed with water and brine, dried over sodium sulfate, filtered, and concentrated under vacuum. The residue was purified by HPLC using a 0-100% EtOAc-Hx gradient to give the desired product as yellow oil (280 mg, 22%). ESI-MS m/z 183 (M+H)$^+$.

EXAMPLE 3

Preparation of 1-naphthalen-2-yl-3-piperidin-1-yl-propan-1-one

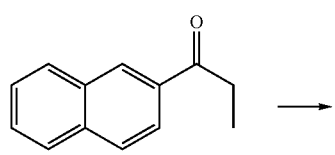

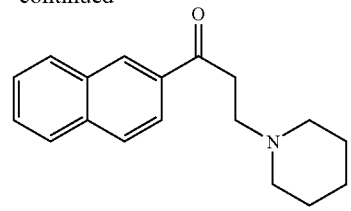

1-Naphthalen-2-yl-propenone (10 mg, 0.05 mmole) was dissolved in 100 μl of DMSO in one well of a 96 well polypropylene plate. To the mixture was added piperidine (12 μl, 0.10 mmole) and diisopropylethyl amine (17 μl, 0.1 mmole). After completion, the product was purified using HPLC to give the desired product (50 mm×10 mm Phenomenex GEMINI™ column using a 30-100% acetonitrile-water gradient). ESI-MS m/z 268 (M+H)$^+$.

EXAMPLE 4

Preparation of 1H-Pyrrolo[2,3-b]pyridine 7-oxide

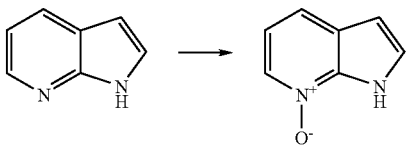 [SMILES: c1cnc2[nH]ccc2c1 ; [O-][n+]1cccc2cc[nH]c21]

7-Azaindole (10 g, 84.7 mmol) was dissolved in ether (300 mL) at room temperature. M-CPBA (29.1 g, 1.5 eq.) was added in portions and stirred by manual agitation. After all oxidant was added, the mixture was stirred at room temperature for a further 3 hours. LC/MS showed complete conversion. The mixture was filtered, and the solid was washed with ether (40 mL×3) and air-dried. NMR analysis of this solid in d6-DMSO obtained showed the product as mostly the meta-Chloro benzoic acid salt of 1H-Pyrrolo[2,3-b]pyridine 7-oxide (off white, 17.9 g); MS: m/z 135.3 [MH$^+$].

EXAMPLE 5

Preparation of 4-Chloro-1H-pyrrolo[2,3-b]pyridine

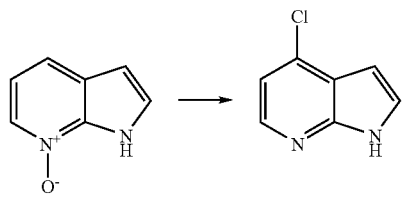 [SMILES: [O-][n+]1cccc2cc[nH]c21 ; Clc1ccnc2[nH]ccc12]

The m-CBA salt of 1H-Pyrrolo[2,3-b]pyridine 7-oxide (9 g) was taken into POCl$_3$ (46 mL, 7.5 eq.). The mixture was heated at 90° C. for 15 hours and to 106° C. for another 4 hours. The mixture was cooled to room temperature, and most of the POCl$_3$ was distilled off under high vacuum. The residue was dissolved in CH$_3$CN (10 mL). Water (20 mL) was added slowly to quench the reaction. The resulted mixture was adjusted to pH 9 using 10 N NaOH. The solid was filtered. The crude solid was redissolved in several ml of THF and combiflashed using 0-10% MeOH in DCM to give 4-Chloro-1H-pyrrolo[2,3-b]pyridine as a slightly yellowish solid. (4 g). MS: m/z 154.9 [MH+].

EXAMPLE 6

Preparation of 1-[4-(1H-Pyrrolo[2,3-b]pyridin-4-yl)-phenyl]-ethanone

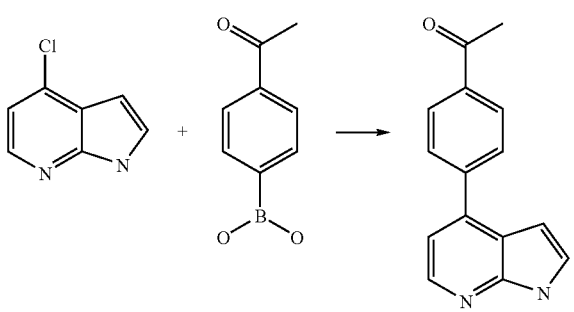 [SMILES: Clc1ccnc2[nH]ccc12 ; CC(=O)c1ccc(B(O)O)cc1 ; CC(=O)c1ccc(-c2ccnc3[nH]ccc23)cc1]

4-Chloro-1H-pyrrolo[2,3-b]pyridine (500 mg, 3.27 mmol) was dissolved in dioxane (11 mL). 4-Acetyl phenylboronic acid (802 mg, 4.9 mmol, 1.5 eq), dppfPdCl$_2$ (41 mg, 0.03 mmol, 0.01 eq) and Na$_2$CO$_3$ (2 N aq., 8.6 mL) were charged. The mixture was vacuumed and flushed with N$_2$ and microwaved at 160° C. for 15 minutes. Six batches of this same reaction were carried out. The crude mixture was pooled and partitioned between DCM (40 mL) and water (20 mL). Combi-flash of the residue using hexane/EtOAc (0% to 100%) gave the free base azaindole derivative as a slightly yellowish solid. The solid was redissolved in DCM (20 mL) and stirred in an ice bath. A 2M HCl solution in ether (10 mL) was added dropwise. The precipitate was filtered and dried to give 1-[4-(1H-Pyrrolo[2,3-b]pyridin-4-yl)-phenyl]-ethanone. (2.5 g, 48%). MS: m/z 237.3 [MH+].

EXAMPLE 7

Preparation of 1-[3-(2-Chloro-pyridin-4-yl)-phenyl]-ethanone

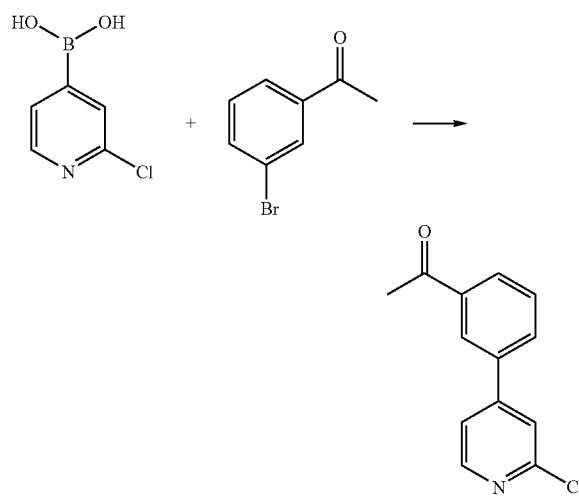

2-Chloropyridine-4-boronic acid (11.0 g, 69.9 mmol), 3-Bromoacetophenone (11.2 mL, 83.9 mmol, 1.2 eq.), Na$_2$CO$_3$ (35 mL, 244.65 mmol, 3.5 eq.) and dppfPdCl$_2$ (572 mg, 0.07 mmol, 0.01 eq.) were mixed in THF (200 mL). The mixture was heated to reflux and continued at this temperature for 6 hours. It was then cooled and concentrated in vacuo. The residue was partitioned between DCM and water (100 mL/40 mL). The layers were separated and the aqueous layer was washed further with DCM (2×40 mL). The combined organic layer was dried (Na$_2$SO$_4$) and filtered. The filtrate was concentrated, and the residue was chromatographed using 1/1 hexane/EtOAc to give 1-[3-(2-Chloro-pyridin-4-yl)-phenyl]-ethanone as a white solid (9.5 g, 58%). MS: m/z 232.1 [MH+].

EXAMPLE 8

Preparation of N-[4-(3-Acetyl-phenyl)-pyridin-2-yl]-benzamide

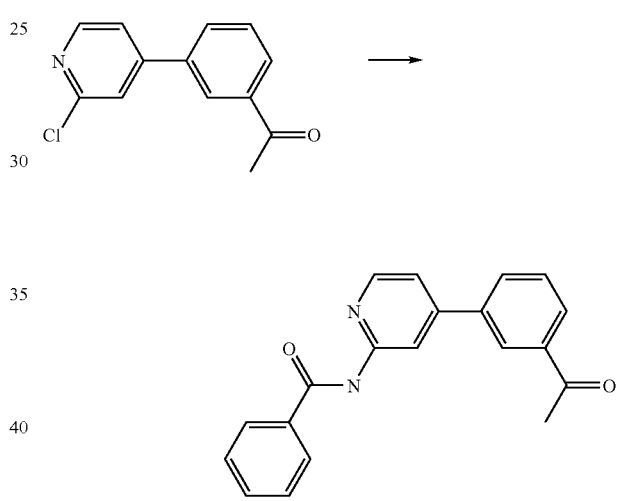

A degassed mixture of 1-[3-(2-Chloro-pyridin-4-yl)-phenyl]-ethanone (500 mg, 2.16 mmol), benzamide (523 mg, 4.32 mmol, 2 eq.), Xantphos (120 mg, 0.21 mmol, 0.1 eq.), Pd(OAc)$_2$ (24 mg, 0.10 mmol, 0.05 eq.), K$_2$CO$_3$ (448 mg, 3.24 mmol, 1.5 eq.) in dioxane (12 mL) was irradiated with microwaves at 150° C. for 1 hour. LC/MS control. Conversion was mostly 100% based on disappearance of starting material. Dimer (M+: 392) being the major by-product. If any starting material is unreacted at this point, another portion of Xantphos and Pd(OAc)$_2$ may be added and the mixture microwaved for another 30 minutes. The mixture was then partitioned between DCM and water (20 mL/10 mL). The layers were separated and the aqueous layer was washed further with DCM (2×20 mL). The combined organic layer was dried (Na$_2$SO$_4$) and filtered. The filtrate was concentrated and the residue was chromatographed using 1/1 Hexane/EtOAc to give N-[4-(3-Acetyl-phenyl)-pyridin-2-yl]-benzamide as a white solid (375 mg, 55%). MS: m/z 317.1 [MH+].

EXAMPLE 9

Preparation of N-{4-[3-(3-Morpholin-4-yl-propionyl)-phenyl]-pyridin-2-yl}-benzamide

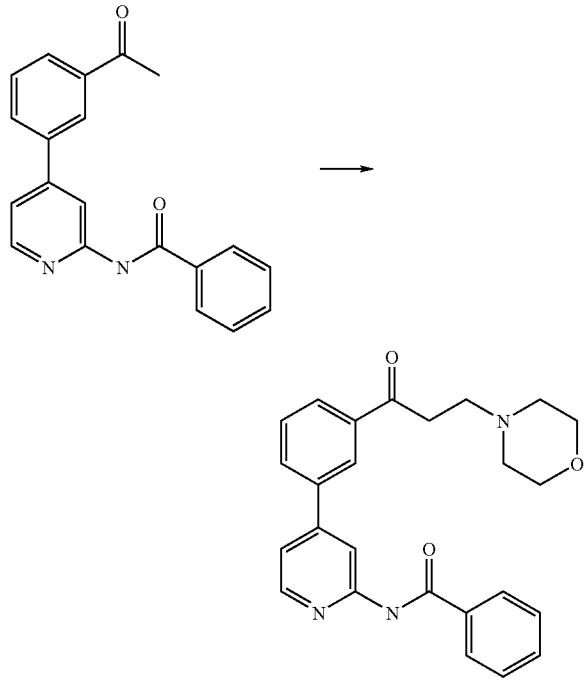

N-[4-(3-Acetyl-phenyl)-pyridin-2-yl]-benzamide (200 mg, 0.632 mmol), morpholine HCl salt (78 mg, 0.632 mmol, 1 eq.) and paraformaldehyde (19 mg, 0.632 mmol, 1 eq.) were mixed with dioxane (2 mL) in a microwave tube. It was irradiated at 180° C. for 15 minutes. The mixture was partitioned between DCM/water (10 mL/5 mL). The aqueous layer was washed further with DCM (2×10 mL). The combined organic layer was dried (Na₂SO₄) and filtered. The filtrate was concentrated and the residue was chromatographed using 20/1 DCM/MeOH to give N-{4-[3-(3-Morpholin-4-yl-propionyl)-phenyl]-pyridin-2-yl}-benzamide as a slightly yellow solid (100 mg, 38%). MS: m/z 416.3 [MH⁺].

EXAMPLE 10

Preparation of 1-[3-(2-Amino-pyridin-4-yl)-phenyl]-3-morpholin-4-yl-propan-1-one

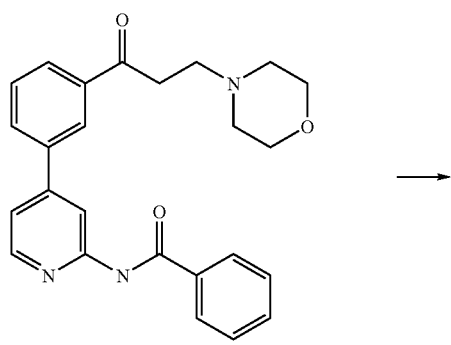

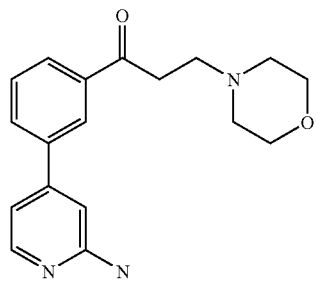

N-{4-[3-(3-Morpholin-4-yl-propionyl)-phenyl]-pyridin-2-yl}-benzamide (100 mg, 0.32 mmol) was dissolved in HCl (2 mL, 6 N). The mixture was irradiated with microwaves at 140° C. for 30 minutes. The mixture was diluted with DCM (20 mL) and neutralized with NaOH to pH 9. The layers were separated and the aqueous layer was washed further with DCM (2×15 mL). The combined organic layer was dried (Na₂SO₄) and filtered. The filtrate was concentrated and the residue was purified to give 1-[3-(2-Amino-pyridin-4-yl)-phenyl]-3-morpholin-4-yl-propan-1-one (TFA salt) as a white solid (84 mg, 78%). MS: m/z 312.3 [MH⁺].

EXAMPLE 11

Preparation of N-[4-(3-Acetyl-phenyl)-pyridin-2-yl]-4-tert-butyl-benzamide

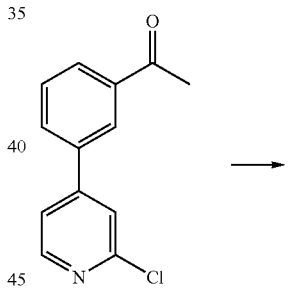

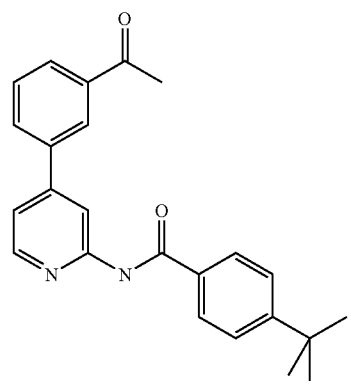

According the same procedure for the preparation of N-[4-(3-Acetyl-phenyl)-pyridin-2-yl]-benzamide, N-[4-(3-Acetyl-phenyl)-pyridin-2-yl]-4-tert-butyl-benzamide (130 mg, 81%, slight impurity) was obtained from 1-[3-(2-Chloropyridin-4-yl)-phenyl]-ethanone (100 mg, 0.43 mmol) and 4-tert-butylbenzamide (153 mg, 0.86 mmol). MS: m/z 373.1 [MH⁺].

EXAMPLE 12

Preparation of 4-tert-Butyl-N-{4-3-(3-morpholin-4-yl-propionyl)-phenyl]-pyridin-2-yl}-benzamide

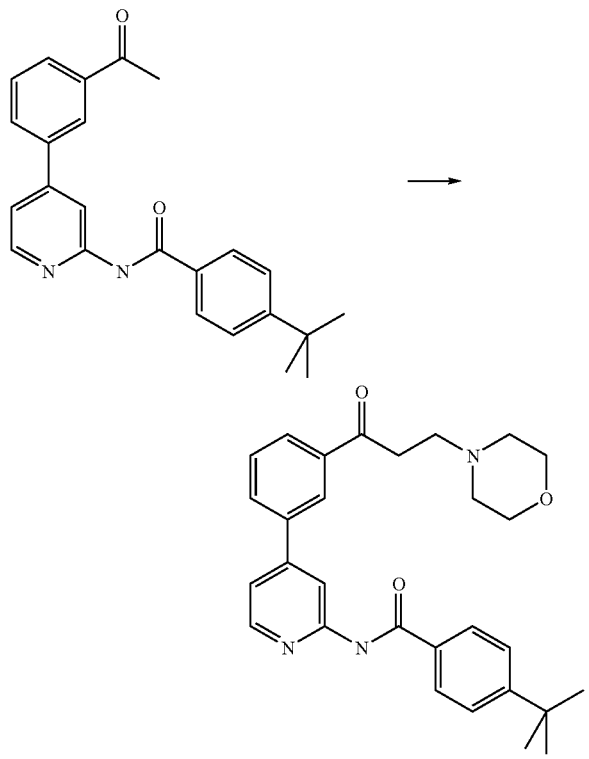

According to the same procedure for the preparation of 1-[3-(2-Amino-pyridin-4-yl)-phenyl]-3-morpholin-4-yl-propan-1-one, 4-tert-Butyl-N-{4-3-(3-morpholin-4-yl-propionyl)-phenyl]-pyridin-2-yl}-benzamide (12 mg, 30%) was obtained from N-[4-(3-Acetyl-phenyl)-pyridin-2-yl]-4-tert-butyl-benzamide (36 mg, 0.1 mmol). MS: m/z 472.3 [MH⁺].

EXAMPLE 13

Preparation of N-[4-(3-Acetyl-phenyl)-pyridin-2-yl]-acetamide

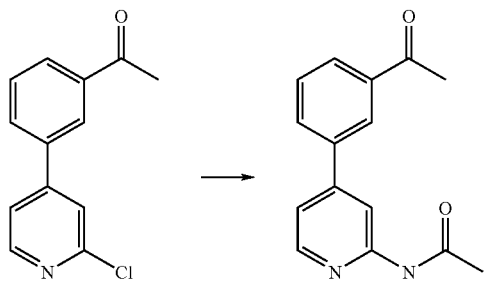 [SMILES: CC(=O)c1cccc(-c2ccnc(Cl)c2)c1 ; CC(=O)Nc1cc(-c2cccc(C(C)=O)c2)ccn1]

According the same procedure for the preparation of N-[4-(3-Acetyl-phenyl)-pyridin-2-yl]-benzamide, N-[4-(3-Acetyl-phenyl)-pyridin-2-yl]-acetamide (50 mg, 50%, slight impurity) was obtained from 1-[3-(2-Chloro-pyridin-4-yl)-phenyl]-ethanone (100 mg, 0.43 mmol) and acetamide (26 mg, 0.86 mmol). MS: m/z 255.1 [MH⁺].

EXAMPLE 14

Preparation of N-{4-[3-(3-Morpholin-4-yl-propionyl)-phenyl]-pyridin-2-yl}-acetamide

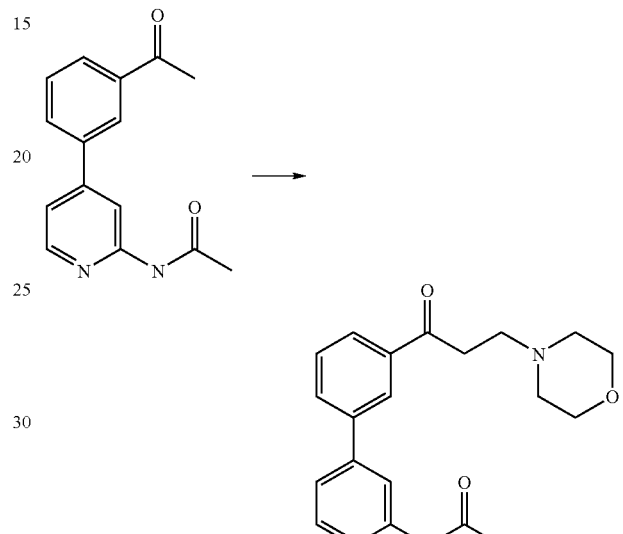

According to the same procedure for the preparation of 1-[3-(2-Amino-pyridin-4-yl)-phenyl]-3-morpholin-4-yl-propan-1-one, N-{4-[3-(3-Morpholin-4-yl-propionyl)-phenyl]-pyridin-2-yl}-acetamide (10 mg, 20%) was obtained from N-[4-(3-Acetyl-phenyl)-pyridin-2-yl]-acetamide (50 mg, 0.2 mmol). MS: m/z 354.3 [MH⁺].

EXAMPLE 15

In Vitro Assays

Measurement of IL-2 Production

Human T cell lines were plated in 96 well plates pre-coated with anti-CD3 monoclonal antibodies. Wells were either left untreated or treated with anti-CD28 for 2 days. The supernatant was collected and tested for IL-2 production in the presence or absence of a test compound using a human IL-2 ELISA assay.

T Cell Proliferation Assay

Human T cell lines were plated in 96 well plates pre-coated with anti-CD3 monoclonal antibodies. Wells were either left untreated or treated with anti-CD28 for 2 days. Cell proliferation was measured in the presence or absence of a test compound using a commercially available CELLTITER-GLO™ assay (Promega).

In Vitro Kinase Assays

Compounds were screened using the HITHUNTER™ enzyme fragment complementation method (Discoverx). Briefly, a recombinantly produced, N-terminally His-tagged ITK kinase domain (amino acids 352-617) was incubated with various concentrations of individual compounds. ATP and substrate were added, and the kinase reaction was allowed to proceed for 2-16 hours. Commercially available detection reagents were added and allowed to react for 2-4 hours. The reaction was evaluated by luminescence. Initial results were confirmed using full-length recombinant ITK protein.

Similarly, commercially available reagents such as HITHUNTER™ were used to evaluate the effect of compounds on the activity of additional kinases. The kinase domains of BTK, LCK and ERK were expressed as recombinant purified proteins were used for these studies.

The compounds in Table 1 were tested and shown to inhibit IL-2 production, to inhibit T cell proliferation, and to inhibit ITK with an $IC_{50}$ of less than 1 µM.

TABLE 1

| Compound | $IC_{50}$ (µM) |
|---|---|
| | 0.01807 |
| | 0.00954 |
| | 0.01355 |
| | 0.02851 |
| | 0.00533 |

TABLE 1-continued

| Compound | $IC_{50}$ (µM) |
|---|---|
| | 0.00426 |
| | 0.05043 |
| | 0.0114 |
| | 0.01327 |
| | 0.00686 |
| | 0.02855 |

TABLE 1-continued

| Compound | IC$_{50}$ (μM) |
|---|---|
| 1-(naphthalen-2-yl)-3-(3,4-dihydroisoquinolin-2(1H)-yl)propan-1-one | 0.01825 |
| 1-(naphthalen-2-yl)-3-(6,7-dimethoxy-3,4-dihydroisoquinolin-2(1H)-yl)propan-1-one | 0.00085 |
| 1-(6-chloronaphthalen-2-yl)-3-morpholinopropan-1-one | 0.07194 |
| 3-((furan-2-ylmethyl)(methyl)amino)-1-(naphthalen-2-yl)propan-1-one | 0.01964 |

The compounds in Tables 2-5 were tested in in vitro kinase assays:

TABLE 2

| Compound | IC$_{50}$ ITK (μM) | IC$_{50}$ BTK (μM) | IC$_{50}$ LCK (μM) |
|---|---|---|---|
| 1-(3,5-dimethoxyphenyl)-3-morpholinopropan-1-one | 0.005 | 0.42482 | 12.55299 |
| 6-(3-morpholinopropanoyl)-2H-benzo[b][1,4]oxazin-3(4H)-one | 0.040 | 0.27584 | 2.89341 |
| 1-(biphenyl-4-yl)-3-morpholinopropan-1-one | 0.04022 | 0.0369 | 8.03843 |
| 1-(4-fluorophenyl)-3-morpholinopropan-1-one | 0.013 | 1.41274 | 27.7419 |
| 1-(3,4-dichlorophenyl)-3-morpholinopropan-1-one | 0.013 | 0.10223 | 34.05941 |

TABLE 2-continued
| Compound | IC$_{50}$ ITK (μM) | IC$_{50}$ BTK (μM) | IC$_{50}$ LCK (μM) |
|---|---|---|---|
| 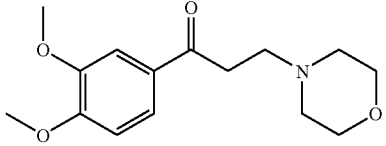 [SMILES: COc1ccc(C(=O)CCN2CCOCC2)cc1OC] | 0.014 | 1.83528 | 23.89837 |
| 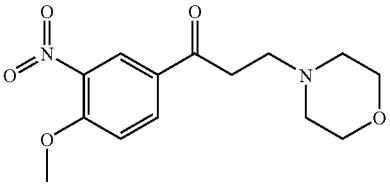 [SMILES: COc1ccc(C(=O)CCN2CCOCC2)cc1[N+](=O)[O-]] | 0.020 | | |
| 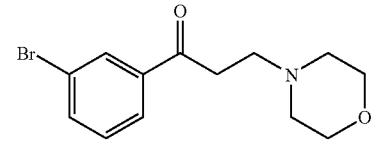 | 0.025 | 0.36501 | NO IC50 |
| 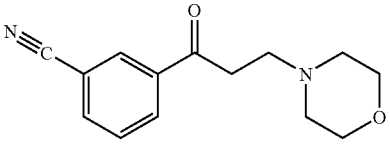 [SMILES: N#Cc1cccc(C(=O)CCN2CCOCC2)c1] | 0.029 | 0.64341 | 413.06105 |
| 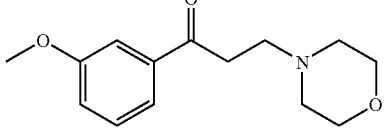 | 0.035 | 0.94241 | 16.4214 |
| 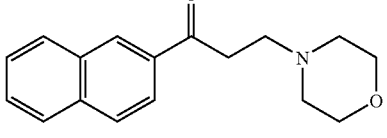 | 0.036 | 0.039 | 19.969 |
| 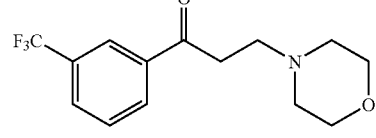 | 0.043 | 0.6561 | 27.11277 |
| 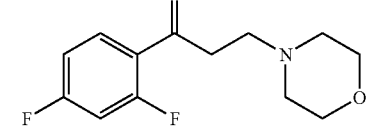 | 0.056 | 0.86517 | NO IC50 |
| 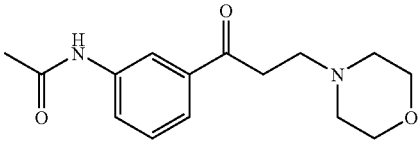 [SMILES: CC(=O)Nc1cccc(C(=O)CCN2CCOCC2)c1] | 0.065 | 1.24489 | 18.43928 |

TABLE 2-continued
| Compound | IC$_{50}$ ITK (μM) | IC$_{50}$ BTK (μM) | IC$_{50}$ LCK (μM) |
| --- | --- | --- | --- |
| 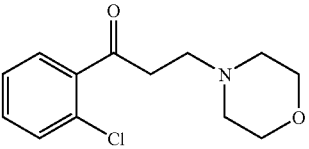 | 0.067 | 0.12463 | 28.09552 |
| 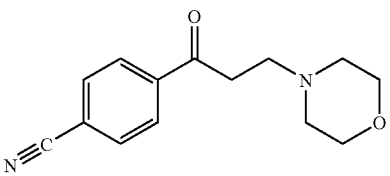 [SMILES: N#Cc1ccc(C(=O)CCN2CCOCC2)cc1] | 0.072 | 0.7368 | NO IC50 |
| 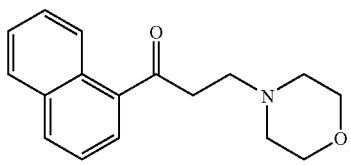 [SMILES: O=C(CCN1CCOCC1)c1cccc2ccccc12] | 0.065 | 0.39763 | 23.16665 |
| 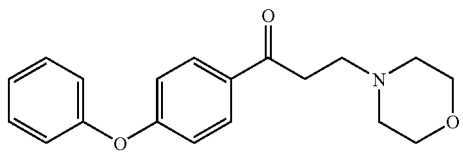 [SMILES: O=C(CCN1CCOCC1)c1ccc(Oc2ccccc2)cc1] | 0.091 | 0.09415 | 18.46087 |
| 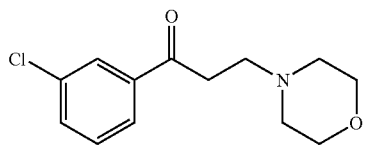 [SMILES: O=C(CCN1CCOCC1)c1cccc(Cl)c1] | 0.077 | 0.77538 | 47.61179 |
| 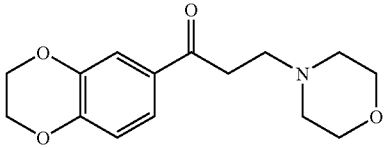 [SMILES: O=C(CCN1CCOCC1)c1ccc2c(c1)OCCO2] | 0.096 | 1.53948 | 20.8277 |
| 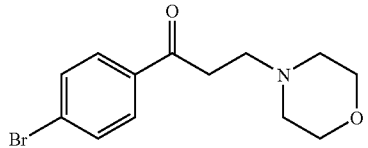 [SMILES: O=C(CCN1CCOCC1)c1ccc(Br)cc1] | 0.104 | 0.23242 | NO IC50 |
| 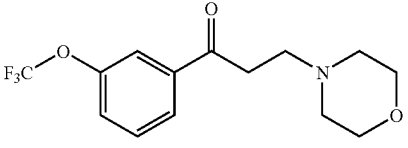 [SMILES: O=C(CCN1CCOCC1)c1cccc(OC(F)(F)F)c1] | 0.148 | 0.77352 | 28.01341 |
| 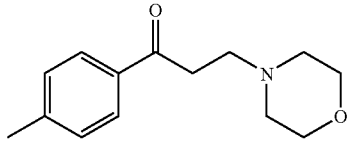 [SMILES: Cc1ccc(C(=O)CCN2CCOCC2)cc1] | 0.180 | 1.52018 | 163.63704 |

TABLE 2-continued

| Compound | IC$_{50}$ ITK (μM) | IC$_{50}$ BTK (μM) | IC$_{50}$ LCK (μM) |
| --- | --- | --- | --- |
| 3-(dimethylamino)phenyl morpholinopropanone | 0.186 | 3.67569 | 20.64831 |
| 4-(trifluoromethyl)phenyl morpholinopropanone | 0.199 | 0.4735 | NO IC50 |
| 3-phenoxyphenyl morpholinopropanone | 0.207 | 0.09415 | 18.46087 |
| 3,4-difluorophenyl morpholinopropanone | 0.208 | 2.89272 | 33.1157 |
| 2,6-dichlorophenyl morpholinopropanone | 0.207 | 0.08071 | NO IC50 |
| 4-(trifluoromethoxy)phenyl morpholinopropanone | 0.219 | 1.30729 | NO IC50 |
| 3,4-dimethylphenyl morpholinopropanone | 0.223 | 1.47599 | 21.15799 |
| 2-chlorophenyl morpholinopropanone | 0.241 | 0.81405 | NO IC50 |
| 4-chlorophenyl morpholinopropanone | 0.290 | 0.68214 | 25.86619 |

TABLE 2-continued
| Compound | IC$_{50}$ ITK (μM) | IC$_{50}$ BTK (μM) | IC$_{50}$ LCK (μM) |
|---|---|---|---|
| 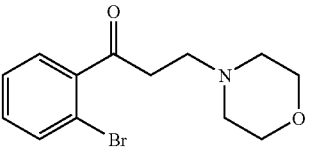 [SMILES: O=C(CCN1CCOCC1)c1ccccc1Br] | 0.305 | 0.74064 | NO IC50 |
| 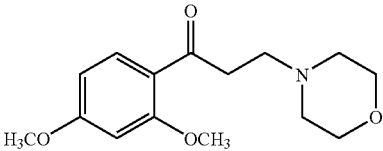 [SMILES: COc1ccc(C(=O)CCN2CCOCC2)c(OC)c1] | 0.345 | 3.1355 | 21.10834 |
| 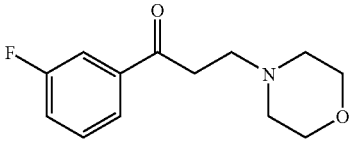 [SMILES: O=C(CCN1CCOCC1)c1cccc(F)c1] | 0.381 | 3.03351 | 32.57859 |
| 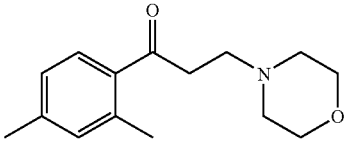 [SMILES: Cc1ccc(C(=O)CCN2CCOCC2)c(C)c1] | 0.385 | 1.47531 | 25.34326 |
| 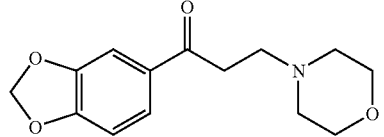 [SMILES: O=C(CCN1CCOCC1)c1ccc2c(c1)OCO2] | 0.385 | 3.92321 | 23.25 |
| 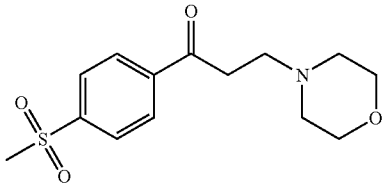 [SMILES: CS(=O)(=O)c1ccc(C(=O)CCN2CCOCC2)cc1] | 0.385 | 0.75252 | 23.94596 |
| 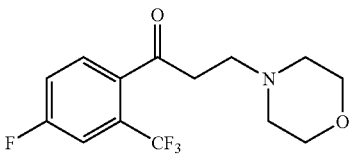 [SMILES: O=C(CCN1CCOCC1)c1ccc(F)cc1C(F)(F)F] | 0.468 | 1.21899 | NO IC50 |
| 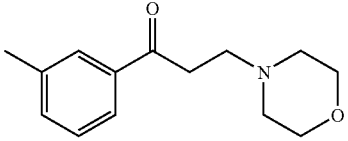 [SMILES: Cc1cccc(C(=O)CCN2CCOCC2)c1] | 0.560 | 3.06627 | 24.36134 |
| 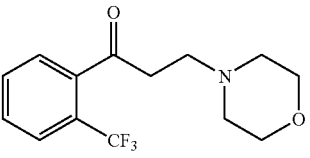 [SMILES: O=C(CCN1CCOCC1)c1ccccc1C(F)(F)F] | 0.569 | 1.01979 | NO IC50 |

TABLE 2-continued
| Compound | IC$_{50}$ ITK (μM) | IC$_{50}$ BTK (μM) | IC$_{50}$ LCK (μM) |
|---|---|---|---|
| 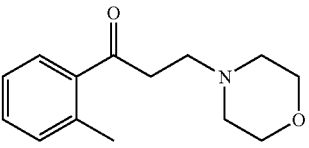 [SMILES: Cc1ccccc1C(=O)CCN1CCOCC1] | 0.611 | 2.31114 | NO IC50 |
| 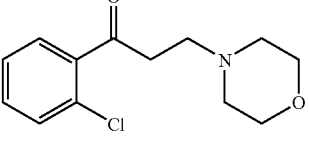 | 0.797 | 3.62429 | NO IC50 |
| 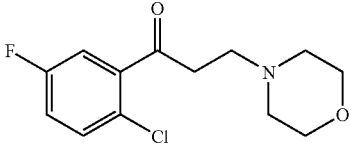 [SMILES: O=C(CCN1CCOCC1)c1cc(F)ccc1Cl] | 0.935 | 0.99267 | 29.52378 |
| 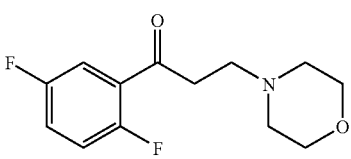 [SMILES: O=C(CCN1CCOCC1)c1cc(F)ccc1F] | 0.874 | 2.57662 | NO IC50 |
| 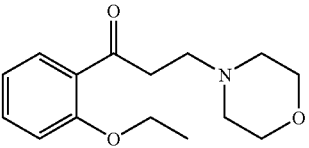 [SMILES: CCOc1ccccc1C(=O)CCN1CCOCC1] | 1.279 | 0.55617 | 704.77096 |
| 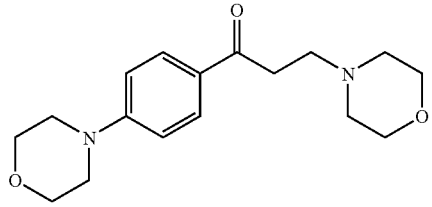 [SMILES: O=C(CCN1CCOCC1)c1ccc(N2CCOCC2)cc1] | 1.406 | 4.1378 | 27.08267 |
TABLE 3
| Compound | IC$_{50}$ ITK (μM) | IC$_{50}$ BTK (μM) | naphthyl analog | IC$_{50}$ ITK (μM) | IC$_{50}$ BTK (μM) |
|---|---|---|---|---|---|
| 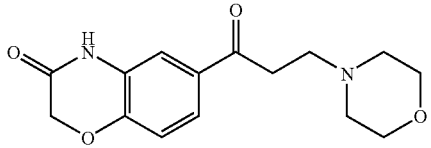 [SMILES: O=C1COc2ccc(C(=O)CCN3CCOCC3)cc2N1] | 0.0059 | 0.7810 | 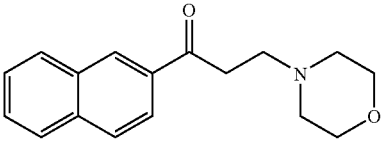 [SMILES: O=C(CCN1CCOCC1)c1ccc2ccccc2c1] | 0.020 | 0.03947 |
| 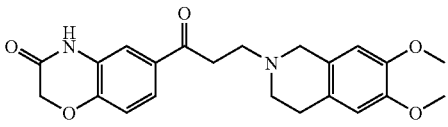 [SMILES: COc1cc2c(cc1OC)CN(CCC(=O)c1ccc3c(c1)NC(=O)CO3)CC2] | 0.030 | 0.276 | 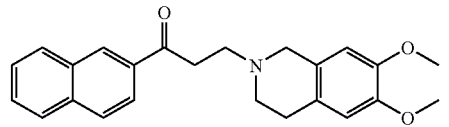 [SMILES: COc1cc2c(cc1OC)CN(CCC(=O)c1ccc3ccccc3c1)CC2] | 0.007 | 0.01276 |

TABLE 3-continued

| Compound | IC$_{50}$ ITK (μM) | IC$_{50}$ BTK (μM) | naphthyl analog | IC$_{50}$ ITK (μM) | IC$_{50}$ BTK (μM) |
| --- | --- | --- | --- | --- | --- |
| | 0.072 | 1.894 | | 0.007 | 0.00215 |
| | 0.010 | 0.300 | | 0.006 | 0.00338 |
| | 0.018 | 0.481 | | 0.008 | 0.00152 |
| | 0.013 | 0.150 | | 0.009 | 0.00654 |
| | 0.023 | 0.544 | | 0.009 | 0.00072 |

TABLE 4

| Compound | IC$_{50}$ ITK (μM) | IC$_{50}$ BTK (μM) |
| --- | --- | --- |
| | 0.05666 | |
| | 0.03034 | |
| | 0.09281 | |

TABLE 4-continued
| Compound | IC$_{50}$ ITK (μM) | IC$_{50}$ BTK (μM) |
|---|---|---|
| 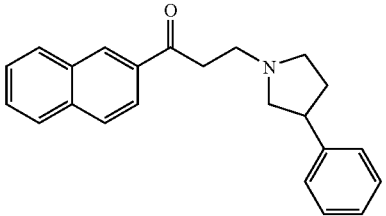 [SMILES: O=C(CCN1CCC(c2ccccc2)C1)c1ccc2ccccc2c1] | 0.02285 | |
| 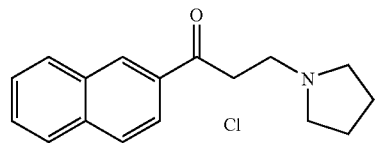 [SMILES: O=C(CCN1CCCC1)c1ccc2ccccc2c1 ; Cl] | 0.07489 | |
|  | 0.020 | 0.039 |
| 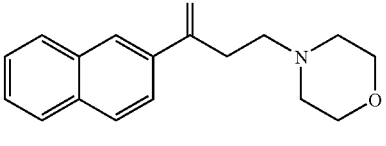 | 0.048 | 5.001 |
| 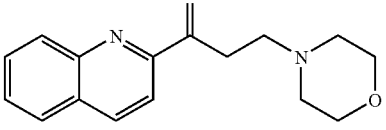 | 1.684 | no IC$_{50}$ |
| 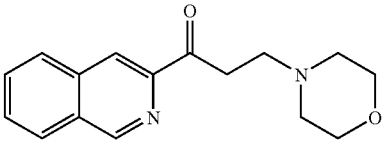 [SMILES: O=C(CCN1CCOCC1)c1cc2ccccc2cn1] | 0.189 | 0.100 |
| 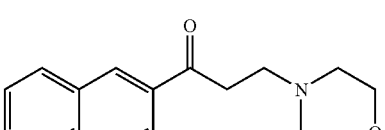 | 0.176 | 8.174 |
| 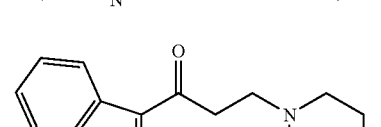 | 0.049 | 0.296 |
| 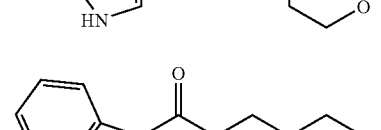 | 0.134 | 0.611 |
TABLE 4-continued
| Compound | IC$_{50}$ ITK (μM) | IC$_{50}$ BTK (μM) |
|---|---|---|
| 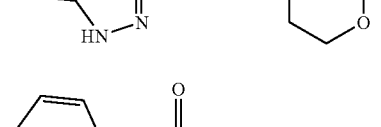 | 0.075 | 2.038 |
| 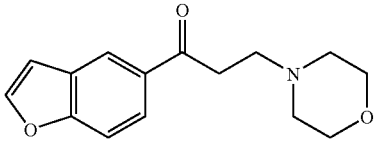 [SMILES: O=C(CCN1CCOCC1)c1ccc2occc2c1] | 0.060 | 0.334 |
| 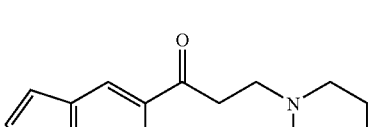 | 56.392 | no IC$_{50}$ |
| 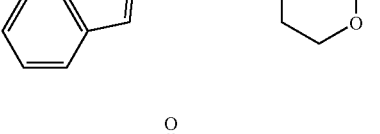 | 0.010 | 0.017 |
| 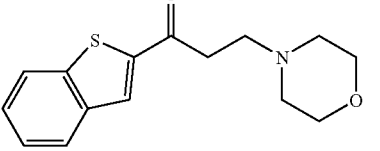 | 0.030 | 0.006 |
| 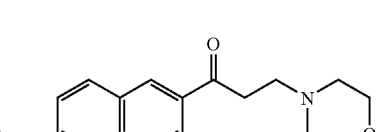 | 3.339 | 2.364 |
| 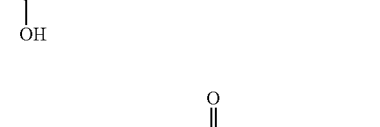 | 0.005 | 0.001 |
| 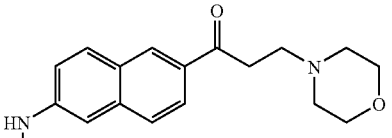 | 0.042 | 0.002 |

TABLE 5
| Compound | IC$_{50}$ ITK (μM) | IC$_{50}$ BTK (μM) |
|---|---|---|
| 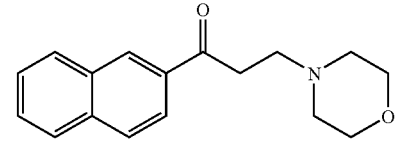 [SMILES: O=C(CCN1CCOCC1)c1ccc2ccccc2c1] | 0.0205 | 0.0395 |
| 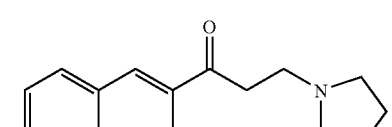 | 0.1369 | 8.21849 |
| 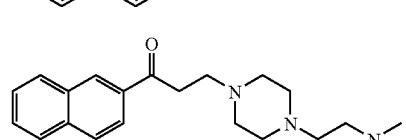 | 0.0080 | 0.06706 |
| 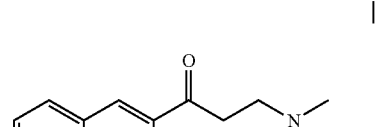 | 0.0169 | |
| 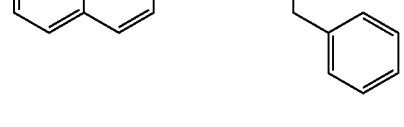 | 0.0602 | 0.12799 |
| 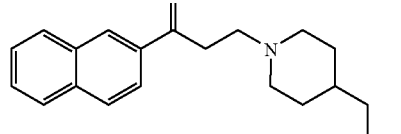 | 0.0148 | |
| 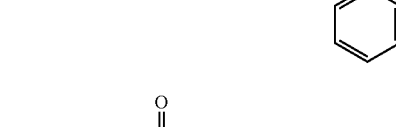 | 0.5375 | |
| 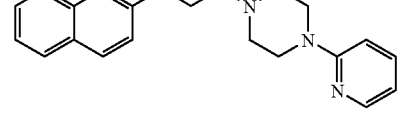 | 0.8516 | |
| 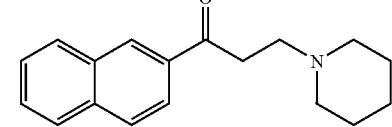 | 0.0309 | |
TABLE 5-continued
| Compound | IC$_{50}$ ITK (μM) | IC$_{50}$ BTK (μM) |
|---|---|---|
| 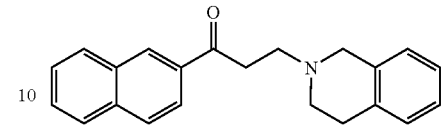 | 0.0212 | |
| 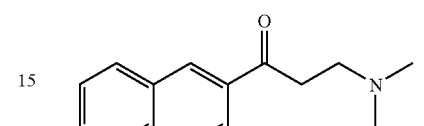 | 0.1609 | |
| 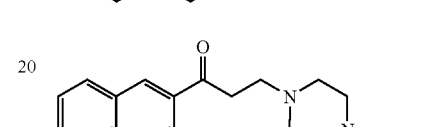 | 0.0242 | |
| 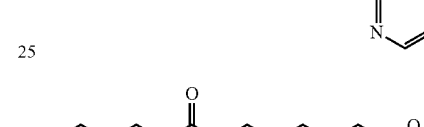 | 0.0072 | 0.11532 |
| 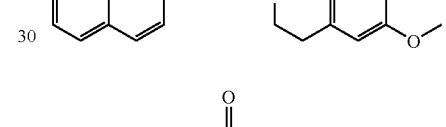 | 0.3096 | |
| 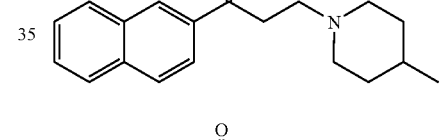 | 0.0069 | 0.0492 |
| 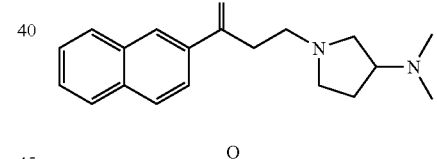 | 0.0187 | |
| 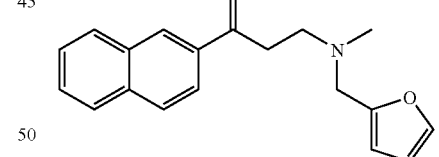 | 0.0095 | |
| 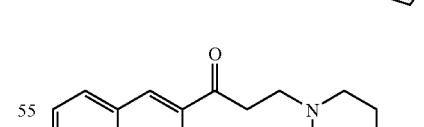 | 0.0162 | |

TABLE 5-continued
| Compound | IC$_{50}$ ITK (μM) | IC$_{50}$ BTK (μM) |
|---|---|---|
| 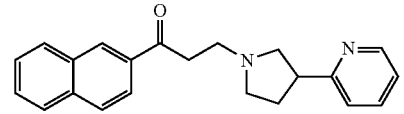 [SMILES: O=C(CCN1CCC(c2ccccn2)C1)c1ccc2ccccc2c1] | 0.0359 | |
| 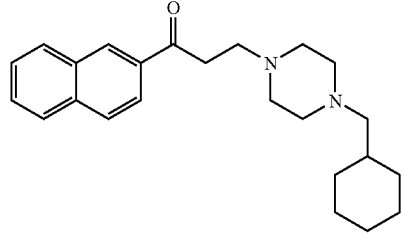 [SMILES: O=C(CCN1CCN(CC2CCCCC2)CC1)c1ccc2ccccc2c1] | 0.0147 | |
| 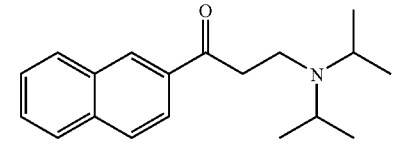 [SMILES: CC(C)N(CCC(=O)c1ccc2ccccc2c1)C(C)C] | 0.0092 | |
| 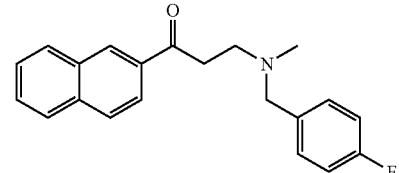 | 0.0062 | 0.16054 |
| 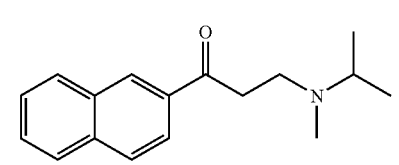 [SMILES: CC(C)N(C)CCC(=O)c1ccc2ccccc2c1] | 0.0163 | |
| 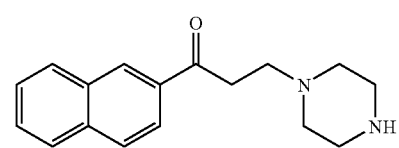 [SMILES: O=C(CCN1CCNCC1)c1ccc2ccccc2c1] | 0.117 | 0.410 |
| 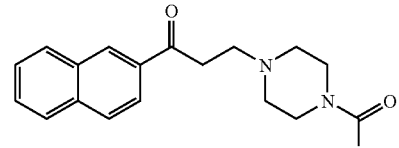 | 0.023 | 0.153 |
| 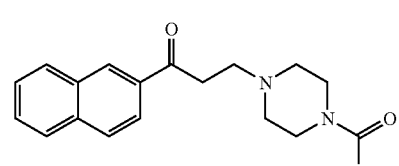 | 0.056 | 0.452 |
| 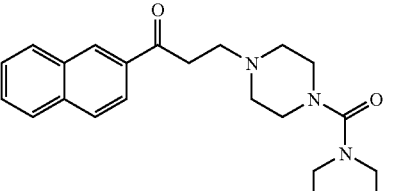 | 0.060 | 0.242 |
| 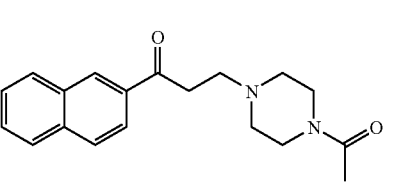 [SMILES: CC(=O)N1CCN(CCC(=O)c2ccc3ccccc3c2)CC1] | 0.066 | 0.089 |
| 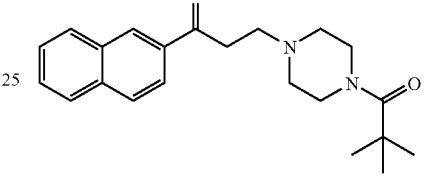 | 0.064 | 0.360 |
| 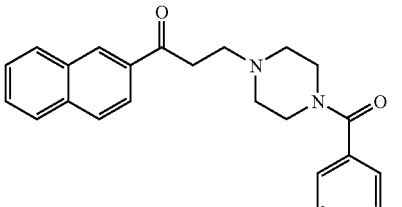 | 0.054 | 0.018 |
| 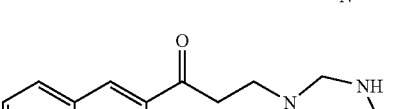 | 0.087 | 0.051 |
| 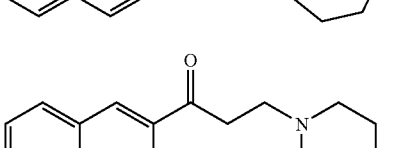 | 0.031 | 0.071 |
| 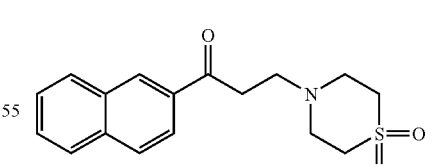 | 0.066 | 0.117 |
| 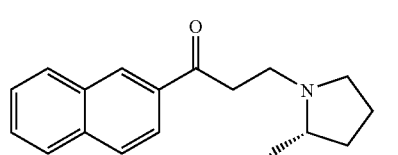 | 0.049 | 0.123 |

TABLE 5-continued

| Compound | IC$_{50}$ ITK (μM) | IC$_{50}$ BTK (μM) |
|---|---|---|
| 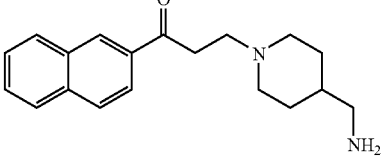 | 0.086 | 0.084 |
| 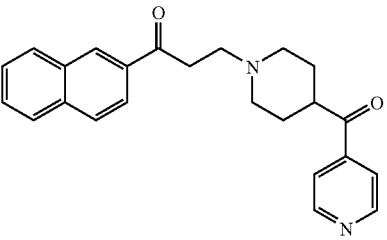 [SMILES: O=C(CCN1CCC(C(=O)c2ccncc2)CC1)c1ccc2ccccc2c1] | 0.284 | 0.486 |
| 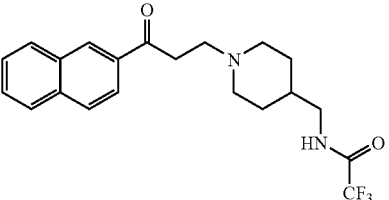 | 0.217 | 0.266 |
| 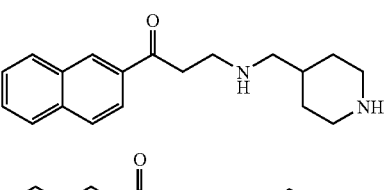 | 0.163 | 0.100 |
| 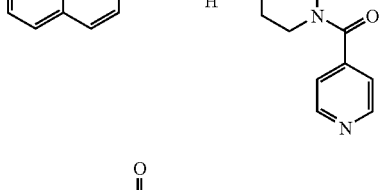 | 0.036 | 0.004 |
| 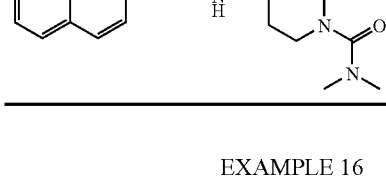 | 0.737 | 0.373 |

EXAMPLE 16

In Vivo Studies

Several representative compounds were evaluated for efficacy in mouse in vivo tumor models. NOD/SCID mice were implanted intraperitoneally with T cell leukemia/lymphoma cells. One group was treated with vehicle alone (mock treatment) while the other groups were treated with several small molecule inhibitors via intraperitoneal route. Tumor growth was evaluated by peritoneal lavage and FACS analysis. Table 6 summarizes percent inhibition of tumor growth relative to a mock group treated with vehicle alone. Doses of compounds evaluated in this study were below the maximal tolerated dose, and showed minimal toxicity.

The compounds in Table 6 were tested and inhibited tumor growth by at least 50% at the concentrations shown.

TABLE 6

| Compound | mg/kg | % inhibition tumor growth |
|---|---|---|
| 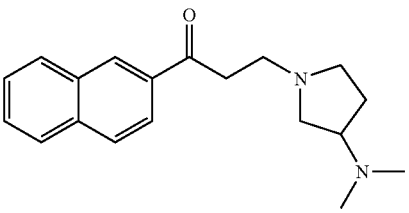 [SMILES: CN(C)C1CCN(CCC(=O)c2ccc3ccccc3c2)C1] | 100 | 70-90 |
| 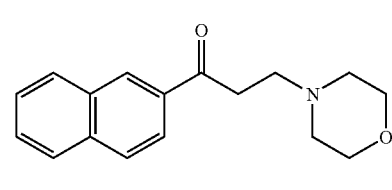 [SMILES: O=C(CCN1CCOCC1)c1ccc2ccccc2c1] | 100 | 85-98 |
| 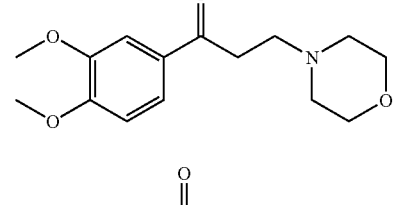 | 80 | 92-99 |
| 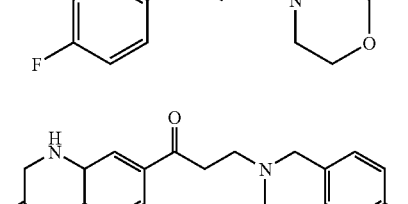 | 80 | 50-80 |
| 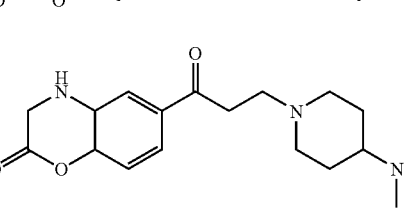 | 80 | 90-99 |
| 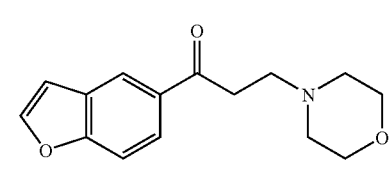 | 80 | 99 |
| 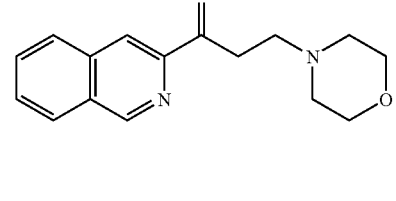 | 80 | 67-81 |
|  | 80 | 92-99 |

TABLE 6-continued

| Compound | mg/kg | % inhibition tumor growth |
|---|---|---|
| [structure: 3-oxo-3,4-dihydro-2H-benzo[b][1,4]oxazin-6-yl propanone with 3-(dimethylamino)pyrrolidine] | 100 | 99 |
| [structure: 3-oxo-3,4-dihydro-2H-benzo[b][1,4]oxazin-6-yl propanone with 6,7-dimethoxy-1,2,3,4-tetrahydroisoquinoline] | 80 | 97-99 |
| [structure: 6-carboxamido-naphthalen-2-yl propanone with morpholine] | 30 | 99 |
| [structure: 4-(pyridin-3-yl)phenyl propanone with morpholine] | 100 | 99 |
| [structure: 3,4-dimethoxyphenyl propanone with 4-(methylamino)piperidine] | 80 | 81-95 |
| [structure: 3-oxo-3,4-dihydro-2H-benzo[b][1,4]oxazin-6-yl propanone with morpholine] | 20 | 40 |
| vehicle | — | 0 |

EXAMPLE 17

Compound Activity Mechanism

The compound class interacts selectively with kinase domains of such kinase families as Tec and EGFR, as well as a few additional kinases. There is evidence indicating that this class of compounds reacts irreversibly at the ATP binding site of the kinase binding domain, through a mechanism that involves the exposure of a reactive aminoethyl C=Y warhead through the in situ elimination of a leaving group. The compounds contain an abstractable proton adjacent to the C=Y group, which upon exposure to an appropriate catalytic environment in the active site of a kinase of interest will promote elimination of the beta-amino functionality. This elimination thus generates a reactive electrophilic species (commonly termed a Michael acceptor moiety) which, due to the existence of a proximal cysteine residue in the kinase active site, rapidly forms a covalent adduct between this cysteine residue and the in situ generated electrophylic species. The combination of a kinase with the catalytic environment in close proximity to a nucleophilic cysteine, is a vital and unique requirement that describes this mechanism of action. The data below support that in situ elimination promotes the inhibitory activity of compounds in depicted in this invention. When a compound is modified in a manner that prevents elimination, the compound fails to exhibit inhibitory activity.

TABLE 7

| compound | $IC_{50}$ ITK |
|---|---|
| [structure: naphthalen-2-yl propanone with morpholine] | 0.0446 |
| [structure: naphthalen-2-yl propanol with morpholine (OH instead of ketone)] | no $IC_{50}$ |
| [structure: naphthalen-2-yl 2,2-dimethyl propanone with piperidine] | no $IC_{50}$ |

EXAMPLE 18

Covalent Binding to Select Kinases

As a result of elimination in proximity of a relevant cysteine, a covalent adduct is formed between the compound and the kinase domain. The irreversible binding that ensues can be demonstrated by several methods, including surface plasmon resonance (SPR) and co-precipitation of the compound with the kinase.

BIACORE® is a SPR-based protein interaction approach, whereby the kinase is immobilized on the sensor chip, and a small molecule solution allowed to interact with the kinase. Detection of small molecule/kinase interaction occurs in real time, and is detected as a difference in SPR response. FIG. 1 shows a BIACORE® experiment in which the ITK kinase domain was immobilized on a biosensor, and evaluated for its ability to bind and dissociate form a small molecule. The data indicates that compounds depicted in this application bind to the ITK kinase domain irreversibly.

In the co-precipitation assay, 1-10 mM labeled compound is incubated with cell lysates from either kinase expressing or kinase lacking cells. The label is then used to precipitate the compound and any bound proteins. The mixture is separated by SDS-PAGE and proteins are identified by western blotting and/or Mass spectrophotometry.

EXAMPLE 19

Contribution of Cysteine 442 to Adduct Formation

In order to confirm the mechanism by which compounds depicted herein interact with the kinase domain of Tec and EGFR kinases, we created a point mutant of the ITK kinase domain, whereby the key amino acid, namely C442 was mutated to alanine. The protein was expressed in a commercial baculovirus expression system using the manufacturer's general protocol (Invitrogen, pBlueBac). Protein was expressed and purified using standard techniques. Both wild type (WT) ITK kinase domain and C442A kinase domain exhibited kinase activity. While the activity of WT-ITK was inhibited by compounds depicted in this application, the same compounds had no activity towards the C442A mutant kinase domain.

TABLE 8

| compound | IC$_{50}$ (μM) | |
| --- | --- | --- |
| | wild-type ITK | C442A-ITK |
| control (BMS-488516) | 0.0392 | 0.0532 |
| 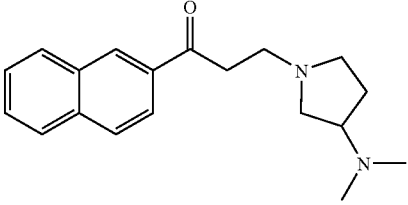 [SMILES: CN(C)C1CCN(CCC(=O)c2ccc3ccccc3c2)C1] | 0.011 | >10 |
| 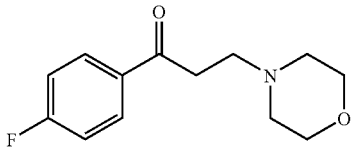 [SMILES: O=C(CCN1CCOCC1)c1ccc(F)cc1] | 0.0496 | >10 |
| 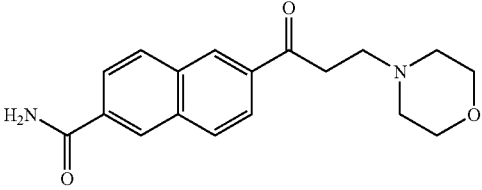 [SMILES: NC(=O)c1ccc2cc(C(=O)CCN3CCOCC3)ccc2c1] | 0.0111 | >10 |

---

The invention claimed is:

1. A protein kinase inhibitor selected from the group consisting of:

(a) compounds of structural formula II

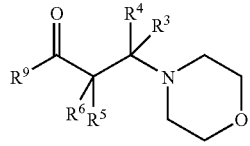

(II)

wherein:

$R^3$, $R^4$, $R^5$, and $R^6$ are independently hydrogen or optionally substituted $C_1$-$C_6$ alkyl;

$R^9$ is selected from,

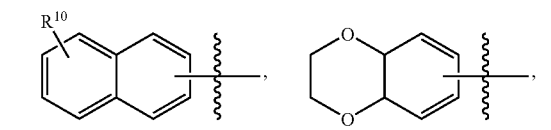

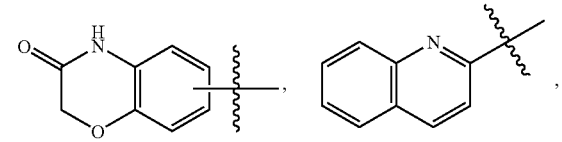

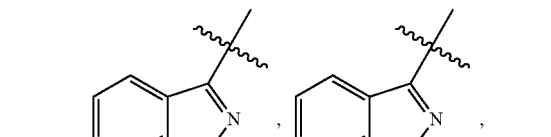

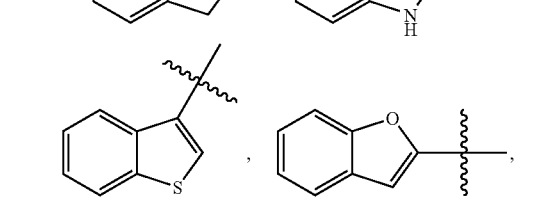

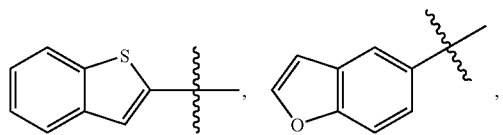

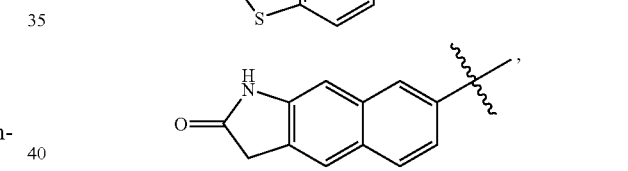

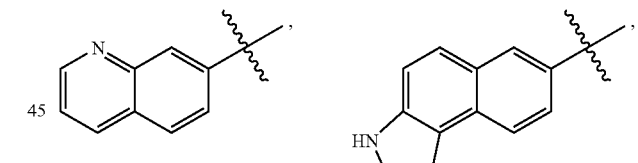

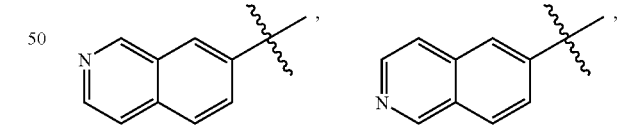

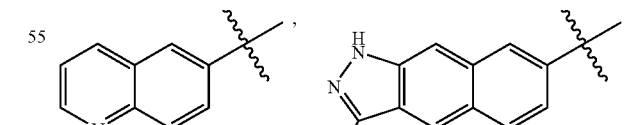

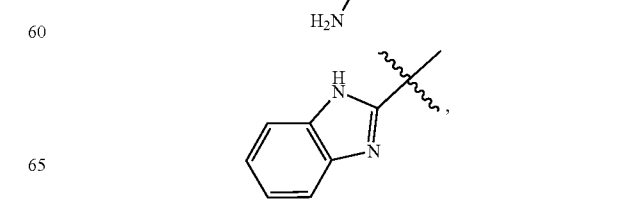

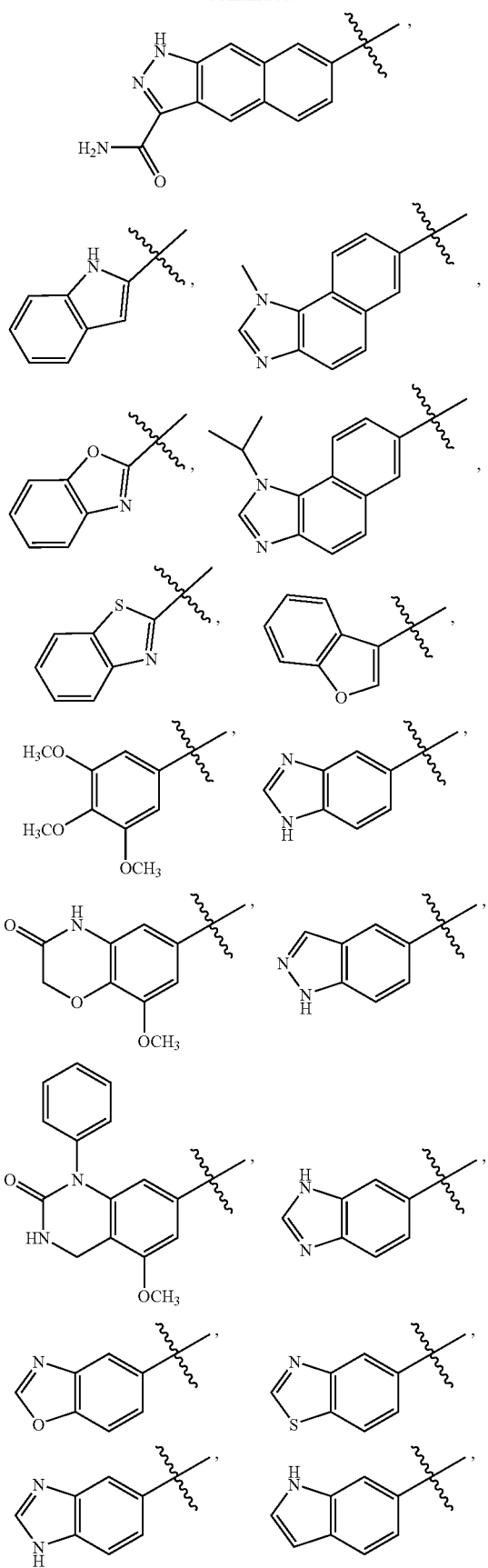
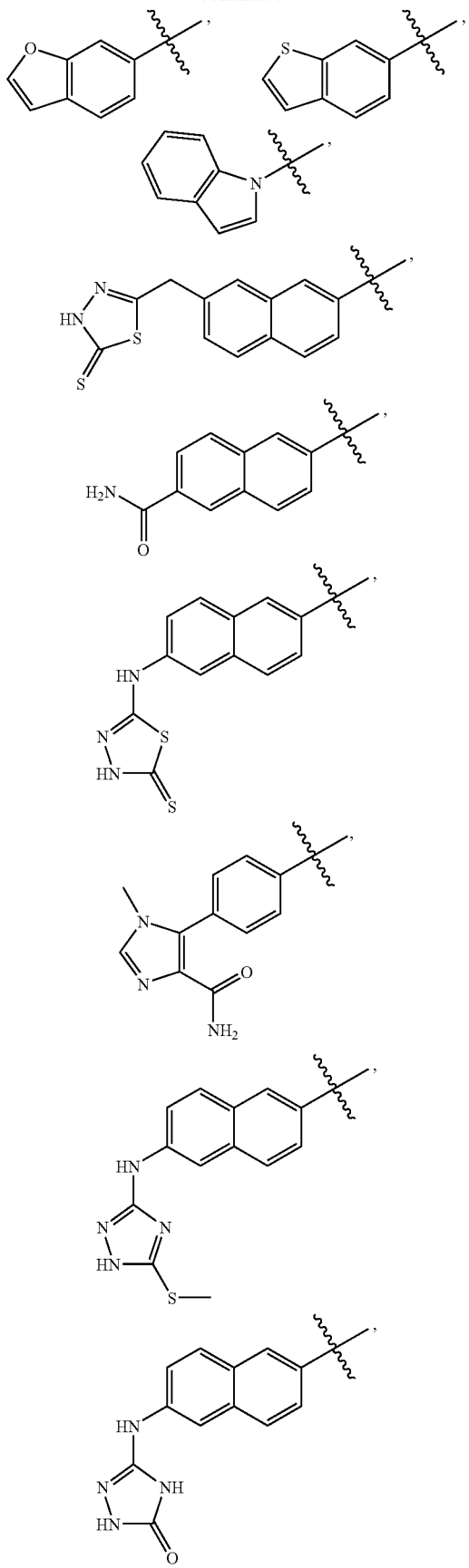

-continued

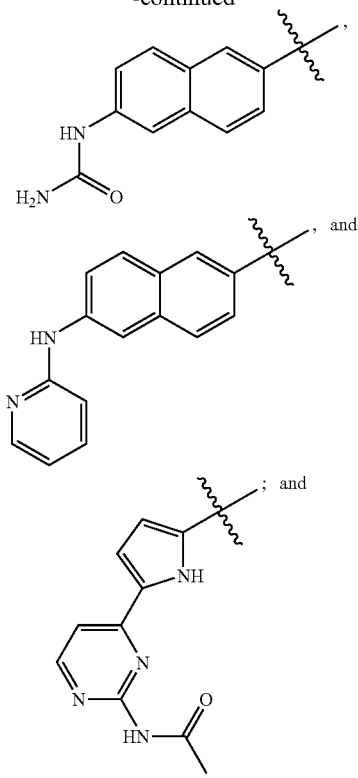

$R^{10}$ is hydrogen, —OH, —COOH, —CONH$_2$, or —NCO;

(b) compounds of structural formula III:

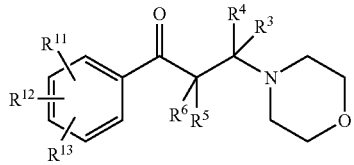

(III)

wherein:

$R^3$, $R^4$, $R^5$, and $R^6$ are independently hydrogen or optionally substituted $C_1$-$C_6$ alkyl;

$R^{11}$ and $R^{12}$ are independently selected from hydrogen, —OCH$_3$, halogen, —NO$_2$, —CN, —CF$_3$, —NCOR' (wherein R' is hydrogen or $C_1$-$C_4$ alkyl), phenyloxy, —OCF$_3$, —NR'R" (wherein R' and R" are independently hydrogen or $C_1$-$C_4$ alkyl), $C_1$-$C_4$ alkyl, $C_1$-$C_4$ alkoxy, and —SO$_2$R' (wherein R' is hydrogen or $C_1$-$C_4$ alkyl); and $R^{13}$ is hydrogen, $C_1$-$C_4$ alkyl,

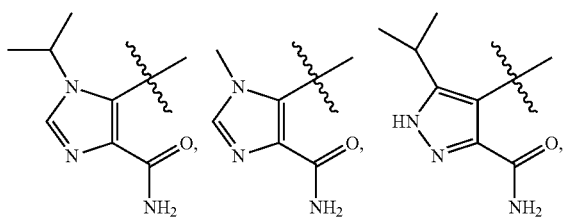

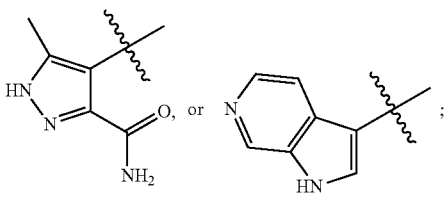

(c) compounds of structural formula IV:

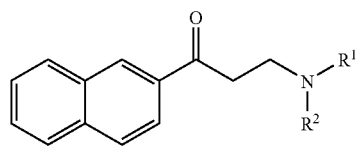

(IV)

wherein $R^1$ and $R^2$ (a) are independently hydrogen, optionally substituted $C_1$-$C_6$ alkyl, piperidine, or furanyl; or (b) are taken together with the nitrogen atom to which they are attached to form (i) a 5- to 7-membered optionally substituted aryl, (ii) a 5- to 7-membered optionally substituted heteroaryl, or (iii) a 5- to 7-membered optionally substituted heterocycle which may be unfused or fused to an optionally substituted aryl;

(d) compounds of structural formula VI:

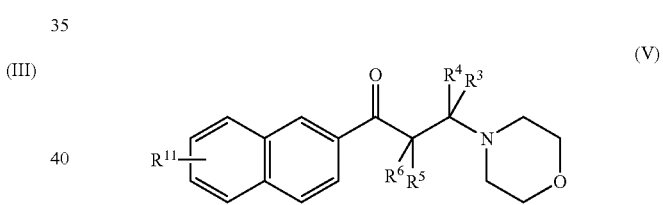

(V)

wherein:

$R^3$, $R^4$, $R^5$, and $R^6$ are independently hydrogen or optionally substituted $C_1$-$C_6$ alkyl; and $R^{10}$ is hydrogen, —OH, —COOH, —CONH$_2$, or —NCO;

(e) compounds of structural formula VI:

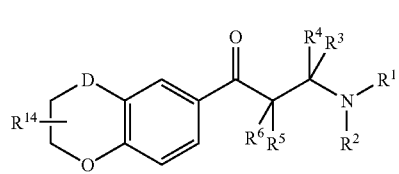

(VI)

wherein:

$R^1$, $R^2$, $R^3$, $R^4$, $R^5$, and $R^6$ are as defined above;

$R^{14}$ is hydrogen or =O; and

D is CH or NH;

(f) compounds of structural formula VII:

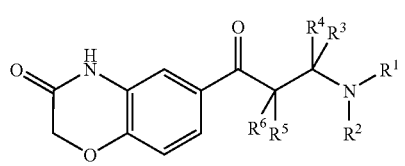

(VII)

wherein:

R³, R⁴, R⁵, and R⁶ are independently hydrogen or optionally substituted $C_1$-$C_6$ alkyl; and R¹ and R² are independently hydrogen, $C_1$-$C_4$ alkyl,

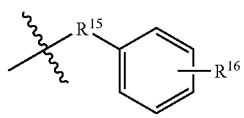

(wherein $R^{15}$ is halogen or $C_1$-$C_4$ alkyl and $R^{16}$ is $C_1$-$C_4$ alkyl), or R¹ and R² together with the nitrogen to which they are attached form an aryl group selected from

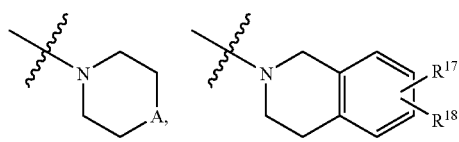

(wherein $R^{17}$ and $R^{18}$ are independently hydrogen or —OCH₃,)

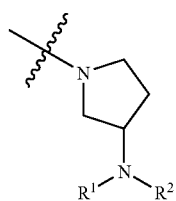

(wherein R¹ and R² are independently hydrogen or $C_1$-$C_4$ alkyl)

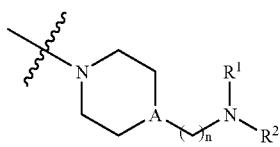

(wherein n=1-4), and phenyl-$C_1$-$C_4$ alkyl, optionally substituted with halogen;

(g) compounds of structural formula VIII:

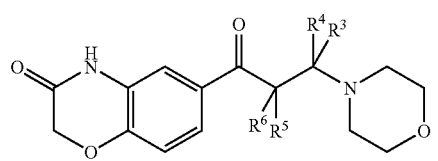

(VIII)

or a pharmaceutically acceptable salt thereof, wherein R³, R⁴, R⁵, and R⁶ are independently hydrogen or optionally substituted $C_1$-$C_6$ alkyl;

(h) compounds of structural formula IX:

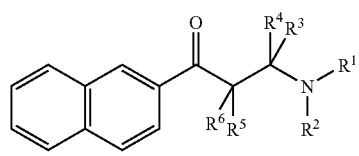

(IX)

wherein:

R³, R⁴, R⁵, and R⁶ are independently hydrogen or optionally substituted $C_1$-$C_6$ alkyl; and either
R¹ is hydrogen and R² is

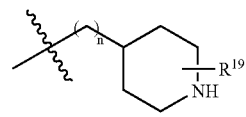

(wherein $R^{19}$ is selected from hydrogen and

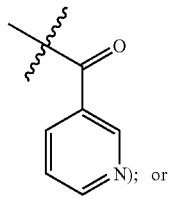

); or

R¹ and R² together with the nitrogen to which they are attached are

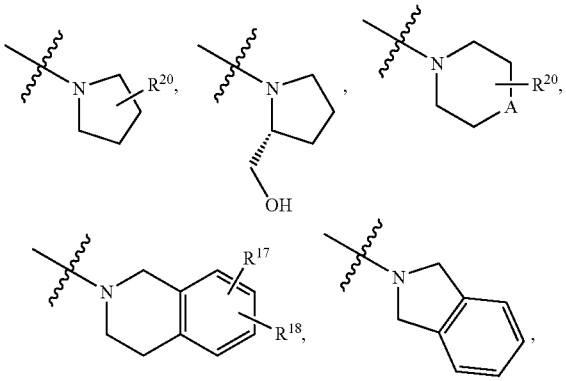

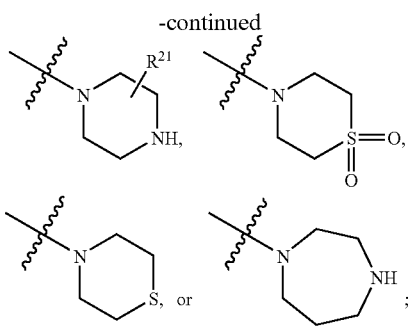

A is N or O;
R²⁰ is phenyl-$C_1$-$C_4$ alkyl optionally substituted with one or more halogens, hydrogen, $C_1$-$C_4$ alkyl, amino-$C_1$-$C_4$ alkyl,

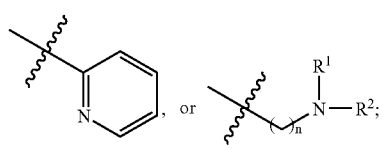

$R^{17}$ and $R^{18}$ are independently hydrogen or —OCH₃;
$R^{21}$ is —CONR'R", —COR',

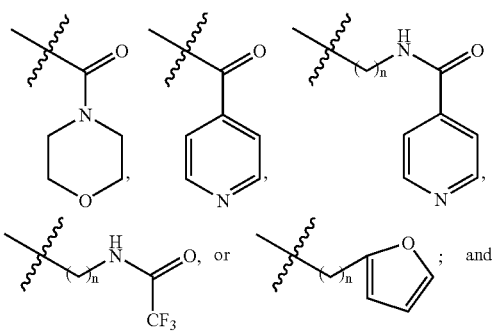

R' and R" are independently selected from hydrogen and $C_1$-$C_4$ alkyl; and
(i) compounds of structural formula XI:

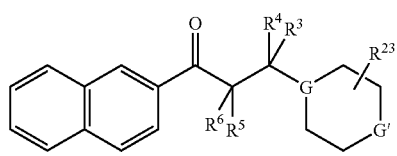

wherein:
$R^3$, $R^4$, $R^5$, and $R^6$ are independently hydrogen or optionally substituted $C_1$-$C_6$ alkyl;
G is N, CH, or S;
G' is NH, CH, or S;
$R^{23}$ is hydrogen, —NR'R" $C_1$-$C_4$ linear alkyl, $C_1$-$C_4$ alkyl, phenyl-$C_1$-$C_4$ alkyl, —CONH₂, or —CO R'R"; and
R' and R" are independently selected from hydrogen and $C_1$-$C_4$ alkyl, wherein the protein kinase inhibitor (1) inhibits interleukin-2 inducible tyrosine kinase (ITK) with an IC₅₀ of 0.00085 μM-1 μM in an in vitro kinase assay; (2) inhibits Bruton's tyrosine kinase (BTK) with an IC₅₀ of 0.00072 μM-1 μM in an in vitro kinase assay; or (3) inhibits interleukin-2 inducible tyrosine kinase (ITK) with an IC₅₀ of 0.00085 μM-1 μM and inhibits Bruton's tyrosine kinase (BTK) with an IC₅₀ of 0.00072 μM-1 μM in an in vitro kinase assay, with the proviso the protein kinase inhibitor is not

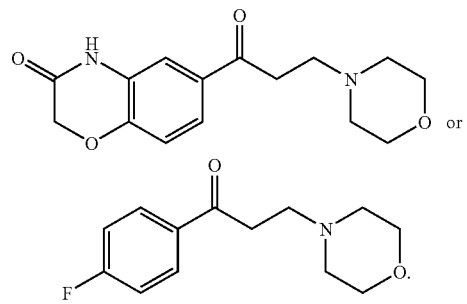

2. The protein kinase inhibitor of claim 1 which is a compound of structural formula II.
3. The protein kinase inhibitor of claim 1 which is a compound of structural formula III.
4. The protein kinase inhibitor of claim 1 which is a compound of structural formula IV.
5. The protein kinase inhibitor of claim 1 which is a compound of structural formula V.
6. The protein kinase inhibitor of claim 1 which is a compound of structural formula VI.
7. The protein kinase inhibitor of claim 1 which is a compound of structural formula VII.
8. The protein kinase inhibitor of claim 1 which is a compound of structural formula VIII.
9. The protein kinase inhibitor of claim 1 which is a compound of structural formula IX.
10. The protein kinase inhibitor of claim 1 which is a compound of structural formula XI.
11. A composition comprising:
(a) a pharmaceutically acceptable vehicle; and
(b) a protein kinase inhibitor of claim 1.
12. The composition of claim 11, wherein the protein kinase inhibitor is a compound of structural formula II.
13. The composition of claim 11, wherein the protein kinase inhibitor is a compound of structural formula III.
14. The composition of claim 11, wherein the protein kinase inhibitor is a compound of structural formula IV.
15. The composition of claim 11, wherein the protein kinase inhibitor is a compound of structural formula V.
16. The composition of claim 11, wherein the protein kinase inhibitor is a compound of structural formula VI.
17. The composition of claim 11, wherein the protein kinase inhibitor is a compound of structural formula VII.
18. The composition of claim 11, wherein the protein kinase inhibitor is a compound of structural formula VIII.
19. The composition of claim 11, wherein the protein kinase inhibitor is a compound of structural formula IX.
20. The composition of claim 11, wherein the protein kinase inhibitor is a compound of structural formula XI.
21. An adduct comprising:
(a) a protein kinase inhibitor of claim 1; and
(b) an aspartate-lysine-cysteine (DKC) triad kinase domain.

22. The adduct of claim 21 wherein the DKC triad kinase domain is an ITK kinase domain.

23. The adduct of claim 21 wherein the DKC triad kinase domain is a BTK kinase domain.

24. The adduct of claim 21, wherein the protein kinase inhibitor is a compound of structural formula II.

25. The adduct of claim 21, wherein the protein kinase inhibitor is a compound of structural formula III.

26. The adduct of claim 21, wherein the protein kinase inhibitor is a compound of structural formula IV.

27. The adduct of claim 21, wherein the protein kinase inhibitor is a compound of structural formula V.

28. The adduct of claim 21, wherein the protein kinase inhibitor is a compound of structural formula VI.

29. The adduct of claim 21, wherein the protein kinase inhibitor is a compound of structural formula VII.

30. The adduct of claim 21, wherein the protein kinase inhibitor is a compound of structural formula VIII.

31. The adduct of claim 21, wherein the protein kinase inhibitor is a compound of structural formula IX.

32. The adduct of claim 21, wherein the protein kinase inhibitor is a compound of structural formula XI.

33. A complex comprising a protein kinase inhibitor of claim 1 which is bound to an aspartate-lysine-cysteine (DKC) triad kinase.

34. The complex of claim 33 wherein the DKC triad kinase is ITK.

35. The complex of claim 33 wherein the DKC triad kinase is BTK.

36. The complex of claim 33 which consists of the protein kinase inhibitor bound to the DKC triad kinase.

37. The complex of claim 33, wherein the protein kinase inhibitor is a compound of structural formula II.

38. The complex of claim 33, wherein the protein kinase inhibitor is a compound of structural formula III.

39. The complex of claim 33, wherein the protein kinase inhibitor is a compound of structural formula IV.

40. The complex of claim 33, wherein the protein kinase inhibitor is a compound of structural formula V.

41. The complex of claim 33, wherein the protein kinase inhibitor is a compound of structural formula VI.

42. The complex of claim 33, wherein the protein kinase inhibitor is a compound of structural formula VII.

43. The complex of claim 33, wherein the protein kinase inhibitor is a compound of structural formula VIII.

44. The complex of claim 33, wherein the protein kinase inhibitor is a compound of structural formula IX.

45. The complex of claim 33, wherein the protein kinase inhibitor is a compound of structural formula XI.

46. A method of inhibiting kinase activity, comprising contacting an aspartate-lysine-cysteine (DKC) triad kinase with a protein kinase inhibitor of claim 1 or a pharmaceutically acceptable salt thereof, whereby kinase activity of the DKC triad kinase is inhibited.

47. The method of claim 46 wherein the contacting occurs in a cell-free system.

48. The method of claim 46 wherein the contacting occurs in a cell.

49. The method of claim 48 wherein the cell is in vitro.

50. The method of claim 48 wherein the cell is in a patient.

51. The method of claim 50 wherein patient has an organ transplant, an autoimmune disease, or a blood cell malignancy.

52. The method of claim 46 wherein the DKC triad kinase is ITK.

53. The method of claim 46 wherein the DKC triad kinase is BTK.

54. The method of claim 46 wherein the protein kinase inhibitor has structural formula II.

55. The method of claim 46 wherein the protein kinase inhibitor has structural formula III.

56. The method of claim 46 wherein the protein kinase inhibitor has structural formula IV.

57. The method of claim 46 wherein the protein kinase inhibitor has structural formula V.

58. The method of claim 46 wherein the protein kinase inhibitor has structural formula VI.

59. The method of claim 46 wherein the protein kinase inhibitor has structural formula VII.

60. The method of claim 46 wherein the protein kinase inhibitor has structural formula VIII.

61. The method of claim 46 wherein the protein kinase inhibitor has structural formula IX.

62. The method of claim 46 wherein the protein kinase inhibitor has structural formula XI.

* * * * *

UNITED STATES PATENT AND TRADEMARK OFFICE
CERTIFICATE OF CORRECTION

PATENT NO. : 8,604,031 B2  
APPLICATION NO. : 11/750866  
DATED : December 10, 2013  
INVENTOR(S) : Flynn et al.

Page 1 of 1

It is certified that error appears in the above-identified patent and that said Letters Patent is hereby corrected as shown below:

In the Specification

Column 28, lines 60-65:

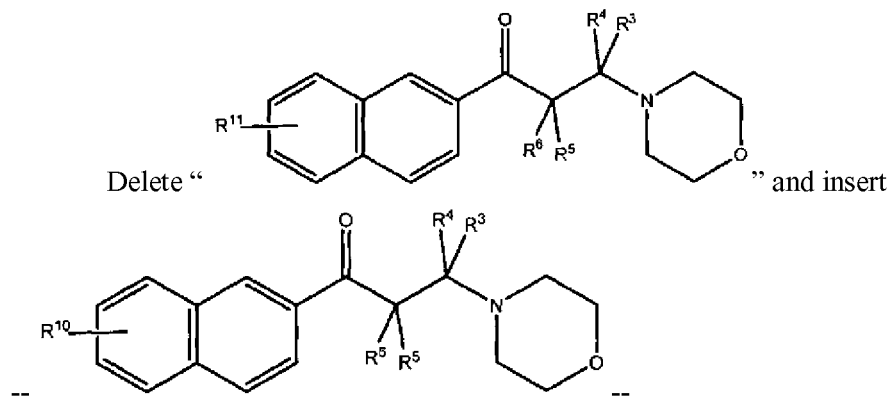

Delete " ... " and insert " ... " --

Column 110, Line 32:
  Delete "VI" and insert --V--

Column 110, Lines 33-44:

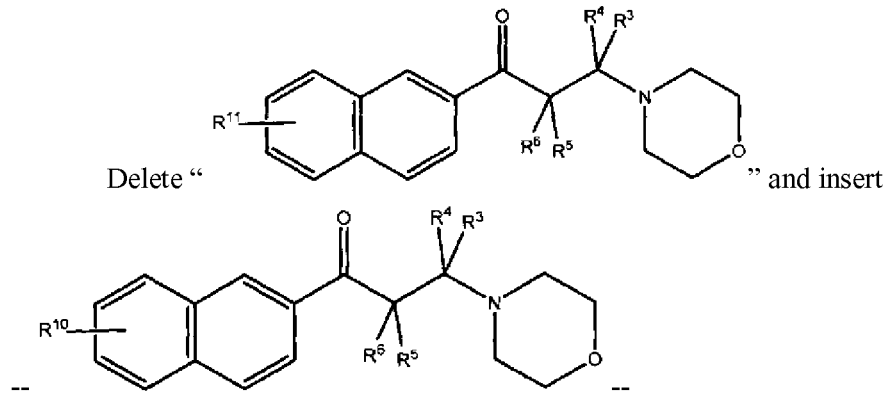

Delete " ... " and insert " ... " --

Signed and Sealed this  
Twenty-fifth Day of February, 2014

Michelle K. Lee  
*Deputy Director of the United States Patent and Trademark Office*